(12) United States Patent
Steindler et al.

(10) Patent No.: US 8,257,696 B2
(45) Date of Patent: Sep. 4, 2012

(54) INDEFINITE CULTURE OF HUMAN ADULT GLIA WITHOUT IMMORTALIZATION AND THERAPEUTIC USES THEREOF

(75) Inventors: Dennis A. Steindler, Gainesville, FL (US); Noah M. Walton, Chicago, IL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 1092 days.

(21) Appl. No.: 11/719,039

(22) PCT Filed: Nov. 21, 2005

(86) PCT No.: PCT/US2005/041978
§ 371 (c)(1),
(2), (4) Date: Nov. 10, 2007

(87) PCT Pub. No.: WO2006/055841
PCT Pub. Date: May 26, 2006

(65) Prior Publication Data
US 2010/0150875 A1    Jun. 17, 2010

Related U.S. Application Data

(60) Provisional application No. 60/629,469, filed on Nov. 19, 2004.

(51) Int. Cl.
*A61K 35/30* (2006.01)
*C12N 5/079* (2010.01)
*C12N 5/0797* (2010.01)

(52) U.S. Cl. ........ 424/93.7; 435/368; 435/377; 435/384
(58) Field of Classification Search ................. 424/93.7; 435/368, 377, 384
See application file for complete search history.

(56) References Cited

U.S. PATENT DOCUMENTS

| | | | | |
|---|---|---|---|---|
| 5,851,832 A | * | 12/1998 | Weiss et al. | 435/368 |
| 5,905,041 A | * | 5/1999 | Beug et al. | 435/372 |
| 6,638,763 B1 | * | 10/2003 | Steindler et al. | 435/368 |
| 2003/0103949 A1 | * | 6/2003 | Carpenter et al. | 424/93.21 |

OTHER PUBLICATIONS

Technical Resources—Media Formulations: N-2 Supplement (100X) liquid. downloaded on Oct. 19, 2010 from http://www.invitrogen.com/site/us/en/home/support/Product-Technical-Resources/media_formulation.166.html. p. 1.*

Tang et al., Long-Term Culture of Purified Postnatal Oligodendrocyte Precursor Cells: Evidence for an Intrinsinc Maturation Program that Plays out over Months, J. Cell. Biol., 2000, 148(5), pp. 971-984.

Chandran et al., Regional Potential for Oligodendrocyte Generation in the Rodent Embryonic Spinal Cord Following Exposure to EGF and FGF-2 Glia, 1998, 24(4), pp. 382-389.

* cited by examiner

*Primary Examiner* — Taeyoon Kim
(74) *Attorney, Agent, or Firm* — Thomas, Kayden, Horstemeyer & Risley, LLP

(57) ABSTRACT

Cell culture conditions for the isolation, maintenance, and indefinite expansion of human glia are established favoring the growth of neural precursor cells. Cultured cells proliferate indefinitely, express catalytic telomerase, and retain a non-immortalized phenotype. Compositions allow for the indefinite expansion of non-immortalized neural tissue for bioassay applications and restorative neuroscience.

3 Claims, 7 Drawing Sheets

INDEFINITE CULTURE OF HUMAN ADULT GLIA WITHOUT IMMORTALIZATION AND THERAPEUTIC USES THEREOF

CROSS-REFERENCE TO RELATED APPLICATIONS

This application is a §371 national stage entry of International Application No. PCT/US2005/041978, filed Nov. 21, 2005, which claims priority to U.S. Provisional Application No. 60/629,469, filed Nov. 19, 2004, both of which are hereby incorporated by reference.

STATEMENT REGARDING FEDERALLY SPONSORED RESEARCH OR DEVELOPMENT

This invention was made with Government support under Grant Nos. NS37556 and HL70143 awarded by the National Institute of Health. The Government has certain rights in this invention.

FIELD OF THE INVENTION

The invention is related to the infinite culturing of non-immortalized cells and the medical uses thereof.

BACKGROUND OF THE INVENTION

In cultured adult mammalian cells, growth arrest reliably occurs following a finite number of cell divisions. Commonly referred to as the Hayflick limit, this proliferative limit acts as an intractable species- and tissue-specific upper boundary in cultured somatic cells, with a limit of approximately 50 cell divisions for human lung fibroblasts. As a result of this restriction of cellular expansion, it is difficult to create standardized cultured somatic cells for widespread use, necessitating the use of immortal cell or tumor lines. Despite their durability as cell sources, all immortalized cells contain genetic mutations allowing them to circumvent proliferative limits, creating doubt in their efficacy as representative tissues for primary pharmacological applications and other bioassays. Similarly, in injured or otherwise damaged tissues transplantation of healthy and/or genetically modified cells, is currently an attractive therapeutic possibility. However, the limited ability to controllably expand cell populations is a barrier to autologous re-transplantation approaches, and necessitates the use of donor tissue, creating ethical and immunological concerns.

The underlying mechanisms defining proliferative lifespan are believed to vary between species. In cultured rodent cells, the regulatory entities establishing maximal replicative lifespan are unclear, and may involve a mechanism for counting mitotic events and/or phenomena related to culture conditions. Strong evidence indicates that the replicative lifespan of cultured human cells is primarily regulated by the length of telomeres, repeated hexameric nucleotide repeats at each end of the chromosomes that are believed to protect against replication-associated damage and chromosome end-fusion. In most somatic cells, chromosomal telomeres are progressively shortened as a result of incomplete end replication, and cells cease to divide upon reaching critical telomere length. Telomerase, the ribonuclear-protein enzyme involved in de novo extension of telomeres, appears essential for maintaining replicative competency, as human cells engineered to express catalytic telomerase reverse transcriptase (TERT) have a dramatically increased replicative lifespan in culture.

Mammalian somatic cells are limited to a finite number of mitotic events before entering irreversible growth arrest. This limited replicative competency provides an inherent restriction on expansion of cell populations in culture, and may be associated with age-related infirmity and disease in a broad range of tissues.

There is therefore, an urgent need in the art to provide long-term cultures of non-immortalized cells for drug discovery, transplantation, diagnostics, therapeutics and related medical purposes.

SUMMARY

Indefinite expansion of normal cells glia in vitro is overcome in humans upon application of appropriate growth conditions. In particular, conditions for the isolation, maintenance, and indefinite expansion of human glia using conditions favoring the growth of neural precursor cells are established. Cultured cells proliferate indefinitely, express catalytic telomerase, and retain a nonimmortalized phenotype. Using the compositions and methods described, show that an upper limit of division is plastic, allowing for the indefinite expansion of nonimmortalized neural tissue for bioassay applications and restorative neuroscience.

The invention is of significant economic value. As opposed to whole animal experiments, use of the long-term cultured non-immortalized cells in similar experiments provide efficient, cheap alternatives and are unburdened by ethical constraints. Whole animal experiments are laborious, expensive, and time consuming to perform. In addition, relatively large amounts of test compound must be synthesized in order to dose animals. For example, under current animal testing protocols, a minimum of 7 animals/data point is generally required due to variation in animals and high sensitivity required of the assays. Another major drawback of whole animal experiments are the number of variables which cannot be controlled and are difficult to assess. For example, if a compound is without effect, it may be due to rapid clearance from the blood, rapid metabolism, sequestration by a non-target tissue, or inability to penetrate the blood brain barrier. Dosing may be limited by toxicity to a sensitive non-target organ. Determining the contribution of these factors to a negative result is a major undertaking. Thus, negative results are not of use in generating structure-activity relationships to guide generation of improved compound structures.

In comparison to immortalized cells, the non-immortalized cells are not hindered by mutations, abnormal replication cycles, abnormal nucleic acid and polypeptide expression, and also provide a realistic in vitro means for determining any effects in the in vivo situation such as drug discovery, toxicity, diagnostics, therapy and the like.

The invention also has further advantages. The invention describes the production of committed cell types (e.g., neurons) from cell populations capable of dramatic expansion obtainable via a biopsy or other noninvasive procedure. This approach circumvents the need for embryonic stem cells and the development of immunorejection. For example, generation of new neurons for humans have thus far relied on the production of cells derived from embryonic or fetal tissue, which has attached concerns regarding the ethical use of this tissue source. This approach utilizes cells derived from adult tissue, providing the potential for autologous cell transplants that avoid ethical and immunological concerns (i.e., transplant rejection).

In a preferred embodiment, the present invention provides long term cultured non-immortalized cells (primary cell cultures) isolated from primary tissue. These cells provide models for neurodegenerative diseases, for example, Alzheimer's disease. The long-term cultured non-immortalized cells are useful, inter alia, for the identification of therapeutic compounds eliminating the need for animal models. For example, compounds can be administered to the cells and determining the changes in characteristics and changes indicative of neurodegenerative diseases in such cells, especially, the amount of neurofibrillary tangles and/or phosphorylated tau and/or tau fragments and/or the production and/or release of cytokines and/or microglia reactions and/or activations and/or inflammation and/or conversion of p35 to p25 and/or the levels and activities of protein kinases and/or any other characteristic or change indicative of neurodegenerative diseases in such cells.

In a preferred embodiment, a method of producing a non-immortalized long-term cultured cell comprises isolating cells from primary tissue, such as for example, anterolateral temporal lobe neocortex tissue. Preferably, the isolated cells are cultured in a first culture medium and the unattached cells are removed from the first culture medium. The unattached cells are preferably cultured in a proliferating culture medium, comprising growth factors.

In another preferred embodiment, the non-immortalized long-term cultured cells can be maintained in culture indefinitely and continue to divide (double) indefinitely without any cell senescence. Preferably, the non-immortalized long-term cultured cells undergo at least about 60 cell divisions without any detectable cell senescence; more preferably, the non-immortalized long-term cultured cells undergo about 100 cell divisions without any detectable cell senescence; more preferably, the non-immortalized long-term cultured cells undergo about 500 cell divisions without any detectable cell senescence; more preferably; the non-immortalized long-term cultured cells undergo about 1000 cell divisions without any detectable cell senescence; more preferably, the non-immortalized long-term cultured cells undergo about 5000 cell divisions without any detectable cell senescence. The non-immortalized cells of the invention are maintained indefinitely in culture, continue to proliferate, and telomerase expression is not coupled to a loss of key regulatory proteins required for immortalization. Thus, phenotype is a hybrid one, allowing expansion past proliferative limits while avoiding immortalizing mutations.

In another preferred embodiment, a non-immortalized cell is provided comprising a DNA construct comprising exogenous DNA which includes a DNA sequence homologous to a genomic DNA sequence of the cell, wherein the exogenous DNA comprises a DNA sequence that encodes a therapeutic molecule selected from the group consisting of neurotransmitters, growth factors, enzymes, cytokines, hormones, antigens, antibodies, clotting factors, regulatory proteins, transcription proteins, and receptors.

In another preferred embodiment, the non-immortalized cells are cultured under conditions appropriate for maintaining episomal vectors and/or homologous recombination between a DNA sequence in the DNA construct and genomic DNA to occur.

In another preferred embodiment, the non-immortalized long-term cultured cells comprising the expression construct can be maintained in culture indefinitely and continue to divide (double) indefinitely without any cell senescence. Preferably, the non-immortalized cells undergo at least about 60 cell divisions up to 5000 cell divisions without any detectable cell senescence. Preferably, the non-immortalized cells, comprising the expression construct, further comprise a selectable marker.

In another preferred embodiment, the expression construct encodes a therapeutic molecule, wherein the cell comprising the expression construct expresses the therapeutic molecule.

In another preferred embodiment, the non-immortalized cell is of mammalian origin.

In another preferred embodiment, a method of producing a non-immortalized long-term cultured cell expressing a therapeutic product, comprises a DNA construct comprising: 1) exogenous DNA sequences encoding a product not normally expressed in a cell of vertebrate origin; 2) a DNA sequence homologous with a genomic DNA sequence in the primary or secondary somatic cell; and 3) a DNA sequence encoding at least one selectable marker; administering to the cell the DNA construct; maintaining the cell under conditions appropriate for homologous recombination to occur between genomic DNA and a DNA sequence homologous with genomic DNA, thereby producing a recombinant cell of vertebrate origin having the DNA construct integrated into genomic DNA of the cell; and, culturing the recombinant cell under conditions appropriate for propagating the recombinant cell, thereby producing a clonal cell strain of recombinant somatic non-immortalized cells, wherein the clonal cell strain supplies the therapeutic product.

In another preferred embodiment, the non-immortalized cell is selected from the group consisting of: neural cells, brain cells, fibroblasts, keratinocytes, epithelial cells, endothelial cells, glial cells, lymphocytes, bone marrow cells, muscle cells, hepatocytes and precursors thereof. Preferably, the non-immortalized cell is of mammalian origin.

In another preferred embodiment, the exogenous DNA encodes a therapeutic product selected from the group consisting of: neurotransmitters, growth factors, enzymes, cytokines, hormones, antigens, antibodies, clotting factors, regulatory proteins, transcription proteins and receptors.

In another preferred embodiment, a non-immortalized cell produced by the administering an expression vector encoding a therapeutic molecule.

In another preferred embodiment, a method of producing a non-immortalized long-term cultured cell expressing a therapeutic product, comprises a DNA construct comprising exogenous DNA sequences encoding a product not normally expressed in a cell of vertebrate origin; a DNA sequence encoding at least one selectable marker; administering to the cell the DNA construct; maintaining the cell under conditions appropriate for maintaining the episomal construct, and, culturing the recombinant cell under conditions appropriate for propagating the recombinant cell, thereby producing a clonal cell strain of recombinant somatic non-immortalized cells, wherein the clonal cell strain supplies the therapeutic product.

In another preferred embodiment, a method for identifying candidate agents for treatment of diseases comprises culturing a non-immortalized cell in proliferating medium; exposing the non-immortalized cells to the candidate agent; and observing the effect of the candidate agent on the non-immortalized cells. The effects of the candidate agent include, but not limited to changes in nucleic acid expression, protein expression, nucleic acid and polypeptide trafficking, expression of receptors and the like.

In another preferred embodiment, new targets for therapeutic intervention, and new classes of compounds for the treatment of diseases, are identified. For example, in neurodegenerative diseases, such as Parkinson's disease, cysteine protease inhibitors, and specifically, calpain inhibitors, are capable of inhibiting tau proteolysis and thus the formation of tau fragments. Such inhibitors prevent the formation of neurofibrillary tangles induced, by conditions that raise the amount and/or activity of cathepsin D and/or conditions that lower the amount or concentration of cholesterol in the brain tissue. The method for identifying candidate agents for treatment of diseases comprise culturing a non-immortalized cell in proliferating medium; exposing the non-immortalized cells to the candidate agent; and observing the effect of the candidate agent on the non-immortalized cells. The observed effects are differential expression of nucleic acid sequences as compared to a control cell, and/or differential polypeptide expression as compared to a control cell and/or differential expression of receptors as compared to a control cell and/or differential expression of extracellular secretory products as compared to a control cell.

In another preferred embodiment, a method of isolating protoplasmic astrocytes comprises obtaining primary neural tissue from a subject; microdissecting the neural tissue; titurating the microdissected neural tissue, thereby producing a suspension comprising cells; culturing the cells onto uncoated tissue culturing systems; removing unattached cells and culturing said cells; thereby, isolating protoplasmic astrocytes. Protoplasmic astrocytes are cultured in proliferative medium comprising: N2 supplements, bovine pituitary extract, fetal calf serum, EGF and FGF and the EGF and FGF are supplemented bi-daily. The desired cell types are purified by isolating cells with antibodies specific for cell surface markers, wherein the cultured cells express markers comprising at least one of: GFAP, NeuN, PSA-NCAM, CNPase or O4. These cells are preferably, actively dividing cells and can undergo any number of cell divisions.

In another preferred embodiment, a method of treating neural diseases or disorders, comprises isolating a cell from primary tissue; culturing the isolated cells in a first culture medium; removing unattached cells from the first culture medium; and, culturing the removed unattached cells in a second culture medium; thereby, establishing a non-immortalized proliferating long term cultured cell; and, transplanting the non-immortalized cultured cell into a patient; thereby, treating a neural disease or disorder. Preferably, the cell is an autologous cell, wherein the cell is a neural progenitor cell.

In another preferred embodiment, the neural progenitor cell is cultured with a neural cell differentiating agent to induce a desired neural cell type for treatment of the neural disease or disorder. The cell can be cultured in a medium comprising a retinoid compound, brain-derived neurotrophic factor (BDNF), platelet-derived growth factor (PDGF), nerve growth factor (NGF), sonic hedgehog, sonic hedgehog aminoterminal peptide, neurotrophin (NT)-3, and neurotrophin (NT)-4; and; wherein the physiological and/or immunological feature comprises expression of a neuronal cell marker selected from the group consisting of neurofilament M, neural-specific β-tubulin, neural-specific enolase, and microtubule associated protein 2, or a combination of any of these; and wherein the morphological feature comprises one or more morphological neurite-like process(es) at least about 50 micrometers in length.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1A show the results obtained with immunofluorescence. High-passage (>60 cell divisions) cells express astrocyte markers GFAP, S100β, and glutamine synthetase (glut synth). Cytoskeletal proteins β-III-tubulin and nestin (expressed in dividing cells, inset) are also present. Scale bars: 50 μm (GFAP), 100 μM (additional images). Cells counterstained with DAPI. Voltage-clamp membrane recordings of these cells reveal prominent $Na^+$ and small $K^+$ channel activity. FIG. 1B shows that hippocampal and temporal cortex cells maintain a stable gliotypic morphology throughout culture. Scale bar: 150 μm. FIG. 1C are graphs showing that temporal cortex and hippocampus maintain similar, stable growth rates and continue logarithmic expansion throughout culture.

FIG. 2A are Western blots showing cells expressing major growth regulatory proteins longitudinally throughout culture (TERT compared to H1299 cell line). FIG. 2B shows a karyotypic analysis of high passage cells display normal ploidy and have no gross cytogenetic malformations. FIG. 2C is a graph showing proliferating cells displaying a marked increase in SA-β-Gal following addition of EGCG, X-irradiation, or aphidicolin evaluated 7 days later. FIG. 2D are images of cell cultures showing that seven days after growth arrest (EGCG shown) or growth factor withdrawal (-FGF shown) cultured cells express SA-β-Gal. However, only growth factor withdrawn cells lose TERT expression when evaluated 7 days later. Scale bar: 75 μm. FIG. 2E is a graph showing significant reduction in growth rate accompanies application of reversible growth inhibitors, which is reversed following washout. FIG. 2F is a graph showing matched high passage cells placed in either basic media (N2) or media containing EGF or FGF only (N2E, N2F) fail to thrive compared to proliferative conditions (N5EF) and subsequently become unviable. Data shown for temporal cortex high passage astrocytes. *$p<0.05$, student's t-test.

FIG. 3A shows the results from immunofluorescence of highpassage (>60 PDs) cells express astrocyte markers GFAP, S100β, and glutamine synthetase (glut synth). Cytoskeletal nestin (expressed in dividing cells, inset) is also present. Cells counterstained with DAPI. FIG. 3B shows voltage-clamp membrane recordings of these cells reveal prominent $Na^+$ and minimal $K^+$ channel activity. Data shown for temporal cortex cells. FIG. 3C shows HES astroglia derived from temporal cortex and hippocampus continue logarithmic expansion throughout culture. FIG. 3D shows a microscope view of hippocampal and temporal cortex cells maintaining a stable gliotypic morphology throughout culture. FIG. 3E is a graph showing both hippocampal and temporal cortex cells maintain an equivalent stable doubling rate throughout culture. Scale bars: 50 μm (GFAP), 100 μm (additional images) (a), 150 μm (d).

FIG. 4A is a blot showing that cells express major growth regulatory proteins longitudinally throughout culture (TERT compared to H1299 lung cancer cells). FIG. 4B are karyotyped HES cells displaying normal ploidy and have no gross cytogenetic malformations. FIG. 4C is a graph showing proliferating cells displaying a marked increase in SA-β-Gal when evaluated 7 days following addition of EGCG, X-irradiation, or aphidicolin. FIG. 4D are images showing that following growth arrest by an exogenous TERT inhibitor or growth factor withdrawal cultured cells express SA-β-Gal. However, only mitogen-withdrawn cells lose TERT expression when evaluated 7 days later. FIG. 4E is a graph showing that a significant reduction in growth rate accompanies application of reversible growth inhibitors, which is reversed following washout. Age-matched HES astroglia placed in either basic media (N2) or media containing EGF or FGF only (N2E, N2F) enter irreversible growth arrest compared to defined proliferative conditions (N2EF) and subsequently become unviable. Data shown for temporal cortex derived cells. *p<0.05, student's t-test. Scale bar: 75 µm (d).

FIG. 5A shows astroglial cells injected into the right lateral ventricle of postnatal day 3 mice were detectable with HNA in periventricular tissue adjacent to injection site (*). FIG. 5B shows HNA$^+$ cells (boxed in a) were primarily located within 100 µm of the ventricular wall in the ependymal and subependymal cell layer. FIGS. 5C-5E show HNA$^+$ cells (red) integrating into the LV wall display conserved morphology of astrotypic cells, and frequently coexpress GFAP (green). DAPI counterstain. FIG. 5F is a confocal micrograph showing GFAP$^+$ process extension from an HES astroglial cell into the subependymal zone. FIGS. 5G and 5H show activated dendrimer transfection of Pax6-eGFP of 30 PDs HES astroglia 3d post-transfection. DAPI counterstain. FIG. 5I is an image showing lentiviral-eGFP transfection of 30 PD HES astroglia at 20 moi. Scale bars: 40 µm (FIG. 5B), 25 µm (FIGS. 5C-5E), 8 µm (FIG. 5F), 20 µm (FIGS. 5G-5I).

FIG. 6A is a microscopic view showing proliferating cells (30 PDs) assume a rounded morphology immediately following addition of dibutyl cAMP, IBMX, and NGF. FIG. 6B is an immunofluorescent image showing that (b) 3 days following dedifferentiation, intermediate cells displaying a developmentally intermediate phenotype are appreciated. FIG. 6C is an immunofluorescent image showing maturing cells concurrently lose GFAP and continue to express β-III-tubulin. FIG. 6D show current and voltage clamp of 7 day old neurons. New neurons exhibit prominent Na$^+$ and K$^+$ channels, and were able to fire elicited action potentials when polarized to −60 mV. FIG. 6E is an immunofluorescent image showing that these cells maintain a characteristic neuronal morphology and express β-III-tubulin and neurofilament M (NF). Scale bars: 50 µm (FIG. 6A), 25 µm (FIG. 6B), 100 µm (FIG. 6C), 50 µm (FIG. 6E).

DETAILED DESCRIPTION

Figure 1:
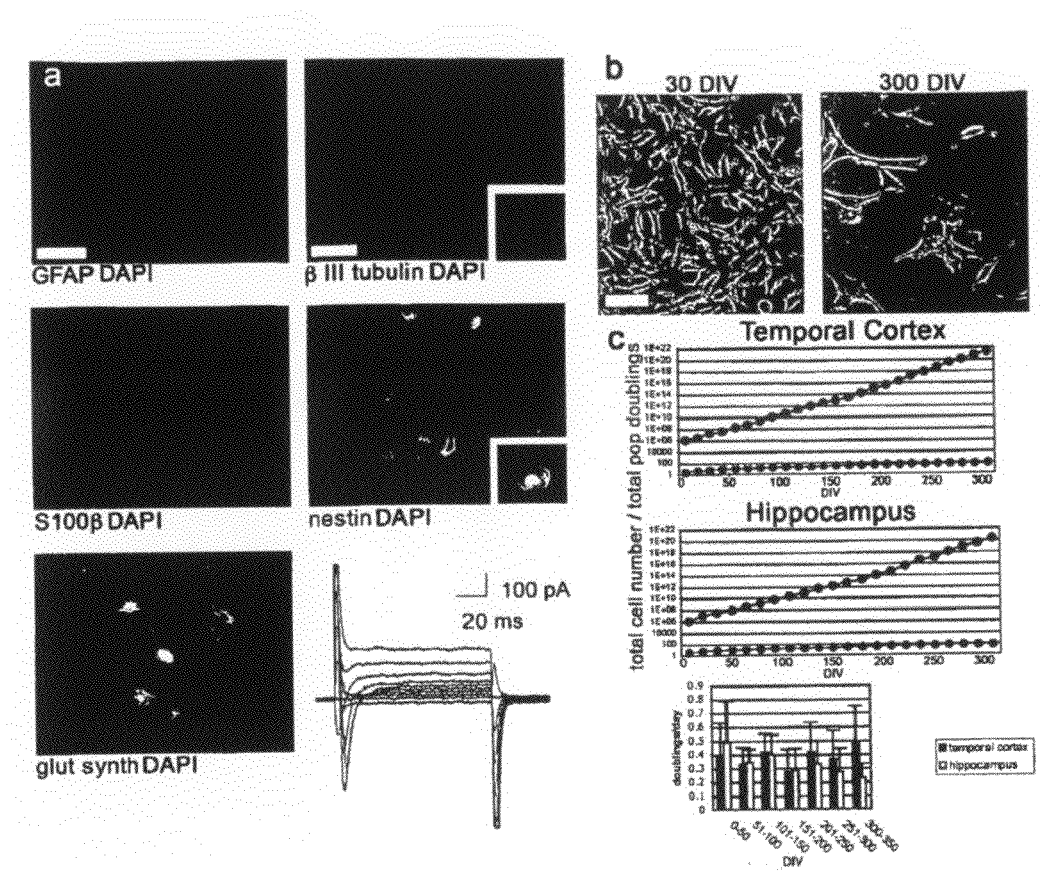
FIGS. 1A-1C depict extensively expanded cultured cells maintain astrocyte characteristics.

Compositions and methods for isolating purified populations of protoplasmic astrocytes from primary neural tissue are described, including culture conditions necessary for indefinite expansion of these populations. Human neural cells, similar to those of rodents, may be maintained beyond conventional proliferative limits in appropriate growth conditions. Cultured cells maintain a stable doubling rate throughout culture, and do not exhibit characteristics of transformed cells, including loss of key cell cycle checkpoint proteins, loss of sensitivity to arrestors of the cell cycle, and cell contact inhibition of growth.

Prior to setting forth the invention, the following definitions are provided.

DEFINITIONS

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

As used herein, the term "primary cell" or "non-immortalized cell" are used interchangeably throughout the specification and includes cells present in a suspension of cells isolated from a vertebrate tissue source (prior to their being plated, i.e., attached to a tissue culture substrate such as a dish or flask), cells present in an explant derived from tissue, both of the previous types of cells plated for the first time and cell suspensions derived from these plated cells. The term "secondary cell" or "cell strain" refers to cells at all subsequent steps in culturing. That is, the first time a plated primary cell is removed from the culture substrate and replated (passaged), it is referred to herein as a secondary cell, as are all cells in subsequent passages. Secondary cells are cell strains that consist of secondary cells that have been passaged one or more times. A non-immortalized cell consists of cells that: 1) have been passaged one or more times; 2) do not exhibit a finite number of mean population cell divisions in culture; 3) exhibit the properties of contact-inhibited, anchorage dependent growth (anchorage-dependence does not apply to cells that are propagated in suspension culture); and 4) are not immortalized. A "clonal cell strain" is defined as a cell strain that is derived from a single founder cell. A "heterogeneous cell strain" is defined as a cell strain that is derived from two or more founder cells.

The non-immortalized cells of the invention are maintained indefinitely in culture, continue to proliferate, and telomerase expression is not coupled to a loss of key regulatory proteins required for immortalization. Thus, phenotype is a hybrid one, allowing expansion past proliferative limits while avoiding immortalizing mutations.

"Neural cells" as defined herein, are cells that reside in the brain, central and peripheral nerve systems, including, but not limited to, nerve cells, glial cell, oligodendrocyte, microglia cells or neural stem cells.

"Neural progenitor" is an ectodermally-derived pluripotent stem cell having, as a physiological feature, a capacity, under physiological conditions that favor differentiation (e.g., presence of particular neurotrophic factors), to develop one or more morphological, physiological and/or immunological features specifically associated with a neuronal or glial cell type, i.e., neurons, astrocytes (i.e., astroglia), oligodendrocytes (i.e., oligodendroglia), and microglia. For example, bipotent neural progenitor cells differentiate into astrocytes after exposure to ciliary neurotrophic factor (CNTF), or into neuronal cells after exposure to platelet-derived growth factor (PDGF). (E.g., J. K. Park et al., *Bipotent cortical progenitor cells process conflicting cues for neurons and glia in a hierarchical manner*, J. Neurosci. 19(23): 10383-89 [1999]). Some neural progenitors are "neural restricted" progenitors, which can differentiate only into neurons. The presence of neural progenitors can be detected by functional testing under suitable physiological conditions to determine the course of development and differentiation into neuronal or glial cells. Preferably, neural progenitor cells are identified by detecting the expression of any of several well-defined specific markers, such as the cytoskeletal protein nestin and/or neural RNA-binding protein Musashi (MSI). (E.g., T. Nagata et al., *Structure, backbone dynamics and interactions with RNA of the C-terminal RNA-binding domain of a mouse neural RNA-binding protein, Musashi1*, J. Mol. Biol. 287(2):315-30 [1999]; P. Good et al., *The human Musashi homolog* 1 (MSI1) *gene encoding the homologue of Musashi/Nrp-1, a neural RNA-binding protein putatively expressed in CNS stem cells and neural progenitor cells*, Genomics 52(3):382-84 [1998]; S. Sakakibara et al., *Mouse-Musashi-1, a neural RNA-binding protein highly enriched in the mammalian CNS stem cell*, Dev. Biol. 176(2):230-42 [1996]).

The term "progenitor cell" is used synonymously with "stem cell." Hence, a neural progenitor cell is a neural stem cell. Both terms refer to an undifferentiated cell which is capable of proliferation and giving rise to more progenitor cells having the ability to generate a large number of mother cells that can in turn give rise to differentiated, or differentiable daughter cells. In a preferred embodiment, the term progenitor or stem cell refers to a generalized mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors.

In the context of cell ontogeny, the adjective "differentiated" is a relative term. A "differentiated cell" is a cell that has progressed further down the developmental pathway than the cell it is being compared with. Thus, pluripotent embryonic stem cells can differentiate to lineage-restricted precursor cells, such as hematopoetic cells, which are pluripotent for blood cell types; hepatocyte progenitors, which are pluripotent for hepatocytes; and various types of neural progenitors listed above. These in turn can be differentiated further to other types of precursor cells further down the pathway, or to an end-stage differentiated cell, which plays a characteristic role in a certain tissue type, and may or may not retain the capacity to proliferate further. Neurons, astrocytes, and oligodendrocytes are all examples of terminally differentiated cells.

A "differentiation agent", as used in this disclosure, refers to one of a collection of compounds that are used in culture systems of this invention to produce differentiated cells of the neural lineage (including precursor cells and terminally differentiated cells). No limitation is intended as to the mode of action of the compound. For example, the agent may assist the differentiation process by inducing or assisting a change in phenotype, promoting growth of cells with a particular phenotype or retarding the growth of others, or acting in concert with other agents through unknown mechanisms.

"Neuronal" cells, or "neuron-like" cells, include cells that display one or more neural-specific morphological, physiological and/or immunological features associated with a neuronal cell type, including sensory neuronal, motoneuronal, or interneuronal cell types. The practitioner can choose, in connection with a particular application, the operative criteria or subset of specific features used for determining whether a transdifferentiated cell belongs to a particular type of neuronal population. Useful criterial features include morphological features (e.g., long processes or neurites); physiological and/or immunological features, such as expression of a set of neural-specific markers or antigens (e.g., neurofilament M, neural-specific β-tubulin, neural-specific enolase, microtubule associated protein 2, or others); synthesis of neurotransmitter(s) (e.g., dopamine; expression of tyrosine hydroxylase—the key enzyme in dopamine synthesis; or gamma aminobutyric acid [GABA]); the presence of receptors for neurotransmitter(s); and/or physiological features such as membrane excitability and/or developmental response to particular cytokines or growth factors. An advantage of the transdifferentiated cell(s) of the invention is that it can be manipulated, in vitro in the presence of specific exogenously supplied signal molecules, or in vivo within specific microenvironments, into diverse neuronal types as defined by the practitioner's operative criteria.

A glial cell or "glial-like" cell includes a cell that has one or more glial-specific features, associated with a glial cell type, including a morphological, physiological and/or immunological feature specific to a glial cell (e.g. astrocytes or oligodendrocytes), for example, expression of the astroglial marker fibrillary acidic protein (GFAP) or the oligodendroglial marker O4.

In an additional embodiment of the invention, cells may be transfected with a nucleic acid of interest which encodes a neurologically relevant polypeptide. The term "neurologically relevant peptide" generally refers to a peptide or protein which catalyzes a reaction within the tissues of the central nervous system. Such peptides may be naturally occurring neural peptides, proteins or enzymes, or may be peptide or protein fragments which have therapeutic activity within the central nervous system.

Examples of neurologically relevant peptides include neural growth factors, neurotransmitters and enzymes used to catalyze the production of important neurochemicals or their intermediates. The peptide encoded by the nucleic acid may exogenous to the host or endogenous. For example, an endogenous gene that supplements or replaces deficient production of a peptide by the tissue of the host wherein such deficiency is a cause of the symptoms of a particular disorder. In this case, the cell lines act as an artificial source of the peptide. Alternatively, the peptide may be an enzyme which catalyzes the production of a therapeutic or neurologically relevant compound. Again, such compounds may be exogenous to the patient's system or may be an endogenous compound whose synthetic pathway is otherwise impaired. Examples of neurologically relevant compounds include tyrosine hydroxylase, nerve growth factor (NGF), brain derived neurotrophic factor (BDGF), basic fibroblast growth factor (bFGF) and glial cell line derived growth factor (GDGF).

As used herein, a "pharmaceutically acceptable" component is one that is suitable for use with humans and/or animals without undue adverse side effects (such as toxicity, irritation, and allergic response) commensurate with a reasonable benefit/risk ratio.

The terms "patient" or "individual" are used interchangeably herein, and is meant a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

As used herein, "ameliorated" or "treatment" refers to a symptom which is approaches a normalized value, e.g., is less than 50% different from a normalized value, preferably is less than about 25% different from a normalized value, more preferably, is less than 10% different from a normalized value, and still more preferably, is not significantly different from a normalized value as determined using routine statistical tests. For example, amelioration or treatment of depression includes, for example, relief from the symptoms of depression which include, but are not limited to changes in mood, feelings of intense sadness and despair, mental slowing, loss of concentration, pessimistic worry, agitation, and self-deprecation. Physical changes may also be relieved, including insomnia, anorexia and weight loss, decreased energy and libido, and the return of normal hormonal circadian rhythms. Another example, when using the terms "treating Parkinson's disease" or "ameliorating" as used herein means relief from the symptoms of Parkinson's disease which include, but are not limited to tremor, bradykinesia, rigidity, and a disturbance of posture.

"Diagnostic" or "diagnosed" means identifying the presence or nature of a pathologic condition. Diagnostic methods differ in their sensitivity and specificity. The "sensitivity" of a diagnostic assay is the percentage of cancer related disorders individuals who test positive (percent of "true positives"). Cancer related disorders individuals not detected by the assay are "false negatives." Subjects who are not cancer related disorders and who test negative in the assay, are termed "true negatives." The "specificity" of a diagnostic assay is 1 minus the false positive rate, where the "false positive" rate is defined as the proportion of those without the cancer who test positive. While a particular diagnostic method may not provide a definitive diagnosis of a condition, it suffices if the method provides a positive indication that aids in diagnosis.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

As used herein, "cell surface receptor" refers to molecules that occur on the surface of cells, interact with the extracellular environment, and transmit or transduce the information regarding the environment intracellularly in a manner that ultimately modulates transcription of specific promoters, resulting in transcription of specific genes.

An "allele" or "variant" is an alternative form of a gene. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The terms "amino acid" or "amino acid sequence" refer to an oligopeptide, peptide, polypeptide, or protein sequence, or a fragment of any of these, and to naturally occurring or synthetic molecules. In this context, "fragments," refer to fragments of protein which are preferably at least or 10 to about 30 or 50, 60, 70, 80 90 or 100 amino acids in length, more preferably at least 15, 20, 25, 30, 40, or 50 amino acids. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

As referred to herein, "fragments of a nucleic acid sequence" comprise at least about 10 or 15 nucleic acid residues (nucleotides), more preferably at least about 20, 30, 40, 50, 60, 70, 80, 90, 100, 150 or 200 nucleic acid residues.

As used herein, "extracellular signals" include a molecule or a change in the environment that is transduced intracellularly via cell surface proteins that interact, directly or indirectly, with the signal. An extracellular signal or effector molecule includes any compound or substance that in some manner specifically alters the activity of a cell surface protein. Examples of such signals include, but are not limited to, molecules such as acetylcholine, growth factors and hormones, that bind to cell surface and/or intracellular receptors and ion channels and modulate the activity of such receptors and channels.

As used herein, "extracellular signals" also include as yet unidentified substances that modulate the activity of a cellular receptor, and thereby influence intracellular functions. Such extracellular signals are potential pharmacological agents that may be used to treat specific cancers by modulating the activity of specific cell surface receptors.

"Orphan receptors" is a designation given to a receptors for which no specific natural ligand has been described.

The terms "polypeptide," "peptide" and "protein" are used interchangeably herein to refer to a polymer of amino acid residues. The terms apply to amino acid polymers in which one or more amino acid residue is an analog or mimetic of a corresponding naturally occurring amino acid, as well as to naturally occurring amino acid polymers. Polypeptides can be modified, e.g., by the addition of carbohydrate residues to form glycoproteins. The terms "polypeptide," "peptide" and "protein" include glycoproteins, as well as non-glycoproteins.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

"Antibody" refers to a polypeptide ligand substantially encoded by an immunoglobulin gene or immunoglobulin genes, or fragments thereof, which specifically binds and recognizes an epitope (e.g., an antigen). The recognized immunoglobulin genes include the kappa and lambda light chain constant region genes, the alpha, gamma, delta, epsilon and mu heavy chain constant region genes, and the myriad immunoglobulin variable region genes. Antibodies exist, e.g., as intact immunoglobulins or as a number of well characterized fragments produced by digestion with various peptidases. This includes, e.g., $F_{ab}'$ and $F_{(ab)'2}$ fragments. The term "antibody," as used herein, also includes antibody fragments either produced by the modification of whole antibodies or those synthesized de novo using recombinant DNA methodologies. It also includes polyclonal antibodies, monoclonal antibodies, chimeric antibodies, humanized antibodies, or single chain antibodies. "Fc" portion of an antibody refers to that portion of an immunoglobulin heavy chain that comprises one or more heavy chain constant region domains, CH1, CH2 and CH3, but does not include the heavy chain variable region.

"Immunoassay" is an assay that uses an antibody to specifically bind an antigen (e.g., a marker). The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

"Sample" is used herein in its broadest sense. A sample comprising polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Neural (neuronal) defects, disorders or diseases" as used herein refers to any neurological disorder, including but not limited to neurodegenerative disorders (Parkinson's; Alzheimer's) or autoimmune disorders (multiple sclerosis) of the central nervous system; memory loss; long term and short term memory disorders; learning disorders; autism, depression, benign forgetfulness, childhood learning disorders, close head injury, and attention deficit disorder; autoimmune disorders of the brain, neuronal reaction to viral infection; brain damage; depression; psychiatric disorders such as bipolarism, schizophrenia and the like; narcolepsy/sleep disorders (including circadian rhythm disorders, insomnia and narcolepsy); severance of nerves or nerve damage; severance of the cerebrospinal nerve cord (CNS) and any damage to brain or nerve cells; neurological deficits associated with AIDS; tics (e.g. Giles de la Tourette's syndrome); Huntington's chorea, schizophrenia, traumatic brain injury, tinnitus, neuralgia, especially trigeminal neuralgia, neuropathic pain, inappropriate neuronal activity resulting in neurodysthesias in diseases such as diabetes, MS and motor neuron disease, ataxias, muscular rigidity (spasticity) and temporomandibular joint dysfunction; Reward Deficiency Syndrome (RDS) behaviors in a subject; neurotoxicity caused by alcohol or substance abuse (e.g. ecstacy, methamphetamine, etc.).

The term "compound" as used herein (e.g., as in "candidate therapeutic agent" or "test compound") is meant to include both exogenously added test compounds and peptides endogenously expressed, from a peptide library. For example, in certain embodiments, the reagent cell also produces the test compound which is being screened. For instance, the reagent cell can produce. e.g., a test polypeptide, a test nucleic acid and/or a test carbohydrate which is screened for its ability to modulate the receptor/channel activity. In such embodiments, a culture of such reagent cells will collectively provide a library of potential effector molecules and those members of the library which either agonize or antagonize the receptor or ion channel function can be selected and identified. Moreover, it will be apparent that the reagent cell can be used to detect agents which transduce a signal via the receptor or channel of interest.

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

"Substantially purified" refers to nucleic acid molecules or proteins that are removed from their natural environment and are isolated or separated, and are at least about 60% free, preferably about 75% free, and most preferably about 90% free, from other components with which they are naturally associated.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

The phrase "differentially present" or "differential expression" refers to differences in the quantity and/or the frequency of a molecule (e.g. nucleic acid, polypeptide and the like) present in a cell taken from patients having for example, neural injury as compared to a control subject; cells expressing exogenous nucleic acid molecules, peptides etc. not present in a non-immortalized cell taken from normal patients. For example, a receptor can be a polypeptide which is present at an elevated level or at a decreased level in samples of patients with neural injury compared to samples of control subjects. Alternatively, a receptor can be a polypeptide which is detected at a higher frequency or at a lower frequency in samples of patients compared to samples of control subjects. A receptor can be differentially present in terms of quantity, frequency or both.

A polypeptide (or nucleic acid molecule) is differentially present or expressed between the two cells if the amount of the polypeptide (or nucleic acid molecule) in one cell is statistically significantly different from the amount of the polypeptide (or nucleic acid molecule) in the other cell. For example, a polypeptide (or nucleic acid molecule) is differentially present between the two cells if it is present at least about 120%, at least about 130%, at least about 150%, at least about 180%, at least about 200%, at least about 300%, at least about 500%, at least about 700%, at least about 900%, or at least about 1000% greater than it is present in the other cell, or if it is detectable in one cell and not detectable in the other.

Alternatively or additionally, a polypeptide (or nucleic acid molecule) is differentially present or expressed between the two sets of cells if the frequency of detecting the polypeptide in cells isolated from patients' suffering from, for example, neural injury and/or neuronal disorders, is statistically significantly higher or lower than in the control cells. For example, a polypeptide is differentially present between the two sets of cells if it is detected at least about 120%, at least about 130%, at least about 150%, at least about 180%, at least about 200%, at least about 300%, at least about 500%, at least about 700%, at least about 900%, or at least about 1000% more frequently or less frequently observed in one set of cells than the other set of cells.

A "precursor cell" can be any cell in a cell differentiation pathway that is capable of differentiating into a more mature cell. As such, the term "precursor cell population" refers to a group of cells capable of developing into a more mature cell. A precursor cell population can comprise cells that are totipotent, cells that are pluripotent and cells that are stem cell lineage restricted (i.e. cells capable of developing into less than all hematopoietic lineages, or into, for example, only cells of erythroid lineage). As used herein, the term "totipotent cell" refers to a cell capable of developing into all lineages of cells. Similarly, the term "totipotent population of cells" refers to a composition of cells capable of developing into all lineages of cells. Also as used herein, the term "pluripotent cell" refers to a cell capable of developing into a variety (albeit not all) lineages and are at least able to develop into all hematopoietic lineages (e.g., lymphoid, erythroid, and thrombocytic lineages). For example, a pluripotent cell can differ from a totipotent cell by having the ability to develop into all cell lineages except endothelial cells. A "pluripotent population of cells" refers to a composition of cells capable of developing into less than all lineages of cells but at least into all hematopoietic lineages. As such, a totipotent cell or composition of cells is less developed than a pluripotent cell or compositions of cells. As used herein, the terms "develop", "differentiate" and "mature" all refer to the progression of a cell from the stage of having the potential to differentiate into at least two different cellular lineages to becoming a specialized cell. Such terms can be used interchangeably for the purposes of the present application.

As used herein, the term "population" refers to cells having the same or different identifying characteristics. The term "lineage" refers to all of the stages of the development of a cell type, from the earliest precursor cell to a completely mature cell (i.e. a specialized cell).

A stem cell population of the present invention is capable of developing into cells of mesodermal cell lineage, of ectodermal cell lineage or of endodermal cell lineage. As used herein, mesodermal cells include cells of connective tissue, bone, cartilage, muscle, blood and blood vessel, lymphatic and lymphoid organ, notochord, pleura, pericardium, peritoneum, kidney and gonad. Ectodermal cells include epidermal tissue cells, such as those of nail, hair, glands of the skin, the nervous system, the external sense organs (e.g., eyes and ears) and mucous membranes (such as those of the mouth and anus). Endodermal cells include cells of the epithelium such as those of the pharynx, respiratory tract (except the nose), digestive tract, bladder and urethra cells. Preferred cells within a stem cell population of the present invention include cells of at least one of the following cellular lineages: hematopoietic cell lineage, endothelial cell lineage, epithelial cell lineage, muscle cell lineage and neural cell lineage. Other preferred cells within a stem cell population of the present invention include cells of erythroid lineage, endothelial lineage, leukocyte lineage, thrombocyte lineage, erythroid lineage (including primitive and definitive erythroid lineages), macrophage lineage, neutrophil lineage, mast cell lineage, megakaryocyte lineage, natural killer cell lineage, eosinophil lineage, T cell lineage, endothelial cell lineage and B cell lineage.

The term "DNA construct" and "vector" are used herein to mean a purified or isolated polynucleotide that has been artificially designed and which comprises at least two nucleotide sequences that are not found as contiguous nucleotide sequences in their natural environment.

As used herein, the term "administering a molecule to a cell" (e.g., an expression vector, nucleic acid, a angiogenic factor, a delivery vehicle, agent, and the like) refers to transducing, transfecting, microinjecting, electroporating, or shooting, the cell with the molecule. In some aspects, molecules are introduced into a target cell by contacting the target cell with a delivery cell (e.g., by cell fusion or by lysing the delivery cell when it is in proximity to the target cell).

A cell has been "transduced" or "transfected" by exogenous or heterologous nucleic acids when such nucleic acids have been introduced inside the cell. Administered DNA may or may not be integrated (covalently linked) with chromosomal DNA making up the genome of the cell. In prokaryotes, yeast, and mammalian cells for example, the administered DNA may be maintained on an episomal element, such as a plasmid. In a eukaryotic cell, a stably transformed cell is one in which the administered DNA has become integrated into a chromosome so that it is inherited by daughter cells through chromosome replication. This stability is demonstrated by the ability of the eukaryotic cell to establish non-immortalized cells or clones comprising a population of daughter cells containing the administered DNA. A "clone" is a population of cells derived from a single cell or common ancestor by mitosis. A "cell line" is a clone of a primary cell that is capable of stable growth in vitro for many generations (e.g., at least about 10).

As used interchangeably herein, the terms "oligo-nucleotides", "polynucleotides", and "nucleic acids" include RNA, DNA, or RNA/DNA hybrid sequences of more than one nucleotide in either single chain or duplex form. The term "nucleotide" as used herein as an adjective to describe molecules comprising RNA, DNA, or RNA/DNA hybrid sequences of any length in single-stranded or duplex form. The term "nucleotide" is also used herein as a noun to refer to individual nucleotides or varieties of nucleotides, meaning a molecule, or individual unit in a larger nucleic acid molecule, comprising a purine or pyrimidine, a ribose or deoxyribose sugar moiety, and a phosphate group, or phosphodiester linkage in the case of nucleotides within an oligonucleotide or polynucleotide. Although the term "nucleotide" is also used herein to encompass "modified nucleotides" which comprise at least one modifications (a) an alternative linking group, (b) an analogous form of purine, (c) an analogous form of pyrimidine, or (d) an analogous sugar, all as described herein.

The phrase "having a length of N bases" or "having a length of N nucleotides" is used herein to describe lengths along a single nucleotide strand, of a nucleic acid molecule, consisting of N individual nucleotides.

As used herein, the term "bind", refers to an interaction between the bases of an oligonucleotide which is mediated through base-base hydrogen bonding. One type of binding is "Watson-Crick-type" binding interactions in which adenine-thymine (or adenine-uracil) and guanine-cytosine base-pairs are formed through hydrogen bonding between the bases. An example of this type of binding is the binding traditionally associated with the DNA double helix.

The term "complementary" and "complementary oligonucleotide" are used herein to refer to oligonucleotides or portions of polynucleotides which are capable of forming Watson-Crick-type binding interactions with another particular oligonucleotide or particular region of a polynucleotide. Generally, unless otherwise noted, the use of the term "complementary" means that all of the bases of the shorter of the two nucleotides, or portions of the nucleotides being discussed, are capable of Watson-Crick-type binding to a particular region of the other longer, or equal sized, oligonucleotide.

As used herein, "molecule" is used generically to encompass any vector, antibody, protein, drug and the like which are used in therapy and can be detected in a patient by the methods of the invention. For example, multiple different types of nucleic acid delivery vectors encoding different types of genes which may act together to promote a therapeutic effect, or to increase the efficacy or selectivity of gene transfer and/or gene expression in a cell. The nucleic acid delivery vector may be provided as naked nucleic acids or in a delivery vehicle associated with one or more molecules for facilitating entry of a nucleic acid into a cell. Suitable delivery vehicles include, but are not limited to: liposomal formulations, polypeptides; polysaccharides; lipopolysaccharides, viral formulations (e.g., including viruses, viral particles, artificial viral envelopes and the like), cell delivery vehicles, and the like.

As used herein, the term "oligonucleotide" refers to a polynucleotide formed from naturally occurring bases and pentofuranosyl groups joined by native phosphodiester bonds. This term effectively refers to naturally occurring species or synthetic species formed from naturally occurring subunits or their close homologs. The term "oligonucleotide" may also refer to moieties which function similarly to naturally occurring oligonucleotides but which have non-naturally occurring portions. Thus, oligonucleotides may have altered sugar moieties or intersugar linkages. Exemplary among these are the phosphorothioate and other sulfur-containing species which are known for use in the art. In accordance with some preferred embodiments, at least some of the phosphodiester bonds of the oligonucleotide have been substituted with a structure which functions to enhance the ability of the compositions to penetrate into the region of cells where the RNA or DNA whose activity to be modulated is located. It is preferred that such substitutions comprise phosphorothioate bonds, methyl phosphonate bonds, or short chain alkyl or cycloalkyl structures. In accordance with other preferred embodiments, the phosphodiester bonds are substituted with other structures which are, at once, substantially non-ionic and non-chiral, or with structures which are chiral and enantiomerically specific. Persons of ordinary skill in the art will be able to select other linkages for use in practice of the invention.

Oligonucleotides may also include species which include at least some modified base forms. Thus, purines and pyrimidines other than those normally found in nature may be so employed. Similarly, modifications on the pentofuranosyl portion of the nucleotide subunits may also be effected, as long as the essential tenets of this invention are adhered to. Examples of such modifications are 2'-O-alkyl- and 2'-halogen-substituted nucleotides. Some specific examples of modifications at the 2' position of sugar moieties which are useful in the present invention are OH, SH, $SCH_3$, F, $OCH_3$, OCN, $O(CH_2)_nNH_2$ or $O(CH_2)_nCH_3$ where n is from 1 to about 10, and other substituents having similar properties.

The "observed effects" in a cell when a candidate agent is tested are measured in ways known to one of ordinary skill in the art. For example, one such method is by measuring cell phenotypes. The phenotypes of cells and any phenotypic changes can be evaluated by flow cytometry after immunofluorescent staining using monoclonal antibodies that will bind membrane proteins characteristic of various cell types. Another method is by measuring cell function. This may be done biochemically, by measuring the expression of enzymes, mRNA's, genes, proteins, or other metabolites within the cell, or secreted from the cell. Bioassays may also be used to measure functional cell differentiation.

The term "vector" as used herein (including "expression vector") means any nucleic acid sequence of interest capable of being incorporated into a host cell resulting in the expression of a nucleic acid of interest. Vectors can include, e.g., linear nucleic acid sequences, plasmids, cosmids, phagemids, and extrachromosomal DNA. Specifically, the vector can be a recombinant DNA. Also used herein, the term "expression", or "gene expression" is meant to refer to the production of the protein product of the nucleic acid sequence of interest, including transcription of the DNA and translation of the RNA transcript. These can include vectors, liposomes, naked DNA, adjuvant-assisted DNA, gene gun, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc. The vectors can be chromosomal, non-chromosomal or synthetic. Preferred vectors include viral vectors, fusion proteins and chemical conjugates. Retroviral vectors include Moloney murine leukemia viruses. DNA viral vectors are preferred. Viral vectors can be chosen to introduce the cytokine or chemokine to cells of choice. Such vectors include pox vectors such as orthopox or avipox vectors, herpesvirus vectors such as herpes simplex I virus (HSV) vector (Geller, A. I et al, *J. Neurochem.,* 64:487 (1995); Lim, F., et al., in DNA Cloning: Mammalian Systems, D. Glover, Ed. (Oxford Univ. Press, Oxford, England) (1995); Geller, A. I. et al., *Proc. Natl. Acad. Sci. USA* 87:1149 (1990)) Adenovirus vectors (LeGal LaSalle et al., *Science,* 259:988 (1993); Davidson, et al., *Nat. Genet.* 3:219 (1993); Yang et al., *J. Virol.* 69:2004 (1995)) and Adeno-associated virus vectors (Kaplitt, M. G. et al., *Nat. Genet.* 8:148 (1994)). Pox viral vectors introduce the gene into the cells cytoplasm. Avipox virus vectors result in only short term expression of the nucleic acid. Adenovirus vectors, adeno-associated virus vectors and herpes simplex virus vectors are preferred for introducing the nucleic acid into neural cells. The adenovirus vector results in a shorter term expression (about 2 months) than adeno-associated virus (about 4 months), which in turn is shorter than HSV vectors. The vectors can be introduced by standard techniques, e.g. infection, transfection, transduction or transformation. Examples of modes of gene transfer include for example, naked DNA calcium phosphate precipitation, DEAE dextran, electroporation, protoplast fusion, lipofection, cell microinjection and viral vectors.

Vectors can be constructed which also comprise a detectable/selectable marker gene. In preferred embodiments these marker genes are fluorescent proteins such as green fluorescent protein (GFP), cyan—(CFP), yellow—(YFG), blue—

(BFP), red—(RFP) fluorescent proteins; enhanced green fluorescent protein (EGFP), EYFP, EBFP, Nile Red, dsRed, mutated, modified, or enhanced forms thereof, and the like.

As used herein, the "green-fluorescence protein" is a gene construct which in transfected or infected cells, respectively, shines green under ultraviolet light and thus enables the detection of a cell transfected or infected, respectively, with GFP in a simple manner.

Uses of green fluorescent protein for the study of gene expression and protein localization are well known. The compact structure makes GFP very stable under diverse and/or harsh conditions such as protease treatment, making GFP an extremely useful reporter in general.

New versions of green fluorescent protein have been developed, such as a "humanized" GFP DNA, the protein product of which has increased synthesis in mammalian cells. One such humanized protein is "enhanced green fluorescent protein" (EGFP). Other mutations to green fluorescent protein have resulted in blue-, cyan- and yellow-green light emitting versions.

Endogenously fluorescent proteins have been isolated and cloned from a number of marine species including the sea pansies *Renilla reniformmis, R. kollikeri* and *R. mullerei* and from the sea pens *Ptilosarcus, Stylatula* and *Acanthoptilum*, as well as from the Pacific Northwest jellyfish, *Aequorea victoria*; Szent-Gyorgyi et al. (SPIE conference 1999), D. C. Prasher et al., Gene, 111:229-233 (1992) and several species of coral (Matz et al. *Nature Biotechnology*, 17 969-973 (1999). These proteins are capable of forming a highly fluorescent, intrinsic chromophore through the cyclization and oxidation of internal amino acids within the protein that can be spectrally resolved from weakly fluorescent amino acids such as tryptophan and tyrosine.

As used herein, the term "antibody" refers to a polypeptide or group of polypeptides which are comprised of at least one binding domain, where an antibody binding domain is formed from the folding of variable domains of an antibody molecule to form three-dimensional binding spaces with an internal surface shape and charge distribution complementary to the features of an antigenic determinant of an antigen, which allows an immunological reaction with the antigen. Antibodies include recombinant proteins comprising the binding domains, as wells as fragments, including Fab, Fab', F(ab)$_2$, and F(ab')$_2$ fragments.

As used herein, an "antigenic determinant" is the portion of an antigen molecule that determines the specificity of the antigen-antibody reaction. This term will be used interchangeably with the term "target antigen". An "epitope" refers to an antigenic determinant of a polypeptide. An epitope can comprise as few as 3 amino acids in a spatial conformation which is unique to the epitope. Generally an epitope consists of at least 6 such amino acids, and more usually at least 8-10 such amino acids. Methods for determining the amino acids which make up an epitope include x-ray crystallography, 2-dimensional nuclear magnetic resonance, and epitope mapping e.g. the Pepscan method described by H. Mario Geysen et al. 1984. *Proc. Natl. Acad. Sci. U.S.A.* 81:3998-4002; PCT Publication No. WO 84/03564; and PCT Publication No. WO 84/03506.

Non-Immortalized Cells in Long-Term Culture

In a preferred embodiment, indefinite cell cultures of non-immortalized cells are produced. Culture conditions for the isolation, establishment, and indefinite culture of a population of adult human glial cells also favor the growth of neural progenitor cells.

In another preferred embodiment, cells isolated from tissue are maintained for at least about 300 days in culture (>60 cell divisions) without cellular senescence; more preferably, cells isolated from primary tissue are maintained for at least about 400 days in culture (>80 cell divisions) without cellular senescence; more preferably, cells isolated from primary tissue are maintained for at least about 500 days in culture (>100 cell divisions) without cellular senescence; more preferably, cells isolated from primary tissue are maintained for at least about 800 days in culture (>160 cell divisions) without cellular senescence; more preferably, isolated cells from primary tissue are maintained for at least about 1000, 1500, 2000, 3000 and 4000 days without cellular senescence.

In another preferred embodiment, isolated cells from primary tissue undergo at least about 60 cellular cell divisions without cellular senescence; preferably, isolated cells from primary tissue undergo at least about 100 cellular cell divisions without cellular senescence; more preferably, isolated cells undergo at least about 200 cellular cell divisions without cellular senescence; more preferably, isolated cells undergo at least about 300 cellular cell divisions without cellular senescence; more preferably, isolated cells undergo at least about 500 cellular cell divisions without cellular senescence; more preferably, isolated cells undergo at least about 750 cellular cell divisions without cellular senescence; more preferably, isolated cells undergo at least about 1000 cellular cell divisions without cellular senescence.

In another preferred embodiment, isolated long-term non-immortalized cell cultures from primary tissue do not undergo spontaneous immortalizing mutations.

In another preferred embodiment, isolated long-term non-immortalized cell cultures from primary tissue express telomerase throughout culture, and retain sensitivity to endogenous and exogenous cell cycle arrestors. Without wishing to be bound by theory, these findings shown in detail in the examples which follow, suggest that an upper limit of mitotic events in human cells can be tractable under appropriate mitogenic stimulation, providing applications in maintaining aged, injured, or diseased tissue. Additionally, the capability for the apparently limitless expansion of glia provides new and exciting possibilities for bioassays and tissue regeneration.

In another preferred embodiment, isolated long-term non-immortalized cells from primary tissue are used to expand glial cell populations for diagnostic neurobiology as well as for therapeutic approaches involving tissue replacement. By extensively expanding primary cells from various brain regions, a substrate for neural cell bioassays is created (i.e., primary drug testing) without relying on clonally derived cell lines that contain potentially masking genotoxic mutations or inaccurately reflect the homeostenosis of target cells.

Comparison of cells derived from the hippocampus and temporal cortex revealed no differences in growth rates, cellular composition, or significant physiological factors. This is surprising, as the hippocampus is believed to contain astrocyte-like NSCs show self-renewal and multipotentiality in vitro and in vivo. However, the lack of neurosphere production and failure to generate multiple lineages from adherent tissue using standard protocols suggests these cells are not NSCs.

High passage cells exposed to exogenous cell cycle inhibitors (aphidicolin, EGCG) lose their ability to proliferate in culture, but continue to express telomerase. Upon removal of growth inhibitors cultured cells return to previous levels of proliferation. However, upon growth factor withdrawal, telomerase expression ceases and continued proliferation is effectively reduced, neither of which is restored upon reversion to proliferative media. This observation provides for several interesting possibilities. First, these results suggest a system whereby environmental mitogens (provided in constant supply) provide a synergistic growth effect, allowing for both TERT expression and unlimited expansion. A loss of environmental support factors may trigger a demonstrably irreversible loss of TERT expression, which may effectively mortalize cells or possibly, in the case of aged cells, trigger their immediate entry into a state of replicative senescence. This possibility may explain the heterogeneity of age-related deficits among individuals, and may serve to reconcile many of the observed discrepancies between in vivo and in vitro experiments. The appreciation of rapid senescence with the loss of TERT expression in aged cells suggests that both telomere length and telomerase expression may be critical to the maintenance of dividing cell populations.

Alternative Methods for Isolation of Cells

Sources of Stem Cells: This invention can be practiced using stem cells of various types, which may include the following non-limiting examples. U.S. Pat. No. 5,851,832 reports multipotent neural stem cells obtained from brain tissue. U.S. Pat. No. 5,766,948 reports producing neuroblasts from newborn cerebral hemispheres. U.S. Pat. Nos. 5,654,183 and 5,849,553 report the use of mammalian neural crest stem cells. U.S. Pat. No. 6,040,180 reports in vitro generation of differentiated neurons from cultures of mammalian multi-potential CNS stem cells. WO 98/50526 and WO 99/01159 report generation and isolation of neuroepithelial stem cells, oligodendrocyte-astrocyte precursors, and lineage-restricted neuronal precursors. U.S. Pat. No. 5,968,829 reports neural stem cells obtained from embryonic forebrain and cultured with a medium comprising glucose, transferrin, insulin, selenium, progesterone, and several other growth factors.

Except where otherwise required, the invention can be practiced using stem cells of any vertebrate species. Included are stem cells from humans; as well as non-human primates, domestic animals, livestock, and other non-human mammals.

In a preferred embodiment, neural progenitor cells are isolated from a patient. Amongst the stem cells suitable for use in this invention are primate pluripotent stem (pPS) cells derived from tissue formed after gestation, such as a blastocyst, or fetal or embryonic tissue taken any time during gestation. Non-limiting examples are primary cultures or established lines of embryonic stem cells or embryonic germ cells.

Embryonic Stem Cells: Embryonic stem cells can be isolated from blastocysts of members of the primate species (Thomson et al., *Proc. Natl. Acad. Sci. USA* 92:7844, 1995). Human embryonic stem (hES) cells can be prepared from human blastocyst cells using the techniques described by Thomson et al. (U.S. Pat. No. 5,843,780; *Science* 282:1145, 1998; *Curr. Top. Dev. Biol.* 38:133 ff., 1998) and Reubinoff et al, *Nature Biotech.* 18:399 (2000)).

Briefly, human blastocysts are obtained from human in vivo preimplantation embryos. Alternatively, in vitro fertilized (IVF) embryos can be used, or one-cell human embryos can be expanded to the blastocyst stage (Bongso et al., *Hum Reprod* 4: 706, 1989). Embryos are cultured to the blastocyst stage in G1.2 and G2.2 medium (Gardner et al., *Fertil. Steril.* 69:84, 1998). The zona pellucida is removed from developed blastocysts by brief exposure to pronase (Sigma). The inner cell masses are isolated by immunosurgery, in which blastocysts are exposed to a 1:50 dilution of rabbit anti-human spleen cell antiserum for 30 min, then washed for 5 min three times in DMEM, and exposed to a 1:5 dilution of Guinea pig complement (Gibco) for 3 min (Solter et al., *Proc. Natl. Acad. Sci. USA* 72:5099, 1975). After two further washes in DMEM, lysed trophectoderm cells are removed from the intact inner cell mass (ICM) by gentle pipetting, and the ICM plated on mEF feeder layers.

After 9 to 15 days, inner cell mass-derived outgrowths are dissociated into clumps, either by exposure to calcium and magnesium-free phosphate-buffered saline (PBS) with 1 mM EDTA, by exposure to dispase or trypsin, or by mechanical dissociation with a micropipette; and then replated on mEF in fresh medium. Growing colonies having undifferentiated morphology are individually selected by micropipette, mechanically dissociated into clumps, and replated. ES-like morphology is characterized as compact colonies with apparently high nucleus to cytoplasm ratio and prominent nucleoli. Resulting ES cells are then routinely split every 1-2 weeks by brief trypsinization, exposure to Dulbecco's PBS (containing 2 mM EDTA), exposure to type IV collagenase (.about. 200 U/mL; Gibco) or by selection of individual colonies by micropipette. Clump sizes of about 50 to 100 cells are optimal.

Antibodies are particularity useful for the preparation of substantially pure neural progenitor cells and non-immortalized cells. By "substantially pure" herein is meant that at least about 50% of the cells present after sorting are either neural progenitor cells or neurons, with at least about 70% preferred and at least about 90% particularly preferred. By "neural progenitor cells" herein is meant any one or a mixture of cells types, including proneuronal progenitors (proNP), normeuronal progenitors (NNP), and neuronal progenitors (NP). All of these cell types contain the RET antigen as demonstrated by the binding of RET antibody and are thus RET$^+$. (U.S. Pat. No. 6,890,724, incorporated herein by reference).

c-RET is an orphan receptor tyrosine kinase is one of the earliest surface markers that distinguishes postmigratory from early migrating neural crest cells (Anderson, D. J., *Persp. Dev. Neuro.* 2:191-201 (1994)). RET is not simply a marker for enteric progenitors but is also essential for their proper development, as shown by genetic studies in both mice (Schuchardt, A., D'Agati, V., Larsson-Blomberg, L., Costantini, F. and Pachnis, V., *Nature* 367:380-383 (1994)) and humans (Edery, P., Lyonnet, S., Mulligan, L. M., Pelet, A., Dow, E., Abel, L., Holder, S., Nihoul-Fekete, C., Ponder, B. A. J. and Munnich, A., *Nature* 367:378-380 (1994). In situ hybridization experiments have indicated that RET is not expressed by early migrating trunk neural crest cells in vivo but is expressed after these cells have aggregated to form the primordia of autonomic ganglia.

Both Ret and Mash1 are regulatory genes essential for the development of subsets of autonomic neurons, as shown by targeted gene disruption experiments in mice (Guillemot, F. and Joyner, A. L., *Mech. Devel.* 42:171-185 1993); Schuchardt, A., D'Agati, V., Larsson-Blomberg, L., Costantini, F. and Pachnis, V., *Nature* 367:380-383 (1994)). In addition, both genes are initially expressed in otherwise morphologically and antigenically undifferentiated neural crest cells (Lo, L., Johnson, J. E., Wuenschell, C. W., Saito, T. and Anderson, D. J., *Genes & Dev.* 5:1524-1537 (1991).; Guillemot, F. and Joyner, A. L., *Mech. Devel.* 42:171-185 (1993); Pachnis, V., Mankoo, B. and Costantini, F., *Development* 119, in press.). While Ret is genetically essential for the development of all enteric neurons, the precise developmental operation it controls is not yet established.

The fact that Ret and Mash1 are expressed sequentially (Guillemot, F. and Joyner, A. L., *Mech. Devel.* 42:171-185 (1993); Lo, L., Guillemot, F., Joyner, A. L. and Anderson, D. J., *Persp. Dev. Neuro.* 2:191-201 (1994)) in the same cells and that both are required for the differentiation of at least a subpopulation of peripheral autonomic neurons raises the possibility that there is an interaction between these two genes. For example, signaly through RET could lead to the expression of MASH1; conversely, MASH1 could be required for the maintenance or up-regulation of RET expression. However, though Ret is required for the differentiation of all enteric neurons (Schuchardt, A., D'Agati, V., Larsson-Blomberg, L., Costantini, F. and Pachnis, V., *Nature* 367:380-383 (1994)), it is not essential for the initial differentiation of sympathetic neurons. Conversely, Mash1 is required for sympathetic neuron differentiation (Guillemot, F. and Joyner, A. L., *Mech. Devel.* 42:171-185 (1993)) but not for the differentiation of some enteric neurons. These data suggest that Mash1 expression does not require Ret function in sympathetic neurons, and that Ret function does not require Mash1 expression in late-generated enteric neurons.

ProNP cells are characterized as being able to give rise to both neurons and glia (as well as other unidentified normeuronal cells) and are thus considered multipotent. By "multipotent" herein is meant that a single cell is able to give rise to asymmetric daughter cells, as is known in the art, i.e. they are capable, under the conditions described, of self-regeneration and differentiation to some but not all types of neurons and glia in vitro. ProNP cells are also characterized as expressing: (1) nestin, a neuroepithilial stem cell marker (Lendahl, U., Zimmerman, L. B. and McKay, R. D. G., *Cell* 60:585:595 (1990)) also expressed by neural crest stem cells (NCSCs); Stemple, D. L. and Anderson, D. J., *Cell* 71:973-985 (1992); (2) the low affinity growth nerve growth factor (LNGFR) receptor, p75, also a surface marker of NCSCs (Stemple and Anderson, supra); (3) MASH1, a basic-helix-loop-helix transcriptional regulator (Lo, L., Johnson, J. E., Wuenschell, C. W., Saito, T. and Anderson, D. J., *Genes & Dev.* 5:1524-1537 (1991)), which is not expressed by NCSCs and thus serves as a distinguishing factor between proNP cells and NCSCs. ProNP cells do not express lineage markers such as neurofilaments, S100, glial fibrillary acidic protein (GFAP), sulfatide, myelin protein Po and peripherin. Neurofilaments are neuron-specific intermediate filament proteins. Three neurofilament (NF) proteins have been reported: NF68, a 68 kD protein also called NF-L (Light); NF160, a 160 kD protein also called NF-M (Medium); NF200, 200 kD protein also called NF-H (Heavy). Thus, proNP cells are characterized as being nestin$^+$, p75$^+$, RET$^+$, MASH1$^+$, and lin$^-$.

Normeuronal progenitor cells (NNP) are characterized as being RET$^+$, nestin$^+$, and MASH1$^+$. In contrast to the proNP cells however, NNP cells are not capable of differentiation into neurons and glia, since only glia and possibly some as yet unidentified normeuronal cells.

Neuronal progenitor (NP) cells are characterized by being RET$^+$, nestin$^+$, and MASH1$^+$, but may or may not contain neuron lineage markers such as neurofilament. NP cells are further characterized by their commitment to forming neurons, as evidenced in two ways. First of all, NP cells demonstrate an insensitivity to glial growth factor (GGFII, also called neuregulin; Marchionni, M. A., Goodearl, A. D. J., Chen, M. S., Bermingham-McDonogh, O., Kirk, C., Hendricks, M., Danehy, F., Misumi, D., Sudhalter, J., Kobayashi, K., Wroblewski, D., Lynch, C., Baldassare, M., Hiles, I., Davis, J. B., Hsuan, J. J., Totty, N. F., Otsu, M., McBurney, R. N., Waterfield, M. D., Stroobant, P. and Gwynne, D., *Nature* 362:312-318 (1993)), a protein known to exert an instructive influence on trunk-derived NSCSs, repressing neuronal differentiation and promoting glial differentiation by most or all of the cells (Shah, N. M., Marchionni, M. A., Isaacs, I., Stroobant, P. W. and Anderson, D. J., *Cell* 77:349-360 (1994)). In addition, is has previously been demonstrated that neuronal differentiation from NCSCs is strongly inhibited or delayed on a substrate that contains fibronectin but not polylysine (Stemple, D. L. and Anderson, D. J., *Cell* 71:973:985 (1992)). NP cells, in contrast, when plated on fibronectin plates in the absence of polylysine, generally generated neurons, thus indicating that this substrate is unable to inhibit or delay neuronal differentiation. Thus, NP cells differentiate to neurons despite the presence of both soluble factors and extracellular matrix molecules that can inhibit neuronal differentiation by early migrating trunk NCSCs.

A subset of neural progenitor cells is separated from other cells on the basis of RET antibody binding, and may be further separated by binding to other surface markers known in the art.

Procedures for separation may include magnetic separation, using antibody-coated magnetic beads, affinity chromatography and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. Dead cells may be eliminated by selection with dyes associated with dead cells (propidium iodide, LDS). Red blood cells may be removed by elutriation, hemolysis, Ficoll-Paque gradients, etc. Any technique may be employed which is not unduly detrimental to the viability of the selected cells.

Conveniently, the antibodies are conjugated with labels to allow for ease of separation of the particular cell type, e.g. magnetic beads; biotin, which binds with high affinity to avidin or streptavidin; fluorochromes, which can be used with a fluorescence activated cell sorter; haptens; and the like. Multi-color analyses may be employed with the FACS or in a combination of immunomagnetic separation and flow cytometry. Multi-color analysis is of interest for the separation of cells based on multiple surface antigens, e.g. RET$^+$, p75$^+$, MASH1$^+$, etc. Fluorochromes which find use in a multi-color analysis include phycobiliproteins, e.g. phycoerythrin and allophycocyanins; fluorescein and Texas red.

In one embodiment of the subject invention an antibody directed to a desired surface marker, such as for example, GFAP, NeuN, PSA-NCAM, CNPase, O4 or RET antibody is directly or indirectly conjugated to a magnetic reagent, such as a superparamagnetic microparticle (microparticle). Direct conjugation to a magnetic particle is achieved by use of various chemical linking groups, as known in the art. Antibody can be coupled to the microparticles through side chain amino or sufhydryl groups and heterofunctional cross-linking reagents. A large number of heterofunctional compounds are available for linking to entities. A preferred linking group is 3-(2-pyridyldithio)propionic acid N-hydroxysuccinimide ester (SPDP) or 4-(N-maleimidomethyl)-cyclohexane-1-carboxylic acid N-hydroxysuccinimide ester (SMCC) with a reactive sulfhydryl group on the antibody and a reactive amino group on the magnetic particle.

Alternatively, the antibody is indirectly coupled to the magnetic particles. The antibody is directly conjugated to a hapten, and hapten-specific, second stage antibodies are conjugated to the particles. Suitable haptens include digoxin, digoxigenin, FITC, dinitrophenyl, nitrophenyl, avidin, biotin, etc. Methods for conjugation of the hapten to a protein, i.e. are known in the art, and kits for such conjugations are commercially available.

The antibody is added to a cell sample. The amount of antibody necessary to bind a particular cell subset is empirically determined by performing a test separation and analysis. The cells and antibody are incubated for a period of time sufficient for complexes to form, usually at least about five minutes, more usually at least about 10 minutes, and usually not more than one hour, more usually not more than about 30 minutes.

The cells may additionally be incubated with antibodies or binding molecules specific for cell surface markers known to be present or absent on neural cells and neural progenitor cells.

The labeled cells are separated in accordance with the specific antibody preparation. Fluorochrome labeled antibodies are useful for FACS separation, magnetic particles for immunomagnetic selection, particularly high gradient magnetic selection (HGMS), etc. Exemplary magnetic separation devices are described in WO/90/07380, PCT/US96/00953 and EP 438,520, herein incorporated by reference.

The purified cell population may be collected and propagated in any appropriate medium, as is generally described in the Examples.

The subject cell compositions may find use in a variety of ways. By providing for maturation, proliferation and differentiation into one or more selected lineages through specific different growth factors the progenitor cells may be used as a source of committed cells.

The cells may also be used in the identification, isolation and evaluation of factors associated with the differentiation and maturation of neural cells. Thus, the cells may be used in assays to determine the activity of media, such as conditioned media, evaluate fluids for growth factor activity, involvement with dedication of lineages, or the like.

The cells may be used for the treatment of genetic diseases. Genetic diseases associated with neural cells may be treated by genetic modification of autologous or allogeneic stem cells to correct a genetic defect or treat to protect against disease. Examples of PNS disorders in mice include the trembler and shiverer strains. The trembler mutation is thought to involve a defect in the structural gene for myelin basic protein (MBP). This mutation maps to the same region of chromosome 11 as does the MBP gene. This mutation results in the defective myelination of axons in the PNS. An analogous disorder is seen in humans, Charcot-Marie-Tooth syndrome, which results in progressive neuropathic muscular atrophy.

Similarly, the shiverer mutation in mice results in a severe myelin deficiency throughout the CNS and a moderate hypomyelination in the PNS. Severe shivering episodes are seen 12 days after birth. An analogous disorder is seen in humans, Guillaum-Barre' disease, which is characterized by an acute febrile polyneuritis.

The cells of the invention are introduced into a mammal exhibiting a neurological disorder to examine the therapeutic potential of these cells. These cells are preferably isolated from a mammal having similar MHC genotypes or the host mammal is immunosuppressed using drugs such as cyclosporin A. Preferably, the cells are autologous cells. The cells are injected into an area containing various peripheral nerves known to be effected in a particular mammal or into the spinal cord or brain for mammals which show involvement of the CNS. The cells are injected at a range of concentrations to determine the optimal concentration into the desired site. Alternatively, the cells are introduced in a plasma clot or collagen gel to prevent rapid dispersal of cells from the site of injection. The effect of this treatment on the neurological status of the model animal is noted. Desired therapeutic effects in the above mutant mice include the reduction or cessation of seizures or improved movement of lower motor extremities.

Other diseases may be corrected by introduction of the wild-type gene into the subject cells, either by homologous or random recombination. Alternatively, normal allogeneic progenitor cells may be transplanted. Diseases other than those associated with neural cells may also be treated, where the disease is related to the lack of a particular secreted product such as hormone, enzyme, interferon, factor, or the like.

The cells may be frozen at liquid nitrogen temperatures and stored for long periods of time, being thawed and capable of being reused.

Transduced Cells

Primary and secondary cells to be transfected by the present method can be obtained from a variety of tissues and include all cell types which can be maintained in culture. Preferred cells are protoplasmic astrocytes isolated from primary neural tissue. Other primary and secondary cells which can be transfected by the present method include fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells, hepatocytes and precursors of these somatic cell types. Primary cells are preferably obtained from the individual to whom the transfected primary or secondary cells are administered. However, primary cells may be obtained from a donor (other than the recipient) of the same species or another species (e.g., nonhuman primates, mouse, rat, rabbit, cat, dog, pig, cow, bird, sheep, goat, horse).

When the genetic modification is for the production of a biologically active substance, the substance can be one that is useful for the treatment of a given CNS disorder. The cells can be genetically modified to express a biologically active agent, such as growth factors, growth factor receptors, neurotransmitters, neurotransmitter synthesizing genes, neuropeptides, and chromaffin granule amine transporter. For example, it may be desired to genetically modify cells so they secrete a proliferation-inducing growth factor or a differentiation-inducing growth factor. Growth factor products useful in the treatment of CNS disorders include NGF, BDNF, the neurotrophins, CNTF, amphiregulin, FGF-1, FGF-2, EGF, TGFα, TGF, PDGF, IGFs, and the interleukins.

Cells can also be modified to express a certain growth factor receptor (r) including, but not limited to, p75 low affinity NGF receptor, CNTF receptor, the trk family of neurotrophin receptors (trk, trkb, trkC), EGFr, FGFr, and amphiregulin receptors. Cells can be engineered to produce various neurotransmitters or their receptors such as serotonin, L-dopa, dopamine, norepinephrine, epinephrine, tachykinin, substance P, endorphin, enkephalin, histamine, N-methyl D-aspartate, glycine, glutamate, GABA, ACh, and the like. Useful neurotransmitter-synthesizing genes include TH, DDC, DBH, PNMT, GAD, tryptophan hydroxylase, ChAT, and histidine decarboxylase. Genes that encode for various neuropeptides, which may prove useful in the treatment of CNS disorders, include substance-P, neuropeptide-Y, enkephalin, vasopressin, VIP, glucagon, bombesin, CCK, somatostatin, calcitonin gene-related peptide, and the like.

The genetically modified cells can be implanted for cell therapy or gene therapy into the CNS of a recipient in need of the biologically active molecule produced by the genetically modified cells. Transplantation techniques are detailed below and in the Examples which follow.

Alternatively, the genetically modified cells can be subjected to various differentiation protocols in vitro prior to implantation. For example, genetically modified neural cells may be removed from the culture medium, which allows proliferation and differentiated using any of the protocols, described above. The protocol used depends upon the type of genetically modified cell desired. Once the cells have differentiated, they are again assayed for expression of the desired protein. Cells having the desired phenotype can be isolated and implanted into recipients in need of the protein or biologically active molecule that is expressed by the genetically modified cell.

Characteristics of Neural Precursors and Terminally Differentiated Cells

Cells can be characterized according to a number of phenotypic criteria. The criteria include but are not limited to microscopic observation of morphological features, detection or quantitation of expressed cell markers, enzymatic activity, or neurotransmitters and their receptors, and electrophysiological function.

Certain cells embodied in this invention have morphological features characteristic of neuronal cells or glial cells. The features are readily appreciated by those skilled in evaluating the presence of such cells. For example, characteristic of neurons are small cell bodies, and multiple processes reminiscent of axons and dendrites. Cells of this invention can also be characterized according to whether they express phenotypic markers characteristic of neural cells of various kinds.

Markers of interest include but are not limited to β-tubulin III, microtubule-associated protein 2 (MAP-2), or neurofilament, characteristic of neurons; glial fibrillary acidic protein (GFAP), present in astrocytes; galactocerebroside (GalC) or myelin basic protein (MBP), characteristic of oligodendrocytes; Oct-4, characteristic of undifferentiated hES cells; Nestin, characteristic of neural precursors and other cells; and both A2B5 and polysialylated NCAM, as already described. While A2B5 and NCAM are instructive markers when studying neural lineage cells, it should be appreciated that these markers can sometimes be displayed on other cell types, such as liver or muscle cells. MAP-2 is a more stringent marker for fully differentiated neurons of various types.

Tissue-specific markers listed in this disclosure and known in the art can be detected using any suitable immunological technique: such as flow immunocytochemistry for cell-surface markers, immunohistochemistry (for example, of fixed cells or tissue sections) for intracellular or cell-surface markers, Western blot analysis of cellular extracts, and enzyme-linked immunoassay, for cellular extracts or products secreted into the medium. Expression of an antigen by a cell is said to be "antibody-detectable" if a significantly detectable amount of antibody will bind to the antigen in a standard immunocytochemistry or flow cytometry assay, optionally after fixation of the cells, and optionally using a labeled secondary antibody or other conjugate (such as a biotin-avidin conjugate) to amplify labeling.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods. See U.S. Pat. No. 5,843,780 for further details. Sequence data for the particular markers listed in this disclosure can be obtained from public database, such as GenBANK. Expression at the mRNA level is said to be "detectable" according to one of the assays described in this disclosure if the performance of the assay on cell samples according to standard procedures in a typical controlled experiment results in clearly discernable hybridization or amplification product. Expression of tissue-specific markers as detected at the protein or mRNA level is considered positive if the level is at least 2-fold, and preferably more than 10- or 50-fold above that of a control cell, such as an undifferentiated pPS cell, a fibroblast, or other unrelated cell type.

Also characteristic of neural cells, particularly terminally differentiated cells, are receptors and enzymes involved in the biosynthesis, release, and reuptake of neurotransmitters, and ion channels involved in the depolarization and repolarization events that relate to synaptic transmission. Evidence of synapse formation can be obtained by staining for synaptophysin. Evidence for receptivity to certain neurotransmitters can be obtained by detecting receptors for .gamma.-amino butyric acid (GABA), glutamate, dopamine, 3,4-dihydroxyphenylalanine (DOPA), noradrenaline, acetylcholine, and serotonin. Cells that are positive for tyrosine hydroxylase (TH), can be measured by immunocytochemistry or mRNA expression. This generally considered in the art to be a marker for dopamine synthesizing cells.

To elucidate further mature neurons present in a differentiated population, the cells can be tested according to functional criteria. For example, calcium flux can be measured by any standard technique, in response to a neurotransmitter, or other environmental condition known to affect neurons in vivo. First, neuron-like cells in the population are identified by morphological criteria, or by a marker such as NCAM. The neurotransmitter or condition is then applied to the cell, and the response is monitored. The cells can also be subjected to standard patch-clamp techniques, to determine whether there is evidence for an action potential, and what the lag time is between applied potential and response.

Other desirable features consistent with functioning neurons, oligodendrocytes, astrocytes, and their precursors can also be performed according to standard methods to confirm the quality of a cell population according to this invention, and optimize conditions for proliferation and differentiation of the cells.

Telomerization of Neural Precursors

It is desirable that neural precursors have the ability to replicate in certain drug screening and therapeutic applications, and to provide a reservoir for the generation of differentiated neuronal and glial cells. The cells of this invention can optionally be telomerized to increase their replication potential, either before or after they progress to restricted developmental lineage cells or terminally differentiated cells.

Cells are telomerized by genetically altering them by transfection or transduction with a suitable vector, homologous recombination, or other appropriate technique, so that they express the telomerase catalytic component (TERT), typically under a heterologous promoter that increases telomerase expression beyond what occurs under the endogenous promoter. Particularly suitable is the catalytic component of human telomerase (hTERT), provided in International Patent Application WO 98/14592. For certain applications, species homologs like mouse TERT (WO 99/27113) can also be used. Transfection and expression of telomerase in human cells is described in Bodnar et al., *Science* 279:349, 1998 and Jiang et al., *Nat. Genet.* 21:111, 1999. In another example, hTERT clones (WO 98/14592) are used as a source of hTERT encoding sequence, and spliced into an EcoRI site of a PBBS212 vector under control of the MPSV promoter, or into the EcoRI site of commercially available pBABE retrovirus vector, under control of the LTR promoter.

The following assay kits are available commercially for research purposes: TRAPeze™, XL Telomerase Detection Kit (Cat. s7707; Intergen Co., Purchase N.Y.); and TeloTAGGG Telomerase PCR ELISAplus (Cat. 2,013,89; Roche Diagnostics, Indianapolis Ind.). TERT expression can also be evaluated at the mRNA by RT-PCR. Available commercially for research purposes is the LightCycler TeloTAGGG hTERT quantification kit (Cat. 3,012,344; Roche Diagnostics). Continuously replicating colonies will be enriched by further culturing under conditions that support proliferation, and cells with desirable phenotypes can optionally be cloned by limiting dilution.

In certain embodiments of this invention, cells are differentiated into multipotent or committed neural precursors, and then genetically altered to express TERT. In other embodiments of this invention, cells are genetically altered to express TERT, and then differentiated into neural precursors or terminally differentiated cells. Successful modification to increase TERT expression can be determined by TRAP assay, or by determining whether the replicative capacity of the cells has improved.

Exogenous DNA

Exogenous DNA incorporated into primary or secondary cells by the present method is: 1) DNA which encodes a translation or transcription product whose expression in primary or secondary cells is desired, such as a product useful to treat an existing condition or prevent it from occurring and 2) DNA which does not encode a gene product but is itself useful, such as in treating an existing condition or preventing it from occurring.

DNA incorporated into primary or secondary cells can be an entire gene encoding an entire desired product or a gene portion which encodes, for example, the active or functional portion(s) of the product. The product can be, for example, a hormone, a cytokine, an antigen, an antibody, an enzyme, a clotting factor, a transport protein, a receptor, a regulatory protein, a structural protein, an anti-sense RNA, a ribozyme or a protein or a nucleic acid which does not occur in nature (i.e., a novel protein or novel nucleic acid). The DNA can be obtained from a source in which it occurs in nature or can be produced, using genetic engineering techniques or synthetic processes. The DNA transfected into primary or secondary cells can encode one or more therapeutic products. After transfection into primary or secondary cells, the exogenous DNA is stably incorporated into the recipient cell's genome (along with the additional sequences present in the DNA construct used), from which it is expressed or otherwise functions.

Selectable Markers

A variety of selectable markers can be incorporated into primary cells. For example, a selectable marker which confers a selectable phenotype such as drug resistance, nutritional auxotrophy, resistance to a cytotoxic agent or expression of a surface protein, can be used. Selectable marker genes which can be used include neo, gpt, dhfr, ada, pac, hyg, mdrl and hisD. The selectable phenotype conferred makes it possible to identify and isolate recipient primary or secondary cells. Selectable markers can be divided into two categories: positive selectable and negative selectable. In positive selection, cells expressing the positive selectable marker are capable of surviving treatment with a selective agent (such as neo, gpt, dhfr, ada, pac, hyg, mdrl and hisD). In negative selection, cells expressing the negative selectable marker are destroyed in the presence of the selective agent (e.g., tk, gpt).

DNA Constructs

In a preferred embodiment, AAV (Adeno-Associated virus) is a preferred construct. DNA constructs, which include exogenous DNA encoding a desired product, targeting sequences for homologous recombination and, optionally, DNA encoding one or more selectable markers are used to transfect primary or secondary cells in which homologous recombination is to occur. In this embodiment, DNA sequences necessary for expression of the exogenous DNA will generally be present as well. DNA constructs which include exogenous DNA sequences which do not encode a gene product (and are the desired product) and, optionally, include DNA encoding a selectable marker, can also be used to transfect primary and secondary cells.

The exogenous DNA, targeting sequences and selectable marker can be introduced into cells on a single DNA construct or on separate constructs. The total length of the DNA construct will vary according to the number of components (exogenous DNA, targeting sequences, selectable marker gene) and the length of each. The entire construct length will generally be at least about 20 nucleotides. In a construct in which the exogenous DNA has sufficient homology with genomic DNA to undergo homologous recombination, the construct will include a single component, the exogenous DNA. In this embodiment, the exogenous DNA, because of its homology, serves also to target integration into genomic DNA and additional targeting sequences are unnecessary. Such a construct is useful to knock out, replace or repair a resident DNA sequence, such as an entire gene, a gene portion, a regulatory element or portion thereof or regions of DNA which, when removed, place regulatory and structural sequences in functional proximity. It is also useful when the exogenous DNA is a selectable marker.

In another embodiment, the DNA construct includes exogenous DNA and one or more separate targeting sequences, generally located at both ends of the exogenous DNA sequence. Targeting sequences are DNA sequences normally present in the primary or secondary cell genome in the genome of the cells as obtained [e.g., an essential gene, a nonessential gene or noncoding DNA, or present in the genome through a previous modification]. Such a construct is useful to integrate exogenous DNA encoding a therapeutic product, such as a hormone, a cytokine, an antigen, an antibody, an enzyme, a clotting factor, a transport protein, a receptor, a regulatory protein, a structural protein, an antisense RNA, a ribozyme or a protein or a nucleic acid which does not occur in nature. In particular, exogenous DNA can encode one of the following: Factor VIII, Factor IX, erythropoietin, alpha-1 antitrypsin, calcitonin, glucocerebrosidase, growth hormone, low density lipoprotein (LDL) receptor, IL-2 receptor and its antagonists, insulin, globin, immunoglobulins, catalytic antibodies, the interleukins, insulin-like growth factors, superoxide dismutase, immune responder modifiers, parathyroid hormone, interferons, nerve growth factors, tissue plasminogen activators, and colony stimulating factors. Such a construct is also useful to integrate exogenous DNA which is a therapeutic product, such as DNA sequences sufficient for sequestration of a protein or nucleic acid in the transfected primary or secondary cell, DNA sequences which bind to a cellular regulatory protein, DNA sequences which alter the secondary or tertiary chromosomal structure and DNA sequences which are transcriptional regulatory elements into genomic DNA of primary or secondary cells.

In another embodiment, the DNA construct includes exogenous DNA, targeting DNA sequences and DNA encoding at least one selectable marker. The order of construct components can be: targeting sequences-exogenous DNA-DNA encoding a selectable marker(s)-targeting sequences. In this embodiment, one or more selectable markers are included in the construct, which makes selection based on a selectable phenotype possible. Cells that stably integrate the construct will survive treatment with the selective agent can be identified by a variety of techniques, including PCR, Southern hybridization and phenotypic screening.

In another preferred embodiment, the order of components in the DNA construct can be: targeting sequence-selectable marker 1—targeting sequence—selectable marker 2. In this embodiment selectable marker 2 displays the property negative selection, that is, the gene product of selectable marker 2 can be selected against by growth in an appropriate media formulation containing an agent (typically a drug or metabolite analog) which kills cells expressing selectable marker 2. Recombination between the targeting sequences flanking selectable marker 1 with homologous sequences in the host cell genome results in the targeted integration of selectable marker 1, while selectable marker 2 is not integrated. Such recombination events generate cells which are stably transfected with selectable marker 1 but not stably transfected with selectable marker 2, and such cells can be selected for by growth in the media comprising the selective agent which selects for selectable marker 1 and the selective agent which selects against selectable marker 2.

Typically the gene of interest is cloned into an expression vector. As used herein, the term "expression vector" refers to a vector which (due to the presence of appropriate transcriptional and/or translational control sequences) is capable of expressing a DNA molecule which has been cloned into the vector and of thereby producing a polypeptide or protein. A nucleic acid molecule, such as DNA, is said to be "capable of expressing" a polypeptide if it contains nucleotide sequences which contain transcriptional and translational regulatory information and such sequences are "operably linked" to a nucleotide sequence that encodes the polypeptide. An operable linkage is a linkage in which the regulatory DNA sequences and the DNA sequence sought to be expressed are connected in such a way as to permit gene expression. Regulatory elements include elements such as a promoter, an initiation codon, a stop codon and a polyadenylation signal.

Expression of the cloned sequences occurs when the expression vector is introduced into an appropriate host cell. In this case, the preferred host cell is a neuronal cell. Procedures for preparing expression vectors are known to those of skill in the art and can be found in Sambrook et al., Molecular Cloning: A Laboratory Manual, 2nd Ed. Cold Spring Harbor Press, Cold Spring Harbor, N.Y. (1989).

As discussed above, a preferred use of nucleic acid sequences identified in the present invention, is for the generation of treatments that ameliorate diseases or disorders such as neural disorders or neural injury. A gene of interest such as a receptor, receptor related genes can be expressed by a vector containing a DNA segment encoding the wild-type, alleles, variants, mutations or fragments of the genes. Mutations and alleles of the receptor genes are also preferably used in the construction of a vector for use in treatment. The vector comprising the desired nucleic acid sequence expressing a gene of interest, preferably has at least one such nucleic acid sequence. Alternatively, the vector may be comprised of more than one such nucleic acid sequence, or combinations of allelic variants. The vector can also be comprised of cassettes of different allelic variants or wild type genes.

Introducing the genes, fragments or variants thereof, into an individual can include use of vectors, liposomes, naked DNA, adjuvant-assisted DNA, gene gun, catheters, etc. Vectors include chemical conjugates such as described in WO 93/04701, which has a targeting moiety (e.g. a ligand to a cellular surface receptor), and a nucleic acid binding moiety (e.g. polylysine), viral vector (e.g. a DNA or RNA viral vector), fusion proteins such as described in PCT/US95/02140 (WO 95/22618) which is a fusion protein containing a target moiety (e.g. an antibody specific for a target cell) and a nucleic acid binding moiety (e.g. a protamine), plasmids, phage etc. The vectors can be chromosomal, non-chromosomal or synthetic.

Preferred vectors include viral vectors, fusion proteins and chemical conjugates. Retroviral vectors include Moloney murine leukemia viruses. DNA viral vectors are preferred. Viral vectors can be chosen to introduce the genes to cells of choice. Such vectors include pox vectors such as orthopox or avipox vectors, herpesvirus vectors such as herpes simplex I virus (HSV) vector (Geller et al., 1995, *J. Neurochem.* 64: 487; Lim et al., 1995, in *DNA Cloning: Mammalian Systems*, D. Glover, ed., Oxford Univ. Press, Oxford, England; Geller et al., 1990, Proc. Natl. Acad. Sci. U.S.A. 87: 1149), adenovirus vectors (LeGal LaSalle et al., 1993, *Science* 259: 988; Davidson et al., 1993, *Nat. Genet.* 3: 219; Yang et al., 1995, *J. Virol.* 69: 2004) and adeno-associated virus vectors (Kaplitt et al., 1994, *Nat. Genet.* 8: 148).

Pox viral vectors introduce the gene into the cells cytoplasm. Avipox virus vectors result in only short term expression of the nucleic acid. Adenovirus vectors, adeno-associated virus vectors and herpes simplex virus vectors are preferred for introducing the nucleic acid into neural cells. The adenovirus vector results in a shorter term expression (about 2 months) than adeno-associated virus (about 4 months), which in turn is shorter than HSV vectors. The vectors can be introduced by standard techniques, e.g. infection, transfection, transduction or transformation. Examples of modes of gene transfer include for example, naked DNA calcium phosphate precipitation, DEAE dextran, electroporation, protoplast fusion, lipofection, cell microinjection and viral vectors.

The vector can be employed to target essentially any desired target cell. For example, stereotaxic injection can be used to direct the vectors (e.g. Adeno-associated virus, adenovirus, HSV) to a desired location. Other methods that can be used include catheters, intravenous, parenteral, parenteral, intraperitoneal, and subcutaneous injection, and oral or other known routes of administration.

Another preferred method is DNA immunization. DNA immunization employs the subcutaneous injection of a plasmid DNA (pDNA) vector encoding a specific Receptor protein and/or ligands, such as for example, receptorrin A1. The pDNA sequence is taken up by antigen presenting cells (APC). Once inside the cell, the DNA encoding protein is transcribed and translated. Genetic constructs comprise a nucleotide sequence that encodes the nucleic acid sequence of choice and preferably includes an intracellular trafficking sequence operably linked to regulatory elements needed for gene expression.

When taken up by a cell, the genetic construct(s) may remain present in the cell as a functioning extrachromosomal molecule and/or integrate into the cell's chromosomal DNA. DNA may be introduced into cells where it remains as separate genetic material in the form of a plasmid or plasmids. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the genetic construct as a linear minichromosome including a centromere, telomeres and an origin of replication. Gene constructs may remain part of the genetic material in attenuated live microorganisms or recombinant microbial vectors which live in cells. Gene constructs may be part of genomes of recombinant viral vaccines where the genetic material either integrates into the chromosome of the cell or remains extrachromosomal.

Genetic constructs include regulatory elements necessary for gene expression of a nucleic acid molecule. The elements include: a promoter, an initiation codon, a stop codon, and a polyadenylation signal. In addition, enhancers may be required for gene expression of the sequence of choice, for example, the Receptor gene, variants or fragments thereof. It is necessary that these elements be operably linked to the sequence that encodes the desired proteins and that the regulatory elements are operable in the individual to whom they are administered.

Initiation codons and stop codons are generally considered to be part of a nucleotide sequence that encodes the immunogenic target protein. However, it is necessary that these elements are functional in the individual to whom the gene construct is administered. The initiation and termination codons must be in frame with the coding sequence.

Promoters and polyadenylation signals used must be functional within the cells of the individual. Examples of promoters useful to practice the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metallothionein. Examples of polyadenylation signals useful to practice the present invention, especially in the production of a genetic vaccine for humans, include but are not limited to SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, is used.

In addition to the regulatory elements required for DNA expression, other elements may also be included in the DNA molecule. Such additional elements include enhancers. The enhancer may be selected from the group including but not limited to: human Actin, human Myosin, human Hemoglobin, human muscle creatine and viral enhancers such as those from CMV, RSV and EBV.

Genetic constructs can be provided with mammalian origin of replication in order to maintain the construct extrachromosomally and produce multiple copies of the construct in the cell. For example, plasmids pCEP4 and pREP4 from Invitrogen (San Diego, Calif.) contain the Epstein Barr virus origin of replication and nuclear antigen EBNA-1 coding region which produces high copy episomal replication without integration.

In order to maximize protein production, regulatory sequences may be selected which are well suited for gene expression in the cells the construct is administered into. Moreover, codons may be selected which are most efficiently transcribed in the cell. One having ordinary skill in the art can produce DNA constructs which are functional in the cells.

The method of the present invention comprises the steps of administering cells comprising exogenous nucleic acid molecules to tissue of the individual.

In some embodiments, the nucleic acid molecule is delivered to the cells in conjunction with administration of a facilitating agent. Facilitating agents are also referred to as polynucleotide function enhancers or genetic vaccine facilitator agents. Facilitating agents are described in e.g. International Application No. PCT/US94/00899 filed Jan. 26, 1994 and International Application No. PCT/US95/04071 filed Mar. 30, 1995, both incorporated herein by reference. Facilitating agents which are administered in conjunction with nucleic acid molecules may be administered as a mixture with the nucleic acid molecule or administered separately simultaneously, before or after administration of nucleic acid molecules.

In some preferred embodiments, the genetic constructs of the invention are formulated with or administered in conjunction with a facilitator selected from the group consisting of, for example, benzoic acid esters, anilides, amidines, urethans and the hydrochloride salts thereof such as those of the family of local anesthetics. The facilitating agent is administered prior to, simultaneously with or subsequent to the genetic construct. The facilitating agent and the genetic construct may be formulated in the same composition.

In some embodiments, the genetic constructs are administered free of facilitating agents, that is in formulations free from facilitating agents using administration protocols in which the genetic constructions are not administered in conjunction with the administration of facilitating agents.

Nucleic acid molecules which are delivered to cells according to the invention may serve as genetic templates for proteins that function as prophylactic and/or therapeutic immunizing agents. In preferred embodiments, the nucleic acid molecules comprise the necessary regulatory sequences for transcription and translation of the coding region in the cells of the animal.

Additionally, the nucleic acid sequences of choice can be mutated in vitro or in vivo, to create and/or destroy translation, initiation, and/or termination sequences, or to create variations in coding regions and/or form new restriction endonuclease sites or destroy preexisting ones, to facilitate further in vitro modification. Any technique for mutagenesis known in the art can be used, including but not limited to, in vitro site-directed mutagenesis (Hutchinson et al., 1978, *J. Biol. Chem.* 253: 6551; Zoller and Smith, 1984, *DNA* 3:479-488; Oliphant et al., 1986, *Gene* 44: 177; Hutchinson et al., 1986, *Proc. Natl. Acad. Sci. U.S.A.* 83: 710; and others). PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61-70).

Various methods known to those skilled in the art can be used to express nucleic acid sequences in the non-immortalized cells. For example, the identified and isolated gene can be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, AAV (e.g., AAV5), *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector that has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharo*- myces cerevisiae by linking sequences from an *E. coli* plasmid with sequences from the yeast 2µ plasmid.

In an alternative method, the desired gene may be identified and isolated after insertion into a suitable cloning vector in a "shot gun" approach. Enrichment for the desired gene, for example, by size fractionation, removal of highly-repetitive sequences, subtractive or otherwise selective hybridization, and other methods as may be known in the art, can be done before insertion into the cloning vector.

The nucleotide sequence can be inserted into an appropriate expression vector, i.e., a vector which contains the necessary elements for the transcription and translation of the inserted protein-coding sequence. Such elements are termed herein a "promoter." Thus, the nucleic acid encoding a desired protein, functional fragments, derivatives or analogs thereof, is operationally associated with a promoter in an expression vector of the invention. Both cDNA and genomic sequences can be cloned and expressed under control of such regulatory sequences. An expression vector also preferably includes a replication origin. The necessary transcriptional and translational signals can be provided on a recombinant expression vector.

Potential host-vector systems include but are not limited to mammalian cell systems infected with virus (e.g., vaccinia virus, adenovirus, AAV, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant protein, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding a protein, peptide, or fragments thereof, is cultured in an appropriate cell culture medium under conditions that provide for expression of the protein by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of proteins, may be controlled by any promoter/enhancer element known in the art, but these regulatory elements must be functional in the host selected for expression. Expression vectors containing a nucleic acid encoding a desired polypeptide, can be detected or identified by four general approaches: (a) PCR amplification of the desired plasmid DNA or specific mRNA, (b) nucleic acid hybridization, (c) presence or absence of selection marker gene functions, and (d) expression of inserted sequences. In the first approach, the nucleic acids can be amplified by PCR to provide for detection of the amplified product. In the second approach, the presence of a foreign gene inserted in an expression vector can be detected by nucleic acid hybridization using probes comprising sequences that are homologous to an inserted marker gene. In the third approach, the recombinant vector/host system can be identified and selected based upon the presence or absence of certain "selection marker" gene functions (e.g., β-galactosidase activity, thymidine kinase activity, resistance to antibiotics, transformation phenotype, occlusion body formation in baculovirus, etc.) caused by the insertion of foreign genes in the vector. In another example, if the nucleic acid a desired polypeptide is inserted within the "selection marker" gene sequence of the vector, recombinants containing the protein insert can be identified by the absence of the gene function.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *E. coli* plasmids col E1, pCR1, pBR322, pMal-C2, pET, pGEX (Smith et al., 1988, *Gene* 67: 31-40), pMB9 and their derivatives, plasmids such as RP4; phage DNAS, e.g., the numerous derivatives of λ phage, e.g., NM989, and other phage DNA, e.g., M13 and filamentous single stranded phage DNA; yeast plasmids such as the 2µ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

For example, in a baculovirus expression systems, both non-fusion transfer vectors, such as but not limited to pVL941 (BamH1 cloning site; Summers), pVL1393 (BamH1, SmaI, XbaL EcoRI, NotI, XmaIII, BglII, and PstI cloning site; Invitrogen), pVL1392 (BglII, PstI, Nod, XmaIII, EcoRI, XbaI, SmaI, and BamH1 cloning site; Summers and Invitrogen), and pBlueBacIII (BamH1, BglII, PstI, NcoI, and HindIII cloning site, with blue/white recombinant screening possible; Invitrogen), and fusion transfer vectors, such as but not limited to pAc700 (BamH1 and KpnI cloning site, in which the BamH1 recognition site begins with the initiation codon; Summers), pAc701 and pAc702 (same as pAc700, with different reading frames), pAc360 (BamH1 cloning site 36 base pairs downstream of a polyhedron initiation codon; Invitrogen(195)), and pBlueBacHisA, B, C (three different reading frames, with BamH1, BglII, PstI, NcoI, and HindIII cloning site, an N-terminal peptide for ProBond purification, and blue/white recombinant screening of plaques; Invitrogen (220)) can be used.

Mammalian expression vectors contemplated for use in the invention include vectors with inducible promoters, such as the dihydrofolate reductase (DHFR) promoter, e.g., any expression vector with a DHFR expression vector, or a DHFR/methotrexate co-amplification vector, such as pED (PstI, SalI, SbaI, SmaI, and EcoRI cloning site, with the vector expressing both the cloned gene and DHFR; see Kaufman, Current Protocols in Molecular Biology, 16.12 (1991). Alternatively, a glutamine synthetase/methionine sulfoximine co-amplification vector, such as pEE14 (HindIII, XbaI, SmaI, SbaI, EcoRI, and Bell cloning site, in which the vector expresses glutamine synthase and the cloned gene; Celltech). In another embodiment, a vector that directs episomal expression under control of Epstein Barr Virus (EBV) can be used, such as pREP4 (BamHI, SfiI, XhoI, NotI, NheI, HindIII, NheI, PvuII, and KpnI cloning site, constitutive RSV-LTR promoter, hygromycin selectable marker; Invitrogen), pCEP4 (BamH1, SfiI, XhoI, NotI, NheI, HindIII, NheI, PvuII, and KpnI cloning site, constitutive hCMV immediate early gene, hygromycin selectable marker; Invitrogen), pMEP4 (KpnI, PvuI, NheI, HindIII, NotI, XhoI, SfiI, BamH1 cloning site, inducible methallothionein IIa gene promoter, hygromycin selectable marker: Invitrogen), pREP8 (BamHI, XhoI, NotI, HindIII, NheI, and KpnI cloning site, RSV-LTR promoter, histidinol selectable marker; Invitrogen), pREP9 (KpnI, NheI, HindIII, NotI, XhoI, SfiI, and BamHI cloning site, RSV-LTR promoter, G418 selectable marker; Invitrogen), and pEBVHis (RSV-LTR promoter, hygromycin selectable marker, N-terminal peptide purifiable via ProBond resin and cleaved by enterokinase; Invitrogen). Selectable mammalian expression vectors for use in the invention include pRc/CMV (HindIII, BstXI, NotI, SbaI, and ApaI cloning site, G418 selection; Invitrogen), pRc/RSV (HindIII, SpeI, BstXI, NotI, XbaI cloning site, G418 selection; Invitrogen), and others. Vaccinia virus mammalian expression vectors (see, Kaufman, 1991, supra) for use according to the invention include but are not limited to pSC11 (Sural cloning site, TK- and β-gal selection), pMJ601 (SalI, SmaI, AflI, NatI, BspMII, BamHI, ApaI, NheI, SacH, KpnI, and HindIII cloning site; TK- and β-gal selection), and pTKgptF1S (EcoRI, PstI, SalI, AccI, HindIII, SbaI, BamHI, and Hpa cloning site, TK or XPRT selection).

Yeast expression systems can also be used according to the invention to express polypeptides. For example, the non-fusion pYES2 vector (XbaI, SphI, ShoI, NotI, GstXI, EcoRI, BstXI, BamHI, SacI, KpnI, and HindIII cloning sit; Invitrogen) or the fusion pYESHisA, B, C (XbaI, SphI, ShoI, NotI, BstXI, EcoRI, BamH1, SacI, KpnI, and HindIII cloning site, N-terminal peptide purified with ProBond resin and cleaved with enterokinase; Invitrogen), to mention just two, can be employed according to the present invention.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

A preferred vector for the present invention is a Adeno-Associated virus vector, such as, for example AAV5.

Another preferred method is using the above-described vectors, or other vectors well known in the art, for introducing vectors into cells or tissues which are equally suitable for use in vivo, in vitro, and ex vivo. For ex vivo therapy, vectors may be introduced into stem cells taken from the patient and clonally propagated for autologous transplant back into that same patient. Macrophages also can be employed. Delivery by transfection, by liposome injections, or by polycationic amino polymers may be achieved using methods which are well known in the art (see, e.g., Goldman et al., 1997, *Nature Biotechnology* 15: 462-466).

Any of the therapeutic methods described above may be applied to any subject in need of such therapy, including, for example, mammals such as livestock such as sheep, goats, cattle and horses; pets such as dogs, cats and rabbits; preferably, primates such as monkeys; and, most preferably, humans.

In all embodiments of the DNA construct, exogenous DNA can encode one or more products, can be one or more therapeutic products or one or more of each, thus making it possible to deliver multiple products.

Replacement of a Regulatory Sequence of a Gene by Homologous Recombination

Gene targeting can be used to replace a gene's existing regulatory region with a regulatory sequence isolated from a different gene or a novel regulatory sequence synthesized by genetic engineering methods. Such regulatory sequences may comprise promoters, enhancers, Scaffold-attachment regions, negative regulatory elements, transcriptional initiation sites, regulatory protein binding sites or combinations of said sequences. (Alternatively, sequences which affect the structure or stability of the RNA or protein produced may be replaced, removed, added, or otherwise modified by targeting, including polyadenylation signals, mRNA stability elements, splice sites, leader sequences for enhancing or modifying transport or secretion properties of the protein, or other sequences which alter or improve the function or stability of protein or RNA molecules).

Several embodiments are possible. First, the targeting event may be a simple insertion of the regulatory sequence, placing the gene under the control of the new regulatory sequence (for example, inserting a new promoter or enhancer or both upstream of a gene). Second, the targeting event may be a simple deletion of a regulatory element, such as the deletion of a tissue-specific negative regulatory element. Third, the targeting event may replace an existing element; for example, a tissue-specific enhancer can be replaced by an enhancer that has broader or different cell-type specificity than the naturally-occurring elements. In this embodiment the naturally occurring sequences are deleted and new sequences are added. In all cases, the identification of the targeting event may be facilitated by the use of one or more selectable marker genes that are contiguous with the targeting DNA, allowing for the selection of cells in which the exogenous DNA has integrated into the host cell genome. The identification of the targeting event may also be facilitated by the use of one or more marker genes exhibiting the property of negative selection, such that the negatively selectable marker is linked to the exogenous DNA, but configured such that the negatively selectable marker flanks the targeting sequence, and such that a correct homologous recombination event with sequences in the host cell genome does not result in the stable integration of the negatively selectable marker. Markers useful for this purpose include the Herpes Simplex Virus thymidine kinase (TK) gene or the bacterial xanthine-guanine phosphoribosyltransferase (gpt) gene.

Transfection of Primary Cells and Production of Clonal or Heterogeneous Cell Strains Any method known in the art can be used to transfect the cells isolated from primary tissue. Vertebrate tissue is first obtained; this is carried out using known procedures, such as biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

In a preferred embodiment, cells from regionally specific tissue for long-term culture, such as for example, the antero-lateral temporal lobe neocortex is removed from patients undergoing temporal resection associated with medically intractable epilepsy. Tissue is microdissected into regions containing hippocampus or temporal cortex gray matter and triturated to single cells and maintained as a monolayer on uncoated plastic dishes throughout culture in defined proliferative media, modified from a standard protocol for the culture of neural stem cells 17. Growth media comprises Dulbecco's Modified Eagle Medium with nutrient mix F-12 (DMEM/F-12) containing N2 supplements, fetal bovine serum, antibiotics, bovine pituitary extract, epidermal growth factor (EGF) and basic fibroblast growth factor (FGF).

To identify cultured cell types, primary cells are examined for expression of immunotypic markers throughout culture. Following explanation, immunocytochemistry on primary cells 3 days in vitro (DIV) revealed a heterogeneous population containing predominantly astrotypic (GFAP⁺) cells.

The resulting primary cell mixture can be transfected directly or it can be cultured first, removed from the culture plate and resuspended before transfection is carried out. Primary cells can be combined with exogenous DNA to be stably integrated into their genomes and, optionally, DNA encoding a selectable marker, and treated in order to accomplish transfection. The exogenous DNA and selectable marker-encoding DNA can each be on a separate construct (e.g., pXGH5 and pcDNEO) or on a single construct (e.g., pXGH301) and an appropriate quantity of DNA to ensure that at least one stably transfected cell containing and appropriately expressing exogenous DNA is produced. In general, about 0.1 to up to 500 µg DNA is used.

In one embodiment a method of producing transfected primary cells, is effected by electroporation. Electroporation is carried out at appropriate voltage and capacitance (and corresponding time constant) to result in entry of the DNA construct(s) into the primary cells. Electroporation can be carried out over a wide range of voltages (e.g., 50 to 2000 volts) and corresponding capacitance. Electroporation is very efficient if carried out at an electroporation voltage in the range of about 250-300 volts and a capacitance of 960 µFarads. Total DNA of about 0.1 to 500 82 g is generally used. Total DNA of about 60 µg and voltage of about 250-300 volts with capacitance of about 960 µFarads for a time constant about 14-20 of msec can be used.

In another embodiment, primary cells are transfected using microinjection. Alternatively, known methods such as calcium phosphate precipitation, modified calcium phosphate precipitation and polybrene precipitation, liposome fusion and receptor-mediated gene delivery can be used to transfect cells. A stably transfected cell is isolated and cultured and sub-cultivated, under culturing conditions and for sufficient time, to propagate the stably transfected secondary cells and produce a clonal cell strain of transfected secondary cells. Alternatively, more than one transfected cell is cultured and sub-cultivated, resulting in production of a heterogeneous cell strain.

Transfected primary cells undergo a sufficient number of cell divisions to produce either a clonal cell strain or, if desired, a heterogeneous cell strain of sufficient size to provide the therapeutic product to an individual in effective amounts. The number of required cells in a transfected clonal or heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

Implantation of Clonal Cell Strains or Heterogeneous Cell Strains of Transfected Secondary Cells The homologous recombinant cells produced can be introduced into an individual to whom the therapeutic product is to be delivered, using known methods. The clonal cell strain or heterogeneous cell strain is introduced into an individual, using known methods, using various routes of administration and at various sites (e.g., renal subcapsular, subcutaneous, central nervous system (including intrathecal), intravascular, intrahepatic, intrasplachnic, intraperitoneal (including intraomental), or intramuscular implantation). Once implanted in the individual, the transfected cells produce the therapeutic product encoded by the exogenous DNA or are affected by the exogenous DNA itself. Based on the age, weight, and clinical condition of the patient, the required number of cells are grown in large-scale culture. The entire process would require about 4-6 weeks and, at the end of that time, the appropriate number of genetically-engineered cells are introduced into the individual.

The cells used will generally be patient-specific genetically-engineered cells. It is possible, however, to obtain cells from another individual of the same species or from a different species. Use of such cells might require administration of an immunosuppressant, alteration of histocompatibility antigens, or use of a barrier device to prevent rejection of the implanted cells. For many diseases, this will be a one-time treatment and, for others, multiple therapy treatments will be required.

Uses of Homologously Recombinant Primary Cells and Cell Strains

The primary cells or cell strains have wide applicability as a vehicle or delivery system for therapeutic products, such as enzymes, hormones, cytokines, antigens, antibodies, clotting factors, anti-sense RNA, regulatory proteins, transcription proteins, receptors, structural proteins, ribozymes, novel (non-naturally occurring) proteins and nucleic acid products, and engineered DNA. For example, transfected primary cells can be used to supply a therapeutic protein, including, but not limited to, Factor VIII, Factor IX, erythropoietin, alpha-1 antitrypsin, calcitonin, glucocerebrosidase, growth hormone, low density lipoprotein (LDL) receptor, IL-2 receptor and its antagonists, insulin, globin, immunoglobulins, catalytic antibodies, the interleukins, insulin-like growth factors, superoxide dismutase, immune responder modifiers, parathyroid hormone, interferons, nerve growth factors, tissue plasminogen activators, and colony stimulating factors. Alternatively, transfected primary cells can be used to immunize an individual (i.e., as a vaccine). In the case where targeting is utilized to introduce additional DNA sequences into the genome, the ability to pre-select the integration site offers many advantages as compared to random integration. For example, the additional sequences can be directed to a region of the genome that allows appropriate expression and to regions that are distant from oncogenes. The sequences can be targeted to non-essential or essential genes or to non-coding sequences as desired. The choice of site can be determined based on the above considerations or based on known integration sites of well-characterized, appropriately-functioning transfected cells. The wide variety of uses of cells of the present invention can perhaps most conveniently be summarized as shown below. The cells can be used to deliver the following therapeutic products: (1) a secreted protein with predominantly systemic effects; (2) a secreted protein with predominantly local effects; (3) a membrane protein imparting new or enhanced cellular responsiveness; (4) membrane protein facilitating removal of a toxic product; (5) a membrane protein marking or targeting a cell; (6) an intracellular protein; (7) an intracellular protein directly affecting gene expression; (8) an intracellular protein with autolytic effects; (9) gene product-engineered DNA which binds to or sequesters a regulatory protein; (10) a ribozyme; (11) antisense-engineered RNA to inhibit gene expression.

The transfected primary and/or secondary cells can be used to administer therapeutic proteins (e.g., hormones, enzymes, clotting factors) which are presently administered intravenously, intramuscularly or subcutaneously, which requires patient cooperation and, often, medical staff participation. When transfected primary cells are used, there is no need for extensive purification of the polypeptide before it is administered to an individual, as is generally necessary with an isolated polypeptide. In addition, transfected primary cells of the present invention produce the therapeutic product as it would normally be produced.

An advantage to the use of transfected primary cells of the present invention is that by controlling the number of cells introduced into an individual, one can control the amount of the product delivered to the body. In addition, in some cases, it is possible to remove the transfected cells if there is no longer a need for the product. A further advantage of treatment by use of transfected primary cells is that production of the therapeutic product can be regulated, such as through the administration of zinc, steroids or an agent which affects translation or transcription of a protein product or nucleic acid product or affects the stability of a nucleic acid product.

Treatment of Neurological Disorders

In one embodiment, the present invention provides a method of treating a patient suffering from a neurological disorder, such as a central nervous system disorder, or alleviating the symptoms of such a disorder, by administering cells cultured according to the method of the invention to the patient's brain. As used herein, the terms "treating" and "treatment" refer to curative therapy, prophylactic therapy, and preventative therapy. The term "therapy" as used herein, refers to therapeutic methods for reducing or eliminating the symptoms of the particular disorder for which treatment is sought. The term "patient" as used herein generally refers to any warm blooded mammal, such as humans, non-human primates, rodents and the like which is to be the recipient of the particular treatment. Examples of neurological disorders include Parkinson's disease, Huntington's disease, Alzheimer's disease, severe seizure disorders including epilepsy, familial dysautonomia as well as injury or trauma to the nervous system, such as neurotoxic injury or disorders of mood and behavior such as addiction and schizophrenia.

In this method of the invention, primary cells and if desired precursor cells are cultured in vitro as described above to form differentiated neuronal cells which are then transplanted into the brain of a patient in need thereof.

In a preferred embodiment, the non-immortalized long-term proliferating cells express a heterologous nucleic acid sequences which overexpress neurotrophic and/or neuroprotective factors in affected nigrostriatal cells.

In another preferred embodiment, the non-immortalized long-term proliferating cells are a durable neural cell population that can be engineered into a variety of cell types by expressing desired molecules, such as for example, neurotransmitters, neurotrophic factors, enzymes, peptides and the like. Preferably, these cells are introduced into a patient in need of therapy, such as a patient suffering from or susceptible to neural disorders, using minimally invasive techniques as described infra.

Cells are suspended in a physiologically compatible carrier. As used herein, the term "physiologically compatible carrier" refers to a carrier that is compatible with the other ingredients of the formulation and not deleterious to the recipient thereof. Those of skill in the art are familiar with physiologically compatible carriers. Examples of suitable carriers include cell culture medium (e.g., Eagle's minimal essential media), phosphate buffered saline, and Hank's balanced salt solution±glucose (HBSS).

The volume of cell suspension administered to a patient will vary depending on the site of implantation, treatment goal and amount of cells in solution. Typically the amount of cells administered to a patient will be a "therapeutically effective amount." As used herein, a therapeutically effective amount refers to the number of transplanted cells which are required to effect treatment of the particular disorder. For example, where the treatment is for Parkinson's disease, transplantation of a therapeutically effective amount of cells will typically produce a reduction in the amount and/or severity of the symptoms associated with that disorder, e.g., rigidity, akinesia and gait disorder.

It is estimated that a severe Parkinson's patient will need at least about 100,000 surviving dopamine cells per grafted side to have a substantial beneficial effect from the transplantation. As cell survival is low in brain tissue transplantation in general (5-10%) an estimated 1-4 million dopaminergic neurons should be transplanted. For a successful therapy about $5 \times 10^6 - 1 \times 10^8$ cells should be transplanted per patient side. The cells are collected together and then loaded directly into a stereotactic needle. Cells do not need any special formulation if total duration of the implantation procedure is less than 1 hour. Preferentially, the prepared spheres are maintained in medium and will be loaded into the needle immediately before introducing the needle into the patients brain.

The cells, useful for treating neural disorders comprise a DNA molecule, such as an AAV vector, lentiviral vector, to a target cell in the brain or nervous system of the mammal.

The DNA molecule may comprise a 3' flanking region which will stabilize the transcript made by the molecule and terminate transcription coming from the molecule, located 3' to the gene to be expressed. See for example, Moreira, A. et al., *EMBO J.*, 14, 3809 (1995). The 3' flanking region contains a transcription terminator and stabilizing elements such as a polyA region. Therefore, the 3' flanking region will be located where the transcript will terminate. The preferred 3' flanking sequences include the 3' flanking regions from the genes encoding β-galactosidase, SV40, β-globin, α-globin, and human growth hormone.

The preferred promoter elements include promoters from the genes encoding: myosin heavy chain α, myosin heavy chain β, insulin, somatostatin, glucagon, growth associated protein 43 kDa, superior cervical ganglion clone 10, neurofilament-L, neurofilament-M, neurofilament-H, glial bifilary protein, P0, myelin associated glycoprotein, myelin basic protein, calcitonin-gene related peptide, and a neuron specific enolase. The most preferred promoter element is a neuron specific enolase promoter. Preferred recombinase sites include FRT and LoxP sites. Preferred terminators include transcription terminators for gastrin, C2 complement, and β-globin.

This approach has broad application to the regulation of numerous genes. In particular this application is useful for creating and studying discrete modifications in genes where the spatial and temporal expression of the gene is important. Therefore, the genes to be controlled will include genes expressing regulatory factors, signal transducers, and developmental factors.

Although any gene may be used, the preferred genes whose expression is to be controlled includes genes expressing hormones, hormone receptors, neurotransmitters, neurotrophic factors, neurotrophic factor receptors, neuronal peptides, cell signaling molecules, and receptors for any of these peptides. The most preferred genes whose expression is to be controlled includes genes expressing neuronal growth factors.

Cells transduced with a vector expressing the peptide of choice can be analyzed by any method known in the art. All of these principles may be applied independently, in combination, or in combination with other known methods of sequence identification. Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today,* 2000, 5, 415-425), READS (restriction enzyme amplification of digested cDNAs) (Prashar and Weissman, *Methods Enzymol.,* 1999, 303, 258-72), TOGA (total gene expression analysis) (Sutcliffe, et al., *Proc. Natl. Acad. Sci. U.S.A.,* 2000, 97, 1976-81), protein arrays and proteomies (Celis, et al., *FEBS Lett.,* 2000, 480, 2-16; Jungblut, et al., *Electrophoresis,* 1999, 20, 2100-10), expressed sequence tag (EST) sequencing (Celis, et al., *FEBS Lett.,* 2000, 480, 2-16; Larsson, et al., *J. Biotechnol.,* 2000, 80, 143-57), subtractive RNA fingerprinting (SuRF) (Fuchs, et al., *Anal. Biochem.,* 2000, 286, 91-98; Larson, et al., *Cytometry,* 2000, 41, 203-208), subtractive cloning, differential display (DD) (Jurecic and Belmont, *Curr. Opin. Microbiol.,* 2000, 3, 316-21), comparative genomic hybridization (Carulli, et al., *J. Cell Biochem. Suppl.,* 1998, 31, 286-96), FISH (fluorescent in situ hybridization) techniques (Going and Gusterson, *Eur. J. Cancer,* 1999, 35, 1895-904) and mass spectrometry methods (reviewed in (To et al., *Comb. Chem. High Throughput Screen,* 2000, 3, 235-41).

Although any gene may be used, preferred genes includes genes expressing hormones, hormone receptors, neurotransmitters, neurotrophic factors, neurotrophic factor receptors, neuronal peptides, cell signaling molecules, and receptors for any of these peptides. Preferred genes whose expression is to be controlled includes genes expressing neuronal growth factors.

Useful vectors include viral and plasmid vectors. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

Recombinant genes may also be introduced into viruses, such as AAV, adenoviruses, lentivirus, vaccina virus. Recombinant viruses can be generated by transfection of plasmids into cells infected with virus. Suitable vectors include, but are not limited to, lambda vector systems gt11, gt WES, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference), pQE, pIH821, pGEX, pET series (see F. W. Studier et al., "Use of T7 RNA Polymerase to Direct Expression of Cloned Genes," Gene Expression Technology vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., Molecular Cloning: A Laboratory Manual, Cold Springs Laboratory, Cold Springs Harbor, N.Y. (1982), which is hereby incorporated by reference.

According to the invention, a variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., lentivirus, vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used. Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promoted mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosomes. For a review of maximizing gene expression, see Roberts and Lauer, Methods in Enzymology, 68:473 (1979), which is hereby incorporated by reference.

The present invention also includes any host cells carrying the recombinatorial substrate. Host cells include bacterial or animal cells, which may be used to maintain or propagate the recombinatorial substrate. Host cells also encompass mammalian cells which have been transformed with the recombinatorial substrate.

A preferred approach is to introduce a nucleic acid coding for the recombinase through the use of viral vectors. The preferred vectors include Adenovirus ("Ad") (Akli S. et al., *Nat. Genet.* 3, 224 (1993); Bajocchi, G. et al., *Nat. Genet.,* 3, 229 (1993); Davidson, B., et al., *Nat. Genet.,* 3, 219, (1993); Le Gal La Salle, G. et al., *Science,* 259, 988 (1993), adeno-associated virus ("AAV") (Kaplitt, M. et al., *Nat. Genet.,* 8, 148 (1994a), and Herpes Simplex Virus ("HSV") (Dobson, A., Margolis, T. P., Sedarati, F., Stevens, J. and Feldman, L., Neuron, 5, 353 (1990); Federoff, H., Geller, A. and Lu, B., *Soc. Neurosci Abstr.,* 16, 353 (1990); Fink, D. et al., Hum. Gene Ther., 4, 11, (1992); Geller, A., Curr. Opin. Gen. Dev., 3, 81 (1993); Geller, A. and Freese, A. *Proc. Natl. Acad. Sci. USA,* 87, 1149 (1990); Ho, D., Mocarski, E. and Sapoloski, R., *Proc. Natl. Acad. Sci. USA,* 90, 3655 (1993); Kaplitt, M. et al., *Mol. Cell. Neurosci.,* 2, 320 (1991), *Proc. Natl. Acad. Sci. USA,* 91, 8979 (1994b).

To satisfy the requirement for spatial and temporal control of gene expression, vectors should infections of the non-immortalized long-term proliferating cell culture and expressed in a predictable time course. Using a micropipette to deliver nanoliter quantities of virus directly to cell cultures produced regional infections. Analysis of gene product expression in such cultures showed that it was limited to the microapplication site. With this method, there is a linear relationship between the number of virions applied and the number of transduced cells (Casaccia-Bonnefil, P., et al., *J. Neurosci. Methods,* 50, 341 (1993).

For the present application, the term "retrovirus" includes: murine leukemia virus (MLV), human immunodeficiency virus (HIV), equine infectious anemia virus (EIAV), mouse mammary tumor virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et al ("Retroviruses" 1997 Cold Spring Harbor Laboratory Press Eds: J M Coffin, S M Hughes, H E Varmus pp 758-763). Lentiviruses also belong to the retrovirus family, but they can infect both dividing and non-dividing cells (Lewis et al (1992) *EMBO J.* 3053-3058).

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome. The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5'end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane. Retroviruses may also contain "additional" genes which code for proteins other than gag, poi and env. Examples of additional genes include in HIV, one or more of vif, vpr, vpx, vpu, tat, rev and nef. EIAV has, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

In a preferred embodiment, retroviral vector systems are used as a delivery system, inter alia, for the transfer of a nucleic acid sequence to one or more sites of interest. The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, 1992 *Curr Top Microbiol Immunol* 158: 1-24).

A recombinant retroviral vector particle is capable of transducing a recipient cell with a nucleic acid sequence of interest. Once within the cell the RNA genome from the vector particle is reverse transcribed into DNA and integrated into the DNA of the recipient cell. As used herein, the term "vector genome" refers to both to the RNA construct present in the retroviral vector particle and the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof which need not necessarily be obtained from a virus such as a lentivirus but instead could be derived therefrom. By way of example, the sequence may be prepared synthetically or by use of recombinant DNA techniques. Preferably the genome comprises a psi region (or an analogous component which is capable of causing encapsidation).

The viral vector genome is preferably "replication defective" by which the genome does not comprise sufficient genetic information alone to enable independent replication to produce infectious viral particles within the recipient cell. In a preferred embodiment, the genome lacks a functional env, gag or pol gene. The viral vector genome may comprise some or all of the long terminal repeats (LTRs). Preferably the genome comprises at least part of the LTRs or an analogous sequence which is capable of mediating proviral integration, and transcription. The sequence may also comprise or act as an enhancer-promoter sequence. The separate expression of the components required to produce a retroviral vector particle on separate DNA sequences cointroduced into the same cell will yield retroviral particles carrying defective retroviral genomes that carry therapeutic genes. This cell is referred to as the producer cell.

There are two common procedures for generating producer cells. In one, the sequences encoding retroviral gag, pol and env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome (having a psi region) is introduced into the packaging cell line, the helper proteins can package the psi-positive recombinant vector RNA to produce the recombinant virus stock. This can be used to transduce the nucleic acid sequence of interest into recipient cells. The recombinant virus whose genome lacks all genes required to make viral proteins can infect only once and cannot propagate. Hence, the nucleic acid sequence of interest is introduced into the host cell genome without the generation of potentially harmful retrovirus. A summary of the available packaging lines is presented in "Retroviruses" (1997 Cold Spring Harbor Laboratory Press Eds: J M Coffin, S M Hughes, H E Varmus pp 449).

The present invention also provides a packaging cell line comprising a viral vector genome of the first aspect of the invention. For example, the packaging cell line may be transduced with a viral vector system comprising the genome or transfected with a plasmid carrying a DNA construct capable of encoding the RNA genome. The present invention also provides a retroviral (or lentiviral) vector particle produced by such a cell. The second approach is to introduce the three different DNA sequences that are required to produce a retroviral vector particle i.e. the env coding sequences, the gag-pol coding sequence and the defective retroviral genome containing one or more nucleic acid sequences of interest into the cell at the same time by transient transfection, is referred to as transient triple transfection. Further components of the viral system which complement the vector genome may be present on one or more "producer plasmids" for transfecting into cells.

An example of a disease associated with a neural disorder is Parkinson's disease. Parkinson's disease (PD) is a neurodegenerative disorder characterized by the loss of the nigrostriatal pathway; a progressive disorder resulting from degeneration of dopaminergic neurons within the substantia nigra. Although the cause of Parkinson's disease is not known, it is associated with the progressive death of dopaminergic (tyrosine hydroxylase (TH) positive) mesencephalic neurons, inducing motor impairment. The characteristic symptoms of Parkinson's disease appear when up to 70% of TH-positive nigrostriatal neurons have degenerated.

Symptomatic treatment of the disease-associated motor impairments involves oral administration of dihydroxyphenylalanine (L-DOPA). L-DOPA is transported across the blood-brain barrier and converted to dopamine, partly by residual dopaminergic neurons, leading to a substantial improvement of motor function. However, after a few years, the degeneration of dopaminergic neurons progresses, the effects of L-DOPA are reduced and side-effects reappear. Better therapy for preventing, treating and/or curing Parkinson's disease and/or symptoms thereof is therefore necessary and desirable.

An alternative strategy for therapy is neural grafting. Without wishing to be bound by theory, dopamine supplied from cells implanted into the striatum would be able to substitute for lost nigrostriatal cells. Clinical trials have suggested that mesencephalic TH positive neurons obtained from human embryo cadavers (aborted fetuses) can survive and function in the brains of patients with Parkinson's disease. However, functional recovery has only been partial, and the efficacy and reproducibility of the procedure is limited. Some attempts have been made to use TH positive neurons from other species (in order to circumvent some of the ethical and practical problems). However, xenotransplantation requires immunosuppressive treatment and is also controversial due to, for example, the possible risk of cross-species transfer of infectious agents. In order to develop a practicable and effective transplantation protocol, an alternative source of TH positive neurons is required.

The main advantage of the invention is that the non-immortalized long-term replicating cell cultures are used for identifying compounds that are suitable for growth and maturation of cells for use in treatment of patients with neurodegenerative diseases. For example, cells are transduced with a vector system comprising a viral genome and a heterologous sequence encoding a protein/peptide of interest. Transduction with the vector system of the present invention may confer or increase the ability of the cell to produce catecholamines, confer or increase the ability of the cell to convert tyrosine to L-dopa and/or L-dopa to dopamine. Release of catecholamines can be measured by techniques known in the art, for example by using an electrochemical detector connected to an analytical cell. In addition to the catecholamines themselves, biproducts associated with catecholamine release (such as DOPAC, a specific degradation product of dopamine) may also be detected. The cell may be any cell which is susceptible to transduction. If the vector system is capable of transducing non-dividing cells (for example if it is a lentiviral system) then the cell may be a non-dividing cell such as a neuron.

In a preferred embodiment the transduced cell forms part of a genetically modified neuronal cell line. Such a cell line may, for example, be transplanted into the brain for the treatment of Parkinson's disease. In a further embodiment the cell is a cell in the striatum of a subject, such as a neuron or glial cell. Direct gene transfer in vivo to such a cell may, for example, convert it into a dopamine-producer cell.

A further alternative strategy for therapy is to replace dopamine in the affected striatum by introducing the enzymes responsible for L-DOPA or dopamine synthesis (for example, tyrosine hydroxylase); or introduce potential neuroprotective molecules that may either prevent the TH-positive neurons from dying or stimulate regeneration and functional recovery in the damaged nigrostriatal system (Dunnet S. B. and Bjorklund A. (1999) *Nature* 399 A32-A39).

In vivo, dopamine is synthesized from tyrosine by two enzymes, tyrosine hydroxylase (TH) and aromatic amino acid DOPA-decarboxylase (AADC). Parkinson's disease has been shown to be responsive to treatments that facilitate dopaminergic transmission in caudate-putamen. In experimental animals, genetically modified cells that express tyrosine hydroxylase, and thereby synthesize L-DOPA, induce behavioral recovery in rodent models of PD (Wolff et al. (1989) *PNAS* (USA) 86:9011-14; Freed et al (1990) *Arch. Neurol.* 47:505-12; Jiao et al. (1993) *Nature* 262:4505). However, the functional activity of tyrosine hydroxylase depends on the availability of its cofactor tetrahydrobiopterin ($BH_4$). The level of cofactor may be insufficient in the denervated striatum, and so it is thought that GTP cyclohydrolase I, the enzyme that catalyses the rate limiting step on the pathway of $BH_4$-synthesis, may also need to be transduced to obtain sufficient levels of L-DOPA production in vivo.

Accordingly, the present invention provides a system for growth of cells, cell grafting, testing of therapeutic candidate compounds, vectors expressing therapeutic peptides for the treatment of neurodegenerative disease in a mammal, e.g., Parkinson's disease. Further, the present invention provides a method for treating a neural disorder, such as neurodegenerative disease and/or symptoms thereof and/or preventing neurodegenerative disease and/or symptoms thereof, in a mammal, comprising, administering a vector to a target cell in the brain or nervous system of the mammal, the vector comprising a nucleic acid sequence comprising a sequence encoding a growth factor, advantageously in operable linkage with or operably linked to a promoter sequence, wherein said growth factor is expressed in the target cell, thereby treating said neurodegenerative disease.

Figure 7:
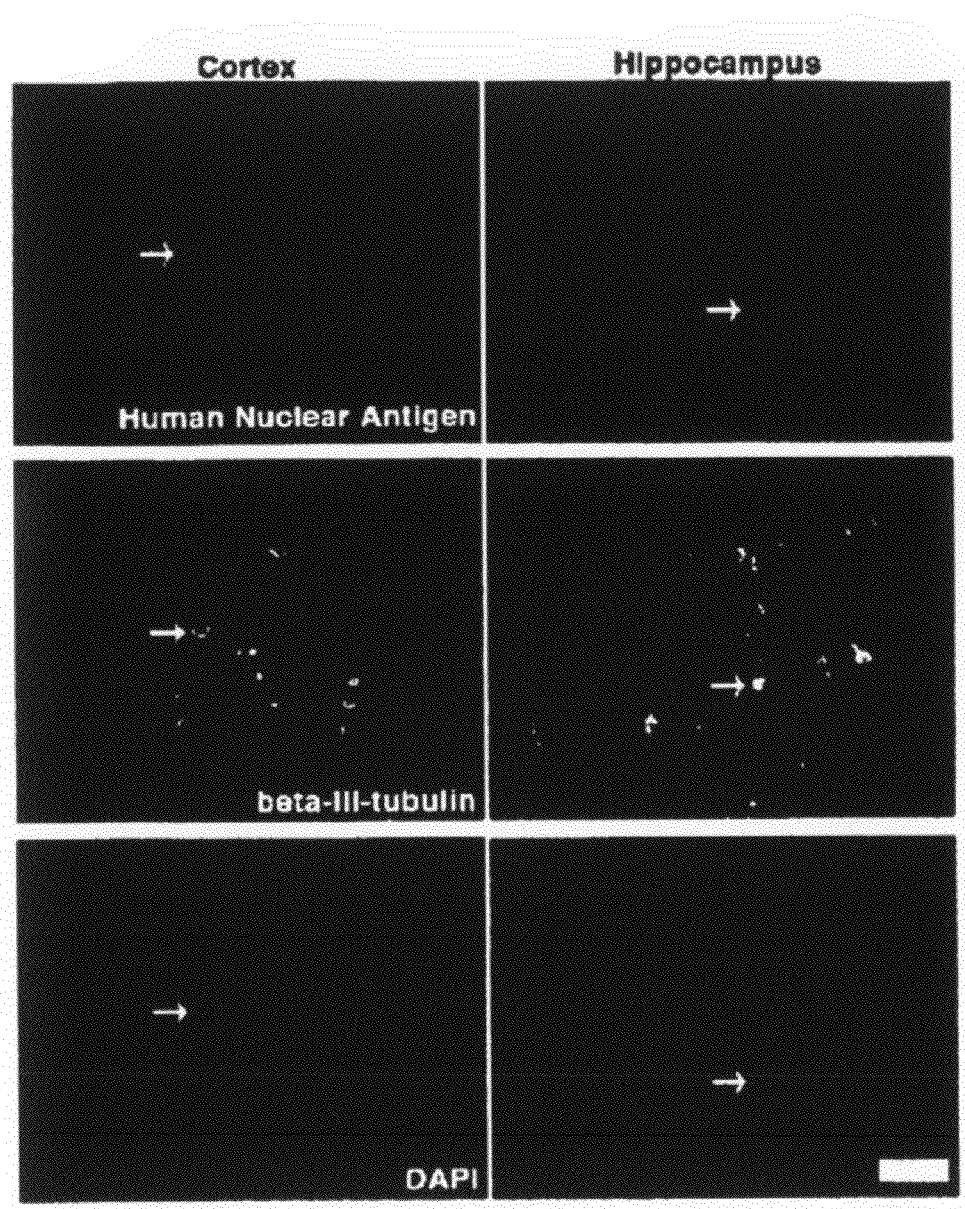
FIG. 7 is an immunofluorescent stain showing the transplantation of the cultured cells in vivo. Transplanted animals were allowed to survive a total of 30 days, and were then sacrificed and evaluated for engraftment of human cells. Integrating human cells were identified by both morphology (specifically increased size relative to host cells) and immunoreactivity for human nuclear antigen. Cells detected were primarily localized around the injection site, with the majority of cells remained in the cortex within 250 µm of the injection site (FIG. 7, left column). A small subset of cells were detected lateral to the site of cortical injection, suggesting human cells have a limited ability to undergo a tangential migration. Occasionally, cells were detected in other structures, including the hippocampus (FIG. 7, left column). Cells were immunophenotyped using antibody labeling. The majority of cells (>90%) appear to adopt neuronal morphologies and express the neuronal marker beta-III-tubulin.

In another preferred embodiment, the cells are transplanted into a patient in need of therapy, for example, a patient suffering from Alzheimer's disease, Parkinson's disease at the like. An example of such results are shown in the examples which follow. This is not meant to limit or construe the invention in any way but is offered for illustrative purposes. Briefly, $1 \times 10^5$ human neural progenitors were transplanted 1 mm right of the midline at a depth of 1 mm into the right cortex of adult NOD-SCID immunodeficient mice. Cells were suspended in phosphate buffered saline in a total fluid volume of 2 µl. Transplanted animals were allowed to survive a total of 30 days, and were then sacrificed and evaluated for engraftment of human cells. Integrating human cells were identified by both morphology (specifically increased size relative to host cells) and immunoreactivity for human nuclear antigen. Cells detected were primarily localized around the injection site, with the majority of cells remained in the cortex within 250 µm of the injection site (FIG. 7, left column). A small subset of cells were detected lateral to the site of cortical injection, suggesting human cells have a limited ability to undergo a tangential migration. Occasionally, cells were detected in other structures, including the hippocampus (FIG. 7, left column). Cells were immunophenotyped using antibody labeling. The majority of cells (>90%) appear to adopt neuronal morphologies and express the neuronal marker beta-III-tubulin. Occasional astrocytic phenotypes are detected, as are cells that do not express a mature phenotype.

The integration of these cells is interesting for several reasons: first, neuronal cell types are generally rare in transplants of adult progenitor populations. Second, the migration of these cells of distances up to 2 mm is an exceptional finding, suggesting that these cells may be useful for a number of transplant applications requiring long distance neuronal projections (i.e., Parkinson's disease). Third, as these progenitors are isolatable from multiple brain regions, it is likely that these cells could be gathered and expanded for this use using a minimally invasive technique, an advancement over current surgical interventions such as deep brain stimulation. Fourth, the ability of these cells to integrate over a period of 30 days is highly relevant, suggesting these cells may function as a transplant source that can stably integrate over a long period of time. Fifth, the generation of a preponderance of neuronal fates suggests that these cells may be useful as precursors for generating neuronal morphologies, a particularly difficult aspect of differentiating neural progenitors. Such populations may compete with the additional existing applications, including the use of more ethically and legally controversial embryonic and fetal tissue.

Similarly, the invention envisions polypeptides wherein amino acids are substituted on the basis of charge and/or structural similarities. That is, in determining suitable analogs, homologs, derivatives or variants of, for example, human GDNF, the skilled artisan, without undue experimentation, can consider replacing amino acids in therein with amino acids of similar charge and/or structure so as to obtain a variant, homolog, derivative or variant; and, from making such changes, the skilled artisan can derive a suitable nucleic acid molecule coding sequence for the variant, homolog, derivative, or variant of GDNF, without any undue experimentation. Thus, the skilled artisan can consider charge and/or structure of human GDNF sequences or portions thereof, in constructing homologs, variants, analogs and derivatives and nucleic acid molecules coding therefor, without undue experimentation.

One skilled in the art can obtain variants, homologs, analogs or derivatives of human nerve growth factors by PCR. For instance, by PCR amplification of a sample containing a human nerve growth factors, such as GDNF using a probe or primer or probes or primers that (each) can be any stretch of at least 8, preferably at least 10, more preferably at least 12, 13, 14, or 15, such as at least 20, e.g., at least 23 or 25, for instance at least 27 or 30 contiguous nucleotides in a human GDNF nucleic acid molecule (sequence) which are unique thereto. As to PCR or hybridization primers or probes and optimal lengths therefor, reference is also made to Kajimura et al., *GATA* 7(4):71-79 (1990).

In the brain, the basal ganglia consist of several pairs of nuclei, the two members of each pair being located in opposite cerebral hemispheres. The largest nucleus is the corpus striatum which consists of the caudate nucleus and the lentiform nucleus. Each lentiform nucleus is, in turn, subdivided into a lateral part called the putamen and a medial part called the globus pallidus. The substantia nigra and red nuclei of the midbrain and the subthalamic nuclei of the diencephalon are functionally linked to the basal ganglia. Axons from the substantia nigra terminate in the caudate nucleus or the putamen. The subthalamic nuclei connect with the globus pallidus. For conductivity in basal ganglia of the rat see Oorschot (1996) J. Comp. Neurol. 366:580-599.

In a preferred embodiment, the administration site is the striatum of the brain, in particular the caudate putamen. Injection into the putamen can label target sites located in various distant regions of the brain, for example, the globus pallidus, amygdala, subthalamic nucleus or the substantia nigra. Transduction of cells in the pallidus commonly causes retrograde labeling of cells in the thalamus. In a preferred embodiment the (or one of the) target site(s) is the substantia nigra.

In a preferred embodiment, the vector is pseudotyped. In the design of retroviral vector systems it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus. The term pseudotyping means incorporating in at least a part of, or substituting a part of, or replacing all of, an env gene of a viral genome with a heterologous env gene, for example an env gene from another virus. In a preferred embodiment of the present invention the vector system is pseudotyped with a gene encoding at least part of the rabies G protein. In a further preferred embodiment of the present invention the vector system is pseudotyped with a gene encoding at least part of the VSV-G protein.

Methods of Administration

According to the invention, the cells are administered to the patient's brain. The cells may be implanted within the parenchyma of the brain, in the space containing cerebrospinal fluids, such as the sub-arachnoid space or ventricles, or extaneurally. As used herein, the term "extaneurally" is intended to indicate regions of the patient which are not within the central nervous system or peripheral nervous system, such as the celiac ganglion or sciatic nerve. "Central nervous system" is meant to include all structures within the dura mater.

Typically, the cells are administered by injection into the brain of the patient. Injections can generally be made with a sterilized syringe having an 18-21 gauge needle. Although the exact size needle will depend on the species being treated, the needle should not be bigger than 1 mm diameter in any species. Those of skill in the art are familiar with techniques for administering cells to the brain of a patient.

Differentiated neuronal and glia cells can be detected using immunocytochemical techniques know in the art. Immunocytochemistry (e.g. dual-label immunofluorescence and immunoperoxidase methods) uses antibodies that detect cell proteins to distinguish the cellular characteristics or phenotypic properties of neurons from glia. Cellular markers for neurons include NSE, NF, (3-tubulin, MAP-2 and NeuN. Cellular markers for glia include GFAP (an identifier of astrocytes), RC-2 (an identifier of radial glia) and M2.

Immunocytochemistry can also be used to identify neurons, by detecting the expression of neurotransmitters or the expression of enzymes responsible for neurotransmitter synthesis. For the identification of neurons, antibodies can be used that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or antidiuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins and enkephalins, prostaglandins, amino acids such as GABA, glycine, glutamate, cysteine, taurine and aspartate, and dipeptides such as carnosine. Antibodies to neurotransmitter-synthesizing enzymes can also be used such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the ACHE nicotinic and muscarinic receptors, adrenergic receptors, the dopamine receptor, and the like. Cells that contain a high level of melanin, such as those found in the substantia nigra, could be identified using an antibody to melanin.

In situ hybridization histochemistry can also be performed, using cDNA or RNA probes specific for the peptide neurotransmitter or the neurotransmitter synthesizing enzyme mRNAs. These techniques can be combined with immunocytochemical methods to enhance the identification of specific phenotypes. If necessary, the antibodies and molecular probes can be applied to Western and Northern blot procedures respectively to aid in cell identification.

Transplantation of Cells. Transplantation of new cells into the damaged CNS has the potential to repair damaged neural pathways and provide neurotransmitters, thereby restoring neurological function. However, the absence of suitable cells for transplantation purposes has prevented the full potential of this procedure from being met. "Suitable" cells are cells that meet the following criteria: (1) can be obtained in large numbers; (2) can be proliferated in vitro to allow insertion of genetic material, if necessary; (3) capable of surviving indefinitely but stop growing after transplantation to the brain; (4) are non-immunogenic, preferably obtained from a patient's own tissue or from a compatible donor; (5) are able to form normal neural connections and respond to neural physiological signals (Bjorklund, 14(8) *Trends Neurosci.* 319-322 (1991). The desired cells are obtainable from embryonic or adult CNS tissue, and which are able to divide over extended times when maintained in vitro using the culture conditions described herein, meet all of the desirable requirements of cells suitable for neural transplantation purposes and are a particularly suitable cell line as the cells have not been immortalized and are not of tumorigenic origin. The use of the cells in the treatment of neurological disorders and CNS damage can be demonstrated by the use of animal models. (See, the Examples which follow).

The cells can be administered to any animal with abnormal neurological or neurodegenerative symptoms obtained in any manner, including those obtained as a result of mechanical, chemical, or electrolytic lesions, as a result of aspiration of neural areas, or as a result of aging processes. Lesions in non-human animal models can be obtained with 6-hydroxydopamine (6-OHDA), 1-methyl-4-phenyl-1,2,3,6 tetrahydropyridine (MPTP), ibotenic acid, and the like.

The isolated cells can be prepared from donor tissue that is xenogeneic to the host. For xenografts to be successful, some method of reducing or eliminating the immune response to the implanted tissue is usually employed. Thus cell recipients can be immunosuppressed, either through the use of immunosuppressive drugs such as cyclosporin, or through local immunosuppression strategies employing locally applied immunosuppressants. Local immunosuppression is disclosed by Gruber, 54 *Transplantation* 1-11 (1992). U.S. Pat. No. 5,026,365 discloses encapsulation methods suitable for local immunosuppression.

As an alternative to employing immunosuppression techniques, methods of gene replacement or knockout using homologous recombination in embryonic stem cells, taught by Smithies et al., 317 *Nature* 230-234 (1985), and extended to gene replacement or knockout in cell lines (Zheng et al., 88 *Proc. Natl. Acad. Sci.* 8067-8071 (1991)), can be applied to the isolated cells for the ablation of major histocompatibility complex (MHC) genes. Cells lacking MHC expression allows for the grafting of enriched neural cell populations across allogeneic, and perhaps even xenogeneic, histocompatibility barriers without the need to immunosuppress the recipient. General reviews and citations for the use of recombinant methods to reduce antigenicity of donor cells are also disclosed by Gruber, 54 *Transplantation* 1-11 (1992). Exemplary approaches to the reduction of immunogenicity of transplants by surface modification are disclosed by PCT International patent application WO 92/04033 and PCT/US99/24630. Alternatively the immunogenicity of the graft may be reduced by preparing NS4 cells from a transgenic animal that has altered or deleted MHC antigens.

The isolated cells can be encapsulated and used to deliver factors to the host, according to known encapsulation technologies, including microencapsulation (see, e.g., U.S. Pat. Nos. 4,352,883; 4,353,888; and 5,084,350, herein incorporated by reference) and macroencapsulation (see, e.g., U.S. Pat. Nos. 5,284,761, 5,158,881, 4,976,859 and 4,968,733 and PCT International patent applications WO 92/19195 and WO 95/05452, each incorporated herein by reference). If the cells are encapsulated, macroencapsulation is preferred, as described in U.S. Pat. Nos. 5,284,761; 5,158,881; 4,976,859; 4,968,733; 5,800,828 and PCT International patent application WO 95/05452, each incorporated herein by reference. Cell number in the devices can be varied; preferably each device contains between $10^3$-$10^9$ cells (for example, $10^5$ to $10^7$ cells). Many macroencapsulation devices can be implanted in the host; preferably between one to 10 devices.

The cells prepared from tissue that is allogeneic to that of the recipient can be tested for use by the well-known methods of tissue typing, to closely match the histocompatibility type of the recipient.

In preferred embodiments, the cells are autologous cells, isolated from patient tissues. For example, cells can sometimes be prepared from the recipient's own nervous system (e.g., in the case of tumor removal biopsies). In such instances the cells can be generated from dissociated tissue and proliferated in vitro using the methods described in the Examples which follow. Upon suitable expansion of cell numbers, the cells may be harvested, genetically modified if necessary, and readied for direct injection into the recipient's CNS.

Transplantation can be done bilaterally, or, in the case of a patient suffering from Parkinson's Disease, contralateral to the most affected side. Surgery is performed in a manner in which particular brain regions may be located, such as in relation to skull sutures, particularly with a stereotaxic guide. The cells are delivered throughout any affected neural area, in particular to the basal ganglia, the caudate, the putamen, the nucleus basalis or the substantia nigra. Cells are administered to the particular region using any method which maintains the integrity of surrounding areas of the brain, such as by injection cannula. Injection methods are exemplified by those used by Duncan et al., 17 *J. Neurocytology* 351-361 (1988), and scaled up and modified for use in humans. Methods taught by Gage et al., supra, for the injection of cell suspensions such as fibroblasts into the CNS can also be used for injection of the cells. Additional approaches and methods may be found in Neural Grafting in the Mammalian CNS, Bjorklund & Stenevi, eds. (1985).

Cells administered to the particular neural region can form a neural graft, so that the cells form normal connections with neighboring neurons, maintaining contact with transplanted or existing glial cells, and providing a trophic influence for the neurons. Thus the transplanted cells re-establish the neuronal networks which have been damaged due to disease and aging.

It is a benefit of the cell(s) that they can be implanted into, and/or grafted to, a patient in need for use in cell therapy or gene therapy approaches to neurological injury or disease. Advantageously, the cell(s) can be used directly without requiring a step for cell expansion.

The present invention also relates to a cell culture derived from the cell(s) originated from epidermal basal cells. The cell culture contains a plurality of cells that have a morphological, physiological and/or immunological feature of a neural progenitor, neuronal, or glial cell, for example, expression of one or more specific marker(s). The cell culture is maintained under culture conditions that favor the in vitro propagation of neural progenitors, neuronal, or glial cells, for example, suitable temperature, pH, nutrients, and growth factors, as known in the art.

In one embodiment, the neural progenitor cells are cultured as described in the examples which follow, and these cells can be cultured in the presence of a differentiating factor to differentiate or transdifferentiate the cells into a desired phenotype, e.g. astrocytes, glial cells etc., and then transplanted into a patient. Thus, the desired cell type can be tailored to differentiate into a cell type that can replaced non-functional or abnormal cells to treat any disease. The cell culture can be manipulated to express additional or different neural-specific or glial specific-markers in the presence of specific exogenously supplied signal molecules.

The further course of development of the cells depends on the in situ environmental cues to which they are exposed, whether in vitro, or implanted in vivo. Optionally, the cell(s) are grown in a medium including a retinoid compound, such as retinoic acid or Vitamin A, a nerve growth factor or neurotrophin, such as brain-derived neurotrophic factor (BDNF), ciliary neurotrophic factor (CNTF), platelet-derived growth factor (PDGF), nerve growth factor (NGF), neurotrophin (NT)-3, neurotrophin (NT)-4, or sonic hedgehog (Shh),cyclic AMP, cAMP analogs, IBMX and/or functional fragments of any of these.

Compounds which may inhibit cAMP phosphodiesterase (s), and thereby increase the half-life of cAMP, are also useful in the subject method. Such compounds include aminone, milrinone, xanthine, methylxanthine, anagrelide, cilostamide, medorinone, indolidan, rolipram, 3-isobutyl-1-methylxanthine (IBMX), chelerythrine, cilostazol, glucocorticoids, griseolic acid, etazolate, caffeine, indomethacin, theophylline, papverine, methyl isobutylxanthine (MIX), and fenoxamine.

Certain analogs of cAMP, e.g., which are agonists of cAMP, can also be used. Exemplary cAMP analogs which may be useful in the present method include dibutyryl-cAMP (db-cAMP), (8-(4)-chlorophenylthio)-cAMP (cpt-cAMP), 8-[(4-bromo-2,3-dioxobutyl)thio]-cAMP, 2-[(4-bromo-2,3-dioxobutyl)thio]-cAMP, 8-bromo-cAMP, dioctanoyl-cAMP, Sp-adenosine 3':5'-cyclic phosphorothioate, 8-piperidino-cAMP, $N^6$-phenyl-cAMP, 8-methylamino-cAMP, 8-(6-aminohexyl)amino-cAMP, 2'-deoxy-cAMP, $N^6$,2'-O-dibutryl-cAMP, $N^6$,2'-O-disuccinyl-cAMP, $N^6$-monobutyryl-cAMP, 2'-O-monobutyryl-cAMP, 2'-O-monobutryl-8-bromo-cAMP, $N^6$-monobutryl-2'-deoxy-cAMP, and 2'-O-monosuccinyl-cAMP.

For example, treating newly formed neuronal cells with all-trans retinoic acid and BDNF results in development of GABAergic neurons or neuron-like cells (that express Neurofilament M), whereas treatment with glial-conditioned media and sonic hedgehog aminoterminal peptide (Shh-N) results in development of mostly dopaminergic neuronal cells. Treatment with Shh-N promotes the differentiation of neuronal and oligodendroglial species from nestin-immunoreactive cells (uncommitted neural progenitor cells) and inhibits the antiproliferative, astroglial-inductive, oligodendroglial-suppressive effects of BMP2. (E.g., G. Zhu et al., *Sonic hedgehog and BMP2 exert opposing actions on proliferation and differentiation of embryonic neural progenitor cells, Dev. Biol.* 21591):118-29 [1999]). This plasticity in response to the environmental cues allows the cells to maintain neuronal differentiation in vitro or in situ, when implanted into the mammalian subject.

In accordance with the method, expression of any neural progenitor-specific, neural-specific, and/or glial specific marker is detected by conventional biochemical or immunochemical means. Preferably, immunochemical means are employed, such as, but not limited to, enzyme-linked immunosorbent assay ELISA), immunofluorescent assay (WA), immunoelectrophoresis, immunochromatographic assay or immunohistochemical staining. These methods employ marker-specific polyclonal or monoclonal antibodies or antibody fragments, for example Fab, Fab', F(ab')$_2$, or F(v) fragments, that selectively bind any of various neural progenitor, neuronal or glial cell antigens. Antibodies targeting individual specific markers are commercially available and are conveniently used as recommended by the antibody manufacturers. Markers specific to neural progenitor, neuronal, or glial cells include antigenic molecules that indicate expression of, for example, nestin, neural RNA-binding protein Musashi, neurofilament M (NF-M; Sigma, Inc.), neural-specific tubulin (Sigma, Inc.), neural-specific enolase (Incstar, Inc.), microtubule associated protein 2 (MAP2, Boehringer Mannheim), glial fibrillary acidic protein, O4, or any other detectable marker specific to a neural progenitor, neuronal or glial cell.

Alternatively, expression of neural progenitor-specific, neural-specific or glial-specific markers is detected by conventional molecular biological techniques for amplifying and analyzing mRNA transcripts encoding any of the markers, such as but not limited to reverse transcriptase-mediated polymerase chain reaction (RT-PCR), transcription-mediated amplification (TMA), reverse transcriptase-mediated ligase chain reaction (RT-LCR), or hybridization analysis. Nucleic acid sequences encoding markers (e.g., nestin, neural RNA-binding protein Musashi, neurofilament M, neural-specific tubulin, neural-specific enolase, microtubule associated protein 2, glial fibrillary acidic protein, O4) specific to neural progenitor, neuronal or glial cells are known and available in databases such as GenBank. The skilled artisan can readily determine other useful marker-specific sequences for use as primers or probes by conducting a sequence similarity search of a genomics data base, such as the GenBank database of the National Center for Biotechnology Information (NCBI), using a computerized algorithm, such as PowerBLAST, QBLAST, PSI-BLAST, PHI-BLAST, gapped or ungapped BLAST, or the "Align" program through the Baylor College of Medicine server. (E.g., Aitchul, S. F., et al., *Gapped BLAST and PSI-BLAST: a new generation of protein database search programs*, Nucleic Acids Res. 25(17):3389-402 [1997]; Zhang, J., & Madden, T. L., *PowerBLAST: a new network BLAST application for interactive or automated sequence analysis and annotation*, Genome Res. 7(6):649-56 [1997]); Madden, T. L., et al., *Applications of network BLAST server*, Methods Enzymol. 266:131-41 [1996]; Altschul, S. F., et al., *Basic local alignment search tool*, J. Mol. Biol. 215(3):403-10 [1990]).

Optionally, morphological criteria are additionally used to detect transdifferentiation of epidermal basal cells into neurons or neuron-like cells. For example, neurons or neuron-like cells may express neurites, or neurite-like processes, longer than three cell diameters (about 50 microns or longer).

The presence of neural progenitors can be detected by functional testing under suitable physiological conditions to determine the course of development and differentiation into neuronal or glial cells. Preferably, neural progenitor cells are identified by detecting the expression of any of several well-defined specific markers, such as the cytoskeletal protein nestin and/or neural RNA-binding protein Musashi (MSI). (E.g., T. Nagata et al., *Structure, backbone dynamics and interactions with RNA of the C-terminal RNA-binding domain of a mouse neural RNA-binding protein, Musashi1*, J. Mol. Biol. 287(2):315-30 [1999]; P. Good et al., *The human Musashi homolog 1 (MSI1) gene encoding the homologue of Musashi/Nrp-1, a neural RNA-binding protein putatively expressed in CNS stem cells and neural progenitor cells*, Genomics 52(3):382-84 [1998]; S. Sakakibara et al., *Mouse-Musashi-1, a neural RNA-binding protein highly enriched in the mammalian CNS stem cell*, Dev. Biol. 176(2):230-42 [1996]).

The features and properties of the transdifferentiated cells and cell cultures of the present invention make them viable as a fundamental biotechnology tool directed to the human nervous system. Moreover, the transdifferentiated cells and cell cultures of the invention meet the technical criteria for use in cell and gene therapies directed to nervous system disease and disorders. First, the inventive transdifferentiated cells and cell cultures can display morphological and functional features of neurons: they can develop long neurites with a growth cones at the end, they express a number of neural specific genes; and they do not continue to proliferate in conditions which induce differentiation. Therefore, for use in gene therapy and cell therapy, the transdifferentiated cells can not only deliver a single potential gene or factor, but additionally are capable of furnishing the whole infrastructure for nerve regeneration.

Second, the cultured transdifferentiated cells can be propagated as multipotential nervous system progenitor cells in conditions that favor proliferation and do not induce differentiation. Hence, these progenitor cells retain the capacity to become many different types of neurons or neuron-like cells depending upon the environmental cues to which they are exposed, for example GABAergic or dopaminergic cells. This broad plasticity suggests that, once implanted, the cells of the present invention will retain the capacity to conform to many different host brain regions and to differentiate into neurons specific for that particular host region. (See, the Examples which follow). These intrinsic properties of the transdifferentiated neurons are different from the existing tumorigenic cell lines, where some neuronal differentiation can be induced under artificial conditions.

Third, another advantage of the inventive transdifferentiated cells and cell cultures is that there is no need for cell expansion, as is required with stem cell technology used to generate neurons for cell and gene therapies. Thus, the transdifferentiated cells of the present invention are sufficient in number (several millions of cells) for direct implantation. In summary, the unique characteristics and properties of these transdifferentiated cells and cell cultures yield an invention of significant scientific and commercial potential.

Consequently, the present invention also relates to a method of delivering locally secretable regulatory factors in vivo within the nervous system of a mammalian subject, including a human. The method involves transdifferentiating a population of epidermal basal cells from the subject, in accordance with the inventive method described above, into cells having a morphological, physiological and/or immunological feature of a neuronal cell. Before or after the transdifferentiation step, the cells can be genetically modified, in vitro, with an expression vector comprising a DNA encoding a predetermined secretable regulatory factor, a biochemical precursor thereof or an enzyme that catalyzes the biosynthesis of either the factor or a precursor, and the genetically modified cells are selected, cultured, and implanted into the subject. Enhanced secretion of the regulatory factor by the genetically modified cells results. This does not depend on the formation of functional interneuronal connections such as those that transmit electrochemical sensory, motor, or cognitive signals.

Examples of secretable regulatory factors include dopamine and neurotrophic factors, such as nerve growth factor (NGF), brain-derived growth factor (BDGF), neurotrophin-3, neurotrophin-4, insulin-like growth factor, ciliary neurotrophic factor (CNTF), or glia-derived neurotrophic factor. Nervous system disorders that can be treated using the method include Alzheimer's disease, diabetic neuropathy, taxol neuropathy, compressive neuropathy, AIDS related neuropathy, amyotrophic lateral sclerosis, large fiber neuropathy, vincristine neuropathy, and Parkinson's disease.

Survival of the cell graft in the living host can be examined using various non-invasive scans such as computerized axial tomography (CAT scan or CT scan), nuclear magnetic resonance or magnetic resonance imaging (NMR or MRI), or positron emission tomography (PET) scans. Post-mortem examination of graft survival can be done by removing the neural tissue, and examining the affected region macroscopically and microscopically. Cells can be stained with any stains visible under light or electron microscopic conditions, more particularly with stains that are specific for neurons and glia. Particularly useful are monoclonal antibodies that identify neuronal cell surface markers such as the M6 antibody that identifies mouse neurons. Also useful are antibodies that identify neurotransmitters (such as GABA, TH, ChAT, and substance P) and to enzymes involved in the synthesis of neurotransmitters (such as GAD). Transplanted cells can also be identified by prior incorporation of tracer dyes such as rhodamine-labeled or fluorescein-labeled microspheres, fast blue, bisbenzamide, or retrovirally introduced histochemical markers such as the lacZ gene, which produces, .alpha.-galactosidase.

Functional integration of the graft into the host's neural tissue can be assessed by examining the effectiveness of grafts on restoring various functions, including but not limited to tests for endocrine, motor, cognitive and sensory functions. Motor tests that can be used include those that measure rotational movement away from the degenerated side of the brain, and those that measure slowness of movement, balance, coordination, akinesia or lack of movement, rigidity and tremors. Cognitive tests include various tests of ability to perform everyday tasks, as well as various memory tests, including maze performance.

The ability to expand cells in vitro using the methods described herein, for use in transplantation is also useful for ex vivo gene therapy. For instance, rat primary astroglial cells or a human astroglial cell line (Tornatore et al., 5 *Cell Transplant* 145-63 (1996)) have been transduced with the tyrosine hydroxylase gene and implanted in models of Parkinson's disease. More recently, astroglial cells for ex vivo gene therapy have also been derived from adult human cortex (Ridet et al., 10 *Hum. Gene Ther.* 27 1-80 (1999)). Thus, the isolated cells provide an additional way to retrieve and expand astroglial cells for use as vehicles in ex vivo gene therapy trials.

Differentiation of Neural Progenitor/Stem Cells

Differentiation of the cells can be induced by any method known in the art which activates the cascade if biological events which lead to growth, which include the liberation of inositol triphosphate and intracellular $Ca^{2+}$, liberation of diacyl glycerol and the activation of protein kinase C and other cellular kinases, and the like. Treatment with phorbol esters, differentiation-inducing growth factors and other chemical signals can induce differentiation. Differentiation can also be induced by plating the cells on a fixed substrate such as flasks, plates, or coverslips coated with an ionically charged surface such as poly-L-Lysine and poly-L-ornithine and the like.

Other substrates may be used to induce differentiation such as collagen, fibronectin, laminin, MATRIGEL™ (Collaborative Research), and the like. Differentiation can also be induced by leaving the cells in suspension in the presence of a proliferation-inducing growth factor, without reinitiation of proliferation (i.e. without dissociating the neurospheres).

A preferred method for inducing differentiation of the neural progenitors is described in detail in the examples which follow. Other methods that can be used comprise culturing the cells on a fixed substrate in a culture medium that is free of the proliferation-inducing growth factor. After removal of the proliferation-inducing growth factor, the cells adhere to the substrate (e.g. poly-ornithine-treated plastic or glass), flatten, and begin to differentiate into neurons and glial cells. At this stage the culture medium may contain serum such as 0.5-1.0% fetal bovine serum (FBS). However, for certain uses, if defined conditions are required, serum would not be used. Within 2-3 days, most or all of the neural cell progeny begin to lose immunoreactivity for nestin and begin to express antigens specific for neurons, astrocytes or oligodendrocytes as determined by immunocytochemistry techniques well known in the art.

Immunocytochemistry (e.g. dual-label immunofluorescence and immunoperoxidase methods) utilizes antibodies that detect cell proteins to distinguish the cellular characteristics or phenotypic properties of neurons from astrocytes and oligodendrocytes. In particular, cellular markers for neurons include NSE, NF, β-tubulin, MAP-2; and for glia, GFAP (an identifier of astrocytes), galactocerebroside (GalC) (a myelin glycolipid identifier of oligodendrocytes), and the like.

Immunocytochemistry can also be used to detect the expression of neurotransmitters, or in some cases the expression of enzymes responsible for neurotransmitter synthesis. For the identification of neurons, antibodies can be used that detect the presence of acetylcholine (ACh), dopamine, epinephrine, norepinephrine, histamine, serotonin or 5-hydroxytryptamine (5-HT), neuropeptides such as substance P, adrenocorticotrophic hormone, vasopressin or anti-diuretic hormone, oxytocin, somatostatin, angiotensin II, neurotensin, and bombesin, hypothalamic releasing hormones such as TRH and luteinizing releasing hormone, gastrointestinal peptides such as vasoactive intestinal peptide (VIP) and cholecystokinin (CCK) and CCK-like peptide, opioid peptides such as endorphins like β-endorphin and enkephalins such as met- and leu-enkephalin, prostaglandins, amino acids such as γ-amino butyric acid (GABA), glycine, glutamate, cysteine, taurine and aspartate and dipeptides such as carnosine. Antibodies to neurotransmitter-synthesizing enzymes can also be used such as glutamic acid decarboxylase (GAD) which is involved in the synthesis of GABA, choline acetyltransferase (ChAT) for ACh synthesis, dopa decarboxylase (DDC) for dopamine, dopamine-β-hydroxylase (DBH) for norepinephrine, and amino acid decarboxylase for 5-HT. Antibodies to enzymes that are involved in the deactivation of neurotransmitters may also be useful such as acetyl cholinesterase (AChE) which deactivates ACh. Antibodies to enzymes involved in the reuptake of neurotransmitters into neuronal terminals such as monoamine oxidase and catechol-o-methyl transferase for dopamine, for 5-HT, and GABA transferase for GABA may also identify neurons. Other markers for neurons include antibodies to neurotransmitter receptors such as the AChE nicotinic and muscarinic receptors, adrenergic receptors $alpha_1$, $alpha_2$, $beta_1$ and $alpha_2$, the dopamine receptor and the like. Cells that contain a high level of melanin, such as those found in the substantia nigra, could be identified using an antibody to melanin.

In situ hybridization histochemistry can also be performed, using cDNA or RNA probes specific for the peptide neurotransmitter or the neurotransmitter synthesizing enzyme mRNAs. These techniques can be combined with immunocytochemical methods to enhance the identification of specific phenotypes. If necessary, the antibodies and molecular probes discussed above can be applied to Western and Northern blot procedures respectively to aid in cell identification.

A preferred method for the identification of neurons uses immunocytochemistry to detect immunoreactivity for NSE, NF, NeuN; and the neuron specific protein, tau-1. Because these markers are highly reliable, they will continue to be useful for the primary identification of neurons, however neurons can also be identified based on their specific neurotransmitter phenotype as previously described.

Type I astrocytes, which are differentiated glial cells that have a flat, protoplasmic/fibroblast-like morphology, are preferably identified by their immunoreactivity for GFAP but not A2B5. Type II astrocytes, which are differentiated glial cells that display a stellate process-bearing morphology, are preferably identified using immunocytochemistry by their phenotype GFAP(+), A2B5(+) phenotype.

Cells that do not express intermediate filaments specific for neurons or for astrocytes, begin to express markers specific for oligodendrocytes in a correct temporal fashion. That is, the cells first become immunoreactive for O4, galactocerebroside (GalC, a myelin glycolipid) and finally, MBP. These cells also possess a characteristic oligodendrocyte morphology.

The biological effects of growth and trophic factors are generally mediated through binding to cell surface receptors. The receptors for a number of these factors have been identified and antibodies and molecular probes for specific receptors are available. Neural progenitor cells can be analyzed for the presence of growth factor receptors at all stages of differentiation. In many cases, the identification of a particular receptor will define the strategy to use in further differentiating the cells along specific developmental pathways with the addition of exogenous growth or trophic factors.

Exogenous growth factors can be added alone or in various combinations. They can also be added in a temporal sequence (i.e. exposure to a first growth factor influences the expression of a second growth factor receptor, Neuron 4:189-201 (1990). Among the growth factors and other molecules that can be used to influence the differentiation of precursor cells in vitro are FGF-1, FGF-2, ciliary neurotrophic factor (CNTF), NGF, brain-derived neurotrophic factor (BDNF), neurotrophin 3, neurotrophin 4, interleukins, leukemia inhibitory factor (LIF), cyclic adenosine monophosphate, forskolin, tetanus toxin, high levels of potassium, amphiregulin, TGF-$\alpha$, TGF$\beta$ insulin-like growth factors, dexamethasone (glucocorticoid hormone), isobutyl 3-methylxanthine, somatostatin, growth hormone, retinoic acid, and PDGF. These and other growth factors and molecules will find use in the present invention.

Diseases

Parkinson's disease: Parkinson's disease (PD) is characterized by the progressive loss in function of dopaminergic neurons. The progressive loss of dopaminergic function interferes with the normal working of the neuronal circuitry necessary for motor control so that patients with PD show characteristic motor disturbances such as akinesia, rigidity and rest tremor. Other symptoms include pain, impaired olfaction, alterations of personality and depression. Quinn et al., (1997) Baillieres Clin. Neurol. 6:1-13.

According to the invention, dopaminergic neuronal cells are generated using the cell culturing method described herein and described in detail in the Examples which follow. The dopaminergic cells are then administered to the brain of the patient in need thereof to produce dopamine and restore behavioral deficits in the patient. Preferably, the cells are administered to the basal ganglia of the patient.

Alzheimer's disease: Alzheimer's disease involves a deficit in cholinergic cells in the nucleus basalis. Thus, a subject having Alzheimer's disease may be treated by administering cells cultured according to the method of the invention that are capable of producing acetylcholine.

Huntington's disease: Huntington's disease involves a gross wasting of the head of the caudate nucleus and putamen, usually accompanied by moderate disease of the gyrus. A subject suffering from Huntington's disease can be treated by implanting cells cultured according to the method of the invention that are capable of producing the neurotransmitters gamma amino butyric acid (GABA), acetylcholine, or a mixture thereof.

Gene Therapy: In an additional embodiment of the invention, the cultured cells may be transfected with a nucleic acid which encodes a neurologically relevant polypeptide. The term "neurologically relevant peptide" generally refers to a peptide or protein which catalyzes a reaction within the tissues of the central nervous system. Such peptides may be naturally occurring neural peptides, proteins or enzymes, or may be peptide or protein fragments which have therapeutic activity within the central nervous system.

According to this aspect of the invention, cells are cultured in vitro as described herein and an exogenous gene encoding a desired gene product is introduced into the cells, for example, by transfection. The transfected cultured cells can then be administered to a patient with a neurological disorder.

Genes of Interest

Examples of neurologically relevant peptides include neural growth factors and enzymes used to catalyze the production of important neurochemicals or their intermediates. The peptide encoded by the nucleic acid may be exogenous to the host or endogenous. For example, an endogenous gene that supplements or replaces deficient production of a peptide by the tissue of the host wherein such deficiency is a cause of the symptoms of a particular disorder. In this case, the cell lines act as an artificial source of the peptide. Alternatively, the peptide may be an enzyme which catalyzes the production of a therapeutic or neurologically relevant compound. Again, such compounds may be exogenous to the patient's system or may be an endogenous compound whose synthetic pathway is otherwise impaired. Examples of neurologically relevant compounds include tyrosine hydroxylase, nerve growth factor (NGF), brain derived neurotrophic factor (BDGF), basic fibroblast growth factor (bFGF) and glial cell line derived growth factor (GDGF).

Drug Screening

Neural precursor cells of this invention can be used to screen for factors (such as solvents, small molecule drugs, peptides, polynucleotides) or environmental conditions (such as culture conditions or manipulation) that affect the characteristics of neural precursor cells and their various progeny.

In some applications, the expanded cells (undifferentiated or differentiated) are used to screen factors that promote maturation into neural cells, or promote proliferation and maintenance of such cells in long-term culture. For example, candidate maturation factors or growth factors are tested by adding them to cells in different wells, and then determining any phenotypic change that results, according to desirable criteria for further culture and use of the cells.

In a preferred embodiment, the cells are expanded (cell proliferation) as described in detail in the Examples which follow.

Other screening applications of this invention relate to the testing of pharmaceutical compounds for their effect on neural tissue or nerve transmission. Screening may be done either because the compound is designed to have a pharmacological effect on neural cells, or because a compound designed to have effects elsewhere may have unintended side effects on the nervous system. The screening can be conducted using any of the neural precursor cells or terminally differentiated cells of the invention, such as dopaminergic, serotonergic, cholinergic, sensory, and motor neurons, oligodendrocytes, and astrocytes.

The reader is referred generally to the standard textbook "In vitro Methods in Pharmaceutical Research", Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in "In vitro Methods in Pharmaceutical Research," Academic Press, 1997) for further elaboration.

Effect of cell function can be assessed using any standard assay to observe phenotype or activity of neural cells, such as receptor binding, neurotransmitter synthesis, release or uptake, electrophysiology, and the growing of neuronal processes or myelin sheaths—either in cell culture or in an appropriate model.

Administration of Compositions to Animals

Candidate agents identified by the compositions and methods described herein, may be administered to animals including human beings in any suitable formulation. For example, compositions for targeting a tumor cell may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

Therapeutic Use: This invention also provides for the use of neural precursor cells to restore a degree of central nervous system (CNS) function to a subject needing such therapy, perhaps due to an inborn error in function, the effect of a disease condition, or the result of an injury.

To determine the suitability of neural precursor cells for therapeutic administration, the cells can first be tested in a suitable animal model. Details regarding transplantation of the cells are described in the examples which follow.

At one level, cells are assessed for their ability to survive and maintain their phenotype in vivo. Neural precursor cells are administered to immunodeficient animals (such as nude mice, or animals rendered immunodeficient chemically or by irradiation) at an observable site, such as in the cerebral cavity or in the spinal chord. Tissues are harvested after a period of a few days to several weeks or more, and assessed as to whether transplanted cells are still present.

This can be performed as described in the examples which follow, or by administering cells that express a detectable label (such as green fluorescent protein, or β-galactosidase); that have been prelabeled (for example, with BrdU or [$^3$H] thymidine), or by subsequent detection of a constitutive cell marker (for example, using human-specific antibody). Where neural precursor cells are being tested in a rodent model, the presence and phenotype of the administered cells can be assessed by immunohistochemistry or ELISA using human-specific antibody, or by RT-PCR analysis using primers and hybridization conditions that cause amplification to be specific for human polynucleotide sequences. Suitable markers for assessing gene expression at the mRNA or protein level are provided elsewhere in this disclosure.

Various animal models for testing restoration of nervous system function are described in "CNS Regeneration: Basic Science and Clinical Advances", M. H. Tuszynski & J. H. Kordower, eds., Academic Press, 1999.

Differentiated cells of this invention can also be used for tissue reconstitution or regeneration in a human patient in need thereof. The cells are administered in a manner that permits them to graft or migrate to the intended tissue site and reconstitute or regenerate the functionally deficient area.

Certain neural progenitor cells embodied in this invention are designed for treatment of acute or chronic damage to the nervous system. For example, excitotoxicity has been implicated in a variety of conditions including epilepsy, stroke, ischemia, Huntington's disease, Parkinson's disease and Alzheimer's disease. Certain differentiated cells of this invention may also be appropriate for treating dysmyelinating disorders, such as Pelizaeus-Merzbacher disease, multiple sclerosis, leukodystrophies, neuritis and neuropathies. Appropriate for these purposes are cell cultures enriched in oligodendrocytes or oligodendrocyte precursors to promote remyelination.

By way of illustration, neural stem cells are transplanted directly into parenchymal or intrathecal sites of the central nervous system, according to the disease being treated. Grafts can be done using single cell suspension or small aggregates at a density of 25,000-500,000 cells per μL (U.S. Pat. No. 5,968,829). The efficacy of transplants of motor neurons or their precursors can be assessed in a rat model for acutely injured spinal cord as described by in the examples which follow or McDonald et al. (*Nat. Med.* 5:1410, 1999). A successful transplant will show transplant-derived cells present in the lesion 2-5 weeks later, differentiated into astrocytes, oligodendrocytes, and/or neurons, and migrating along the cord from the lesioned end, and an improvement in gate, coordination, and weight-bearing.

The neural progenitor cells and terminally differentiated cells according to this invention can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. The composition may optionally be packaged in a suitable container with written instructions for a desired purpose, such as the reconstitution of CNS function to improve some neurological abnormality.

Formulations

While it is possible for an antibody or fragment thereof to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Assay

Another aspect of the invention provides an assay for evaluating the effect of substances on differentiated cells, preferably differentiated neuronal cells. The assay can be used to discover drugs capable of regulating the survival, proliferation or genesis of neuronal cells. According to this aspect of the invention, a population of neuronal cells is produced by the cell culturing method described above. The population of cells is contacted with a substance of interest and the effect on the cell population is monitored. The impact on the cell population can be monitored, for example, by determining whether the substance causes an increase or decrease in the expression of a reporter gene by examining the level of its protein, RNA, biological activity or other methods. For example, in one immunocytochemical method, the dopaminergic cells are monitored to determine the impact of a substance on the expression of tyrosine hydroxylase.

Substances of interest include extracts from tissues or cells, conditioned media from primary cells or cell lines, polypeptides whether naturally occurring or recombinant, nucleotides (DNA or RNA) and non-protein molecules whether naturally occurring or chemically synthesized.

Compounds

In a preferred embodiment, the methods and compositions of the invention are used to identify compounds that promote long term survival of non-immortalized cells. Compounds that are toxic, as measured by cell death or affects the cell divisions can be identified. Compounds which promote the division of the cells can be screened using the methods of the invention. The most preferred compounds identified using the present method will be non-toxic, showing no reduction in viability between treated and non-treated cultures. However, low toxicity levels may be tolerable for certain uses (e.g., in initial compound testing and design).

Methods for screening effects of drugs on isolated non-immortalized cells: The cell cultures can be used for the screening of potential neurologically therapeutic compositions. These test compositions can be applied to cells in culture at varying dosages, and the response of the cells monitored for various time periods. Physical characteristics of the cells can be analyzed by observing cell and neurite growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots can be used to examine the levels of mRNA coding for these molecules, or for enzymes which synthesize these molecules.

Alternatively, cells treated with these pharmaceutical compositions can be transplanted into an animal, and their survival, their ability to form neural connections, and their biochemical and immunological characteristics examined.

The isolated cells can be used in methods of determining the effect of a biological agents on neural cells. The term "biological agent" refers to any agent, such as a virus, protein, peptide, amino acid, lipid, carbohydrate, nucleic acid, nucleotide, drug, pro-drug or other substance that may have an effect on neural cells whether such effect is harmful, beneficial, or otherwise. Biological agents that are beneficial to neural cells are referred to herein as "neurological agents", a term which encompasses any biologically or pharmaceutically active substance that may prove potentially useful for the proliferation, differentiation or functioning of CNS cells or treatment of neurological disease or disorder. For example, the term may encompass certain neurotransmitters, neurotransmitter receptors, growth factors, growth factor receptors, and the like, as well as enzymes used in the synthesis of these agents.

The biological agent can be the biological agent is selected from the group consisting of basic fibroblast growth factor, acid fibroblast growth factor, epidermal growth factor, transforming growth factor .alpha., transforming growth factor .beta., nerve growth factor, insulin like growth factor, platelet derived growth factor, glia-derived neurotrophic factor, brain derived neurotrophic factor, ciliary neurotrophic factor, phorbol 12-myristate 13-acetate, tryophotin, activin, thyrotropin releasing hormone, interleukins, bone morphogenic protein, macrophage inflammatory proteins, heparan sulfate, amphiregulin, retinoic acid, tumor necrosis factor α, fibroblast growth factor receptor, epidermal growth factor receptor. Examples of biological agents include trophic factors such as glial-derived neurotrophic factor (GDNF); regulators of intracellular pathways associated with growth factor activity such as staurosporine, CGP-4 1251, and the like; hormones; various proteins and polypeptides such as interleukins and the Bcl-2 gene product; oligonucleotides such as antisense strands directed, for example, against transcripts for receptors; heparin-like molecules; and a variety of other molecules that have an effect on radial glial cells or CNS neural stem cell.

To determine the effect of a potential biological agent on neural cells from a particular host, a culture of isolated cells can be obtained from normal neural tissue or, alternatively, from a host afflicted with a CNS disease or disorder. The choice of culture conditions depends upon the particular agent being tested and the effects one wants to achieve. Once the cells are obtained from the desired donor tissue, they are proliferated in vitro in the presence of a proliferation-inducing growth factor.

The ability of various biological agents to increase, decrease or modify in some other way the number and nature of the cells can be screened on cells proliferated in the presence of EGF or other proliferation-inducing factor by the methods described in the Examples which follow.

It is possible to screen for biological agents that increase the proliferative ability of the isolated cells which would be useful for generating large numbers of cells for transplantation purposes. It is also possible to screen for biological agents that inhibit cell proliferation, e.g. treatment of cancer. The cells are plated in the presence of the biological factors of interest and assayed for the degree of proliferation that occurs. The effects of a biological agent or combination of biological agents on the differentiation and survival of cells and their progeny can be determined.

It is possible to screen cells which have already been induced to differentiate prior to the screening. It is also possible to determine the effects of the biological agents on the differentiation process by applying them to cells prior to differentiation. Generally, the biological agent can be solubilized and added to the culture medium at varying concentrations to determine the effect of the agent at each dose. The culture medium may be replenished with the biological agent every couple of days in amounts so as to keep the concentration of the agent somewhat constant.

Changes in proliferation are observed by an increase or decrease in the uptake of BrDU or telomerase expression (See, the Examples which follow). A "regulatory factor" is a biological factor that has a regulatory effect on the proliferation of cells. For example, a biological factor would be considered a "regulatory factor" if it increases or decreases the number of cells that proliferate in vitro in response to a proliferation-inducing growth factor (such as EGF). Alternatively, the number of cells that respond to proliferation-inducing factors may remain the same, but addition of the regulatory factor affects the rate at which the cells proliferate. A proliferation-inducing growth factor may act as a regulatory factor when used in combination with another proliferation-inducing growth factor.

Other regulatory factors include sulfate, TGF, activin, BMP-2, CNTF, retinoic acid, TNF, MIP-1, MIP-2, NGF, PDGF, interleukins, and the Bcl-2 gene product. Other factors having a regulatory effect on for example, a stem cell proliferation include those that interfere with the activation of the c-fos pathway (an intermediate early gene, known to be activated by EGF), including phorbol 12 myristate 13-acetate (PMA; Sigma), which up-regulates the c-fos pathway and staurosporine (Research Biochemical International) and CGP-41251 (Ciba-Geigy), which down regulate c-fos expression and factors, such as tyrphostin (Fallon et al., 11(5) *Mol. Cell. Biol.* 2697-2703 (1991)) and the like, which suppress tyrosine kinase activation induced by the binding of EGF to its receptor.

The regulatory factors are added to the culture medium at a concentration in the range of about 10 pg/ml to 500 ng/ml (preferably, for example, about 1 ng/ml to 100 ng/ml, or more preferably about 10 ng/ml). The regulatory factor retinoic acid is prepared from a 1 mM stock solution and used at a final concentration between about 0.01 μM and 100 μM (preferably, for example, between about 0.05 μM to 5 μM).

The glycosaminoglycan, heparan sulfate, is a ubiquitous component on the surface of mammalian cells known to affect a variety of cellular processes, and which binds to growth factor molecules such as FGF and amphiregulin, thereby promoting the binding of these molecules to their receptors on the surfaces of cells. Heparan sulfate can be added to the culture medium in combination with other biological factors, at a concentration of about 1 ng/ml to 1 mg/ml (preferably, for example, about 0.2 μg/ml to 20 μg/ml, or more preferably about 2 g/ml).

Using these screening methods, one of skill in the art can screen for potential drug side-effects on pre-natal and post-natal CNS cells by testing for the effects of the biological agents on neural cell proliferation and differentiation or the survival and function of differentiated CNS cells. The proliferated cells are typically plated at a density of about $5-10\times10^6$ cells/ml. If it is desired to test the effect of the biological agent on a particular differentiated cell type or a given make-up of cells, the ratio of neurons to glial cells obtained after differentiation can be manipulated by separating the different types of cells. Astrocytes can be panned out after a binding procedure using the RAN 2 antibody (available from ATCC). Tetanus toxin (available from Boerhinger Ingelheim) can be used to select out neurons. By varying the trophic factors added to the culture medium used during differentiation it is possible to intentionally alter the phenotype ratios. Such trophic factors include EGF, FGF, BDNF, CNTF, TGF, GDNF, and the like. For example, FGF increases the ratio of neurons, and CNTF increases the ratio of oligodendrocytes. Growing the cultures on beds of glial cells obtained from different CNS regions can also affect the course of differentiation.

The effects of the biological agents are identified based upon significant differences relative to control cultures with respect to criteria such as the ratios of expressed phenotypes (neurons, glial cells, or neurotransmitters or other markers), cell viability and alterations in gene expression. Physical characteristics of the cells can be analyzed by observing cell and neurite morphology and growth with microscopy. The induction of expression of new or increased levels of proteins such as enzymes, receptors and other cell surface molecules, or of neurotransmitters, amino acids, neuropeptides and biogenic amines can be analyzed with any technique known in the art which can identify the alteration of the level of such molecules. These techniques include immunohistochemistry using antibodies against such molecules, or biochemical analysis. Such biochemical analysis includes protein assays, enzymatic assays, receptor binding assays, enzyme-linked immunosorbant assays (ELISA), electrophoretic analysis, analysis with high performance liquid chromatography (HPLC), Western blots, and radioimmune assays (RIA). Nucleic acid analysis such as Northern blots and PCR can be used to examine the levels of mRNA coding for these molecules, or for enzymes which synthesize these molecules.

The factors involved in the proliferation of desired cell types and the proliferation, differentiation and survival of these cell progeny, and their responses to biological agents can be isolated by constructing cDNA libraries from a desired cell type cells or cell progeny at different stages of their development using techniques known in the art. The libraries from cells at one developmental stage are compared with those of cells at different stages of development to determine the sequence of gene expression during development and to reveal the effects of various biological agents or to reveal new biological agents that alter gene expression in CNS cells. When the libraries are prepared from dysfunctional tissue, genetic factors may be identified that play a role in the cause of dysfunction by comparing the libraries from the dysfunctional tissue with those from normal tissue. This information can be used in the design of therapies to treat the disorders. Additionally, probes can be identified for use in the diagnosis of various genetic disorders or for use in identifying neural cells at a particular stage in development.

Figure 3:
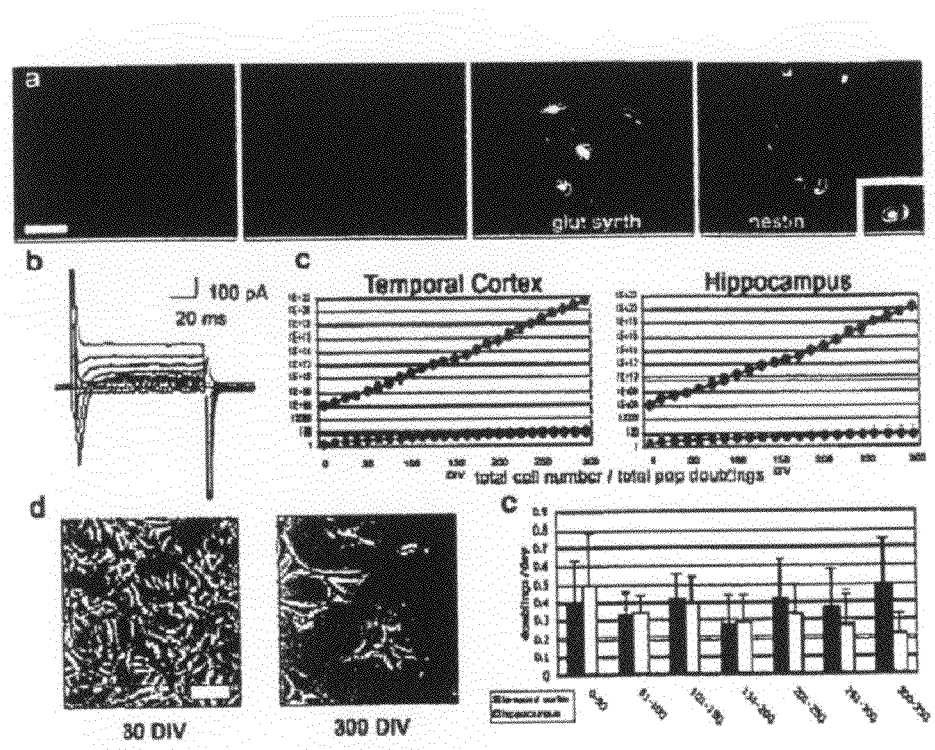
FIGS. 3A-3E show the expansion of primary neural cells as purified astroglial precursors.

Electrophysiological analysis can be used to determine the effects of biological agents on neuronal characteristics such as resting membrane potential, evoked potentials, direction and ionic nature of current flow and the dynamics of ion channels. These measurements can be made using any technique known in the art, including extracellular single unit voltage recording, intracellular voltage recording, voltage clamping and patch clamping. Voltage sensitive dyes and ion sensitive electrodes may also be used. For example, to identify cultured cell types, primary cells were examined for expression of phenotypic markers. Following dissociation, immunocytochemistry on primary cells 3 days in vitro (DIV) revealed a heterogeneous population containing predominantly astrotypic (GFAP+) cells, but included neuronal (NeuN+, PSA-NCAM+) and oligodendrocyte (CNPase+, O4+) phenotypes. Following their explantation into culture, only astrotypic cells appear to re-enter the cell cycle as shown by their uptake of thymidine analog 5-bromodeoxyuridine (BrDU) and were expandable as a purified population with specific mitogens. Presumptive neurons and oligodendrocytes were not appreciated in culture after 14 DIV. Microglia (CD11$^+$) were present initially and did not significantly decline upon continued culture. Selecting for and proliferating unattached cells 12 hrs after initial plating decreased microglial presence in culture to nearly undetectable levels. Cells cultured past 14 DIV displayed morphological and antigenic properties of purified type I protoplasmic astrocytes, exhibiting widespread expression of GFAP (93.1+/−3.2), S100β (89.8+/−4.1), and glutamine synthetase (90.4+/−4.4) (% positive+/−S.E.M.) (FIG. 3A). Nestin (92.2+/−3.9) was also frequently expressed, suggesting cells revert to an immature state (FIG. 3A). Astrocytes containing a stellate or reactive morphology were rarely detected in culture. To further describe these cells as astrocytes, we performed passive membrane recordings for high passage cultured cells (n=4). Recorded cells exhibited ubiquitous gliotypic membrane potentials, with an Rmp of −28.3+/−4.2 mV, Cm of 277.2+/−189.7 pF, Rm of 214.5+/−156.1 M, and Ra of 14.9+/−3.1 M. Recorded cells did not fire action potentials, and displayed prominent Na$^+$ channel activity and minimal K$^+$ channel activity (FIG. 3B). FACs analysis revealed one major population, with minimal side scatter.

The compounds or therapeutic compositions can function to regenerate nerve cells, promote neurite outgrowth, and protect nerves from otherwise damaging treatments or conditions. Thus, the compounds and compositions of this invention are useful in the diagnosis, cure, mitigation, treatment, or prevention of neurological conditions in animals, including humans, and in animals (including humans) exposed to neurodegenerative agents or having damaged nervous system cells. Such conditions and disorders, when present in an animal, including humans, can be neurodegenerative disorders, neuropathic disorders, neurovascular disorders, traumatic injury of the brain, spinal cord, or peripheral nervous system, demyelinating disease of the central or peripheral nervous system, metabolic or hereditary metabolic disorder of the central or peripheral nervous system, or toxin-induced- or nutritionally related disorder of the central or peripheral nervous system. When present in a human, a neurodegenerative disorder can be, for example, Parkinson's disease, Alzheimer's disease, amyotrophic lateral sclerosis (ALS), Huntington's disease, cerebellar ataxia, or multisystem atrophy including, for example, olivopontocerebellar degeneration, striatonigral degeneration, progressive supranuclear palsy, Shy-Drager syndrome, spinocerebellar degeneration and corticobasal degeneration. A demyelinating disease can be, for example, multiple sclerosis, Guillain-Barre syndrome, or chronic inflammatory demyelinating polyradiculoneuropathy. A neurovascular disorder can be global cerebral ischemia, spinal cord ischemia, ischemic stroke, cardiogenic cerebral embolism, hemorrhagic stroke, lacunar infarction, multiple infarct syndromes including multiple infarct dementia, or any disorder resulting in ischemia or ischemia/reperfusion injury of the central nervous system. Traumatic injury of the central or peripheral nervous system can be, for example, concussion, contusion, diffuse axonal injury, edema, and hematoma associated with craniocerebral or spinal trauma, or axonal or nerve sheath damage associated with laceration, compression, stretch, or avulsion of peripheral nerves or plexi, and further includes nerve damage caused during surgery, such as prostate surgery. A neuropathic disorder can be, for example, diabetic neuropathy, uremic neuropathy, neuropathy related to therapy with drugs such as phenyloin, suramin, taxol, thalidomide, vincristine or vinblastine; or neuropathy/encephalopathy associated with infectious disease, such as, for example, encephalopathy related to HIV, rubella virus, Epstein-Barr virus, herpes simplex virus, toxoplasmosis, prion infection. A metabolic disorder of the central nervous system can be, for example, status epilepticus, hypoglycemic coma, or Wilson's disease.

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

Materials and Methods

Isolation and Culture of Tissue

Primary tissue was gathered from individuals undergoing surgery related to medically intractable temporal lobe epilepsy. Primary tissue was removed and stored overnight in ice-cold DMEM/F-12 medium containing 20 mg/ml penicillin, 20 mg/ml streptomycin., and 25 ng/ml amphotericin B (collectively 1× antibiotics). Hippocampus (containing hilus) and temporal cortex (not containing subventricular zone) were microdissected from biopsied tissue samples (n=4, data presented from 17 year-old female). Dissected tissues were placed in 1× phosphate buffered saline (PBS, pH 7.3) lacking $CaCl_2$ or $MgCl_2$, and were manually dissociated into 1 $mm^3$ pieces under sterile conditions. Tissues were collected and resuspended in 0.005% trypsin (15 min, 37° C., pH 7.3), and were further triturated using restricted bore pipetting. Cells were collected, resuspended in proliferative media, and seeded onto uncoated T75 culture flasks overnight (12 hr, 37° C., 5% humidified CO2). Unattached cells were collected and seeded onto uncoated 60 mm plastic dishes in proliferative media. Proliferative media was comprised of DMEM/F-12 containing N2 supplements, 35 µg/ml bovine pituitary extract, 1× antibiotics, 5% fetal calf serum (FCS), and 40 ng/ml of EGF and FGF. 20 ng of EGF and FGF were supplemented twice daily. When necessary, media was changed every fourth day. Cells were frozen in aliquots of 1 million cells in DMEM/F-12 containing 10% FCS and 20% dimethyl sulfoxide (v/v). Cells were passaged 1:2 when confluent. Cells were dissociated with 0.005% trypsin, counted (using trypan dye exclusion as viability criteria), and were replated onto uncoated 60 mm plastic dishes. For growth monitoring experiments, 1 µg/ml aphidicolin or 20 µM EGCG were added to culture media 1 hour after plating. Irradiated cells were treated with a single 3 Gy dose of X-irradiation. Following the period of application, cells were washed in 1×PBS and were resuspended in proliferative media or fixed. To assess viability of cells in various growth conditions, equal numbers of culture-matched cells were seeded into triplicate wells of various proliferative conditions, and counted 7, 14, and 21 days later. For growth factor analysis, EGF and/or FGF were removed for seven days, and surviving cells were returned to proliferative media. Significance (p<0.05) was calculated using a student's t-test. In vitro images of cultured cells were captured using a Nikon Eclipse TS-100 bright field microscope and a Spot 3.1 digital camera (Diagnostic Instruments).

Immunocytochemistry

Cells were plated on coverslips coated with poly-L-lysine or polyornithine and laminin and grown to confluency in proliferative media. Cells were fixed with 4% paraformaldehyde (15 mM, 25° C.). After washing with PBS, cells were blocked 20 min in PBS containing 10% FCS, 5% normal goat serum, and 0.01% Triton X-100. Primary antibodies were applied for either 1 hour at 25° C. or overnight at 4° C. in PBS containing 10% FCS and 0.01% Triton X-100. Primary antibodies: β III tubulin (mouse monoclonal, 1:300, Promega), BrdU (mouse monoclonal, 1:50, Becton-Dickinson), CNPase (mouse monoclonal, 1:250, Chemicon), GFAP (rabbit polyclonal, 1:600, DAKO), glutamine synthetase (rabbit polyclonal, 1:100, AbCam), map2a-c (chicken polyclonal, 1:30,000), nestin (mouse monoclonal, 1:50, Chemicon), O4 (mouse monoclonal IgM, 1:150, Chemicon), S100-β (rabbit polyclonal, 1:100, Swant), telomerase (rabbit polyclonal, 1:200, Santa Cruz). Secondary antibodies were applied for 45 min at 25° C. in PBS containing 10% FCS and 0.01% Triton X-100. Secondary antibodies: Alexa-555 goat anti-chicken (1:300, Molecular Probes), Cy3 goat anti-mouse IgG (1:300, Jackson Labs), Cy3 goat anti-mouse IgM (1:600, Jackson Labs), Oregon Green goat ~rabbit (1:600, Molecular Probes). For BrdU imaging, cells were incubated in SSC-formamide (1:1, 37° C., 2 hr), washed 3×10 min in SSC, incubation in 2N HCl (37° C., 30 min), and washed with 0.1 M borate buffer (25° C., 10 min). SA-βGal expression was assessed 7 days after addition of growth arrestors as described (Dimri, G. P. et al. *Proc Nat'l Acad Sci USA* 92, 9363-7 (1995)). Briefly, cells were fixed in PBS containing 2% formaldehyde and 0.2% glutaraldehyde (25° C., 15 min). Following wash in PBS, cells were incubated (37° C., 12 hr) with fresh SA-βGal solution: 1 mg/ml 5-bromo-4-chloro-3-indolylβ-D-Galactosidase (X-Gal), 20 µg/ml dimethylforamide, and (in mM) 150 NaCl, 40 citric acid/sodium phosphate (pH 6.0), 5 potassium ferrocyanide, 2 $MgCl_2$. Nuclei were stained by application of either DAPI (1 µg/ml, 25° C., 10 mM) or propidium iodide (50 µg/ml, 25° C., 10 min) prior to mounting. Fluorescence microscopy was performed on a Leica DMLB upright microscope and images were captured with a Spot RT Color CCD camera (Diagnostic Instruments). All valued were expressed mean±S.E.M.

Electrophysiology

Cell culture media was removed and cells were perfused with continuously oxygenated (95% $O_2$ and 5% $CO_2$) artificial cerebrospinal fluid containing (in mM): 125 NaCl, 26 $NaHCO_3$, 20 glucose, 3 KCl, 2 $CaCl_2$, 1.25 $NaH_2PO_4$, and 1 $MgCl_2$. Cells were visualized using Axioskop-FS DIC microscope (Zeiss). Patch electrodes were pulled from borosilicate capillary glass using a Flaming-Brown P-87 microelectrode puller (Sutter Instruments) and had a resistance of 4-6 MΩ when filled with internal solution comprising of (in mM): 130 K-gluconate, 10 HEPES, 0.2 EGTA, 2 ATP and 0.3 GTP (pH 7.2, osmolarity 290). Whole-cell recordings were performed with an Axopatch-1D (Axon Instruments) at room temperature and data was acquired and assembled using Clampex 8.2 software (Axon Instruments). Series resistances were 10-20 MΩ and recordings were discarded if a change of series resistances was >10%. Cells were held at −65 mV. Na and K currents were elicited by applying voltage steps to cells (−80 to +60 mV, increment: 15 mV, duration: 300 ms). The values of capacitance and input resistance were obtained by applying 10 mV voltage pulse to cells. All values were expressed mean±S.E.M.

Western Blot Analysis

Cells were lysed in a modified RIPA buffer containing (in mM): 150 NaCl, 50 EDTA (pH 7.5), 50 sodium β-glycerophosphate, 50 NaF, 5 sodium pyrophosphate, 2 EDTA, 2 EGTA, 1 DTT, 1 phenylmethylsulfonyl fluoride, 1 sodium orthovanadate with 1% Triton X-100, 10 µg/ml leupeptin, and 10 µg/ml aprotinin. Equal amounts of lysates were resolved on a 12% SDS-polyacrylamide gel and transferred to a nitrocellulose membrane. The membrane was blocked in TBST [20 mM Tris-HCl (pH 7.5), 500 mM sodium chloride, and 0.05% Tween-20] containing 5% nonfat dry milk for 2 hours and then incubated with primary antibodies in TBST containing 1% BSA at room temperature for 2 hours. Primary antibodies:TERT (1:200, rabbit anti-human Santa Cruz), p53 (mouse anti-human, 1:500, Santa Cruz), p21 (rabbit anti-human, 1:200, Santa Cruz), p16 (rabbit anti-human, 1:200, Santa Cruz), cyclin A (rabbit anti-human, 1:200, Santa Cruz), cyclin D1 (mouse anti-human, 1:2000, Santa Cruz), cyclin E (rabbit anti-human, 1:200, Santa Cruz). Horseradish peroxidase-labeled secondary antibodies were applied in TBST containing 5% nonfat dry milk for 2 hours. Secondary antibodies: donkey anti-rabbit (1:10,000, Amersham), donkey anti-mouse (1:5000, Amersham). Protein was visualized by using an enhanced chemiluminescence (ECL) detection system.

Karyotyping

All cytogenetic analysis was done by the University of Florida core facility for cytogenetics. Briefly, confluent cell layers were incubated with 300 μL Karymax, dissociated with 0.05% trypsin and resuspended in 75 mM KCl for 6 minutes. Cells were collected and resuspended in 3:1 (vol/vol) ethanol:acetic acid. Cells were visualized on a coverslip using light microscopy. Seven metaphasic cells were observed and described.

Neurosphere Formation

Cultured cells were placed in neurosphere conditions as described. Briefly, cells were seeded at a density of 50,000 cells/ml in proliferative media containing 1% methylcellulose in anti-adhesive conditions. EGF and FGF were supplemented twice daily, and neurosphere formation was visually tracked using light microscopy at 7, 14, and 21 days.

Example 1

Isolation and Culture of Primary Cells

To isolate regionally specific tissue for long-term culture, anterolateral temporal lobe neocortex was removed from patients undergoing temporal resection associated with medically intractable epilepsy. Tissue was microdissected into regions containing hippocampus or temporal cortex gray matter. All procedures were performed with informed consent and were performed in accordance with human tissue handling and use guidelines. Tissues were triturated to single cells and maintained as a monolayer on uncoated plastic dishes throughout culture in defined proliferative media, modified from a standard protocol for the culture of neural stem cells. Growth media contained Dulbecco's Modified Eagle Medium with nutrient mix F-12 (DMEM/F-12) containing N2 supplements, fetal bovine serum, antibiotics, bovine pituitary extract, epidermal growth factor (EGF) and basic fibroblast growth factor (FGF).

To identify cultured cell types, primary cells were examined for expression of immunotypic markers throughout culture. Following explantation, immunocytochemistry on primary cells 3 days in vitro (DIV) revealed a heterogeneous population containing predominantly astrotypic (GFAP$^+$) cells. Neuronal (NeuN$^+$, PSA-NCAM$^+$) and oligodendrocyte (CNPase$^+$, O4$^+$) phenotypes were occasionally detected in early cultures, but rarely divided when cultured with bromodeoxyuridine (BrDU). Presumptive neurons and oligodendrocytes were not appreciated in culture after 14 divisions. High passage cultured cells (>60 population cell divisions) display morphological and antigenic properties of type I astrocytes, exhibiting widespread expression of glial fibrillary acidic protein (GFAP) (93.1±3.2), S1000 (89.8±4.1), and glutamine synthetase (90.4±4.4) (% positive±S.E.M.) (FIG. 1A). β III tubulin (87.7±4.6) and nestin (92.2±3.9) were also prominently displayed, suggesting cells actively divide throughout culture period (FIG. 1A). In initial cultures, microglia (CD11$^+$) were also present and did not significantly decline upon continued culture. However, selection and proliferation of unattached cells 12 hrs after initial plating decreased microglial frequency to nearly undetectable levels.

To further describe these cells as astrocytes, passive membrane recordings for high passage cultured cells (n=4), were performed. These cells were gliotypic, with an $R_{mp}$ of −28.3±4.2 mV, $C_m$ of 277.2±189.7 pF, $R_m$ of 214.5±156.1 MΩ, and $R_a$ of 14.9+/−3.1 MΩ. Cultured cells do not fire action potentials, and demonstrate prominent Na$^+$ channel activity and minimal K$^+$ channel activity (FIG. 1A).

Astrocyte-like cells have been implicated as "immortal" neural stem-like cells (NSCs) maintained throughout life in the hippocampus and subventricular zone. In rodents and humans, these cells have been described as existing throughout life and cells cultured from these regions may represent a system-specific stem cell population dividing in excess of the limits placed on somatic cells. To detect potential NSCs, low and high passage cells were assayed for neurosphere formation as described. Clonally seeded cells failed to generate neurospheres, suggesting they were not NSCs. However, clonal cells remained viable for up to 14 days, as evidenced by their continued growth following substrate reattachment. Attempts to induce differentiation in adherent cells as previously described for attached human neurospheres were unsuccessful in producing multiple differentiated cell types.

To determine replicative limits for neural cells, cells were expanded in culture and quantified using cell counting. Upon explantation into culture, neural cells re-entered the cell cycle and were expandable with specific mitogens. Primary neural cells were grown continuously for 30 days prior to quantification of growth (approximately 10 population cell divisions) to ensure a uniform population of astrocytes. Following the initial culture period, 10$^6$ cells from hippocampus and temporal cortex were plated in proliferative media and supplemented with EGF and FGF twice daily. Upon reaching confluency, cultured cells were passaged 1:2 and counted. Both temporal cortex and hippocampus were maintained continuously in defined growth medium for over 300 DIV (>60 population cell divisions) (FIG. 1C), equivalent to one cell giving rise to >10$^{18}$ cells. Cultured cells maintain their general morphology throughout culture and display a constant, contact inhibited doubling rate for both hippocampus and temporal cortex (0.34±0.04 and 0.35±0.04 cell divisions/day respectively) (FIG. 1C).

Example 2

Cultured Cells Maintain Growth Sensitivity and Avoid Immortalization

A notable exception to proliferation limits are immortalized tumors, which are able to circumvent cell cycle regulation and expand indefinitely. These cells are distinguishable from normal somatic cells in several ways. Immortalized cells accumulate neoplastic mutations in genes linked to cell cycle control, apoptosis, and survival, and may be characterized by a lack of response to physiological or chemical arrestors of the cell cycle. Furthermore, transformed cells often exhibit irregular growth rates, and do not undergo growth contact inhibition in monolayer cultures.

Figure 2:
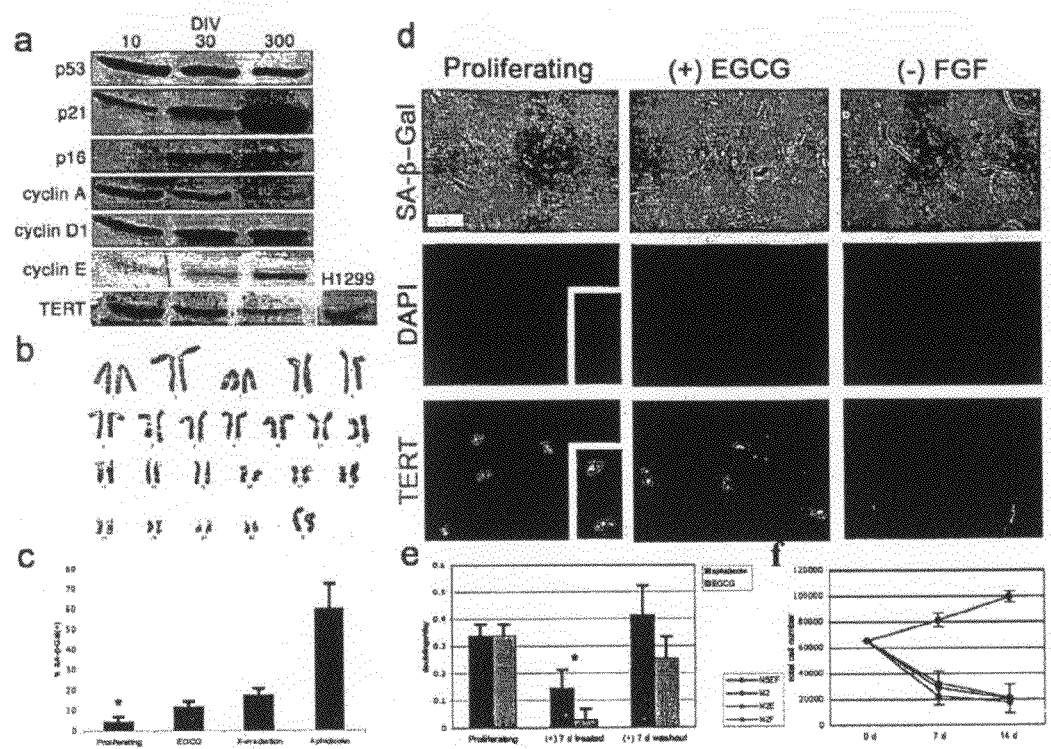
FIGS. 2A-2F show that high passage cell populations avoid immortalizing mutations, and exhibit condition- and telomerase-dependent growth.

Immortalization of human cells is marked by the aberrant expression of key regulatory proteins. To determine the activation status of cell cycle proteins in cultured cells, protein levels for major cell cycle regulatory proteins were measured throughout culture period (FIG. 2A). Cultured cells longitudinally express major cell cycle checkpoints, including p16, which is reported to be essential for immortalization of both epithelial cells and astrocytes in humans. Though p53 remains constant throughout culture, other cdk inhibitory proteins (e.g., p21) and cyclins (e.g., cyclin E) increased throughout the culture period. This observation agrees with observed increases in both promitotic and inhibitory proteins during indefinite culture of glia in rodents. TERT was expressed at high levels upon initial culture, matching a report of initial expression of telomerase in fetal human brain tissue.

Surprisingly, TERT continues to be expressed at low levels throughout culture. Karyotypic analysis of metaphasic high passage cells (n=7) revealed no gross cytogenetic abnormalities in high passage cells (FIG. 2B).

To determine whether extensively doubled cell populations remain sensitive to chemical and physiological regulators of the cell cycle, high passage cells were treated. with DNA synthesis inhibitor aphidicolin or X-irradiation and were assessed for senescence-associated β-galactosidase (SA-β-gal), a marker for senescent cells (FIGS. 2C and 2D), 7 days later. Cultured cells express significantly higher levels of SA-β-gal than age-matched controls, suggesting cell cycle checkpoint mechanisms remain sensitive throughout culture period.

Telomerase, the holoenzyme responsible for telomeric extension, is longitudinally expressed in cultured cells. To investigate the relationship between telomerase expression and continued growth in culture, the telomerase inhibitor epigallocatechin-3-gallate (EGCG) was added to high passage cell media, and growth rate and telomerase expression were measured 7 days later (FIGS. 2D and 2E). TERT expression remained detectable in cultured cells, but the rate of cellular proliferation was significantly reduced (FIG. 2E). To further investigate factors controlling the expression of telomerase and the growth of these cells, EGF, FGF, and serum were selectively removed from culture medium of high passage cells. Removal of any growth factor resulted in the loss of telomerase expression within 7 days accompanied by a failure to continue to proliferate (FIGS. 2D and 2E). Interestingly, cells treated with EGCG or aphidicolin returned to normal growth rates within 7 days following re-plating in proliferative media (FIG. 2E). However, cells deprived of growth factor did not return to previous proliferative levels and subsequently became non-viable (FIG. 2E).

Less than 4% of high passage cells (>60 cell divisions) exhibited SA-β-gal, suggesting cells continue to be mitotically active (FIG. 2C). Multinucleated and/or giant cells, characteristic of senescent cells, were rarely expressed at any point throughout culture period.

Example 3

Rapid Expansion of Purified, Transplantable Cells

Significant attention has been focused on the development of primary human neural tissue sources for multiple applications in the central and peripheral nervous system (CNS, PNS). Primary cells derived from adult brain provide the committed, developmentally matched cell types desirable for transplantation populations and bioassays when reverted to proliferating precursor populations in vitro. However, these adult populations are limited by a lack of expandability in culture (Kiyono et al., (1998) *Nature* 396:84-88; Evans et al., (2003) *Cancer Res* 63:4854-4861).

Overcoming this barrier in cultured proliferating cells would allow useful expansion of cell populations for a variety of applications. This lack of expandability of primary human cells is potentially linked to the cell cycle arrest and entry into senescence via activation of the p21WAF1 (and subsequent activation of the p16INK4A) pathway, which has been reported to initially arrest growth of cultured astrocytes after 20 population cell divisions (Evans et al., 2003, supra) (PDs). Furthermore, the lack of telomerase expression in non-neurogenic regions of human brain may be a limiting factor in the expansion of glial cell populations. Catalytic telomerase (TERT) is believed to play a critical role in maintaining telomere length, and has been related to lifespan in a variety of human tissues. Though TERT expression has been reported in the neuropoietic regions of adult rodents only low levels of telomerase have been reported in ex-vivo cultured human cells (Ostenfeld et al., (2000) *Cells* 22:798-811).

Glial cells comprise the majority of CNS cell types, and are increasingly recognized for their role in injury (i.e., glial scar formation (Silver and Miller, (2004) *Nat Rev Neurosci* 5:146-156) and disease (i.e., secretion of neuroprotective factors (Kordower, 2003; Tai Y T, (2004) *Ann Neurol* 53 Suppl 3:S120-132; discussion S132-124), and have become attractive candidate for expansion for use in therapeutic applications.

To test the possibility of a dramatic expansion of primary adult glia, growth conditions favoring the propagation of gliotypic neural progenitor/stem cells to dissociated tissue monolayers derived from both neurogenic and non-neurogenic postnatal brain, were applied. Using these conditions, a population of highly expandable somatic (HES) astroglial progenitors was isolated in vitro. These cells retain characteristics consistent with type I astrocytes, and have been maintained for over 300 days and >60 PDs with minimal signs of senescence or immortalizing mutations. Interestingly, HES astroglia derived from both neurogenic and non-neurogenic regions express telomerase longitudinally throughout culture, a similarity to neural stem cells that appears connected to a synergistic mitogenic effect and the continued growth of HES astroglia.

To test the ability of ex vivo astrocytes to integrate into the CNS, expanded astrocytes were grafted into the ventricles of postnatal rodents. Cells effectively integrate and maintain a gliotypic phenotype, suggesting a potential use as a transplant population in addressing injured or diseased tissue requiring glial contribution. Genetic modification of HES astroglia was achieved using both transient and long-term transfection approaches. Finally, it was possible to dedifferentiate HES astroglia, resulting in the rapid generation of neuronal cell types. These findings suggest a means for rapid expansion of purified, transplantable, and genetically modifiable astroglial cell populations, allowing for new applications of easily obtainable postmortem or autologous cell sources.

Isolation and Culture of Tissue: Primary tissue was gathered from individuals undergoing surgery related to medically intractable temporal lobe epilepsy. Primary tissue was removed and stored overnight in ice-cold DMEM/F-12 (Gibco, Grand Island, N.Y.) medium containing antibiotics (20 mg/ml penicillin, 20 mg/ml streptomycin, and 25 ng/ml amphotericin B, Sigma, St. Louis, Mo.). Hippocampus (containing hilus) and temporal cortex (not containing subventricular zone) were microdissected from biopsied tissue samples (n=4, data presented from 17 year-old female). Dissected tissues were placed in 1× phosphate buffered saline (PBS, pH 7.3) lacking $CaCl_2$ or $MgCl_2$, and were manually dissociated into 1 $mm^3$ pieces under sterile conditions. Tissues were collected and resuspended in 0.005% trypsin (15 min, 37° C., pH 7.3, Sigma), and were further triturated using restricted bore pipetting. Cells were collected, resuspended in proliferative media, and seeded onto uncoated T75 culture flasks overnight (12 hr, 37° C., 5% humidified $CO_2$). Unattached cells were collected and seeded onto uncoated 60 mm plastic dishes in proliferative media. Proliferative media was comprised of DMEM/F-12 containing N2 supplements, 35 μg/ml bovine pituitary extract (Sigma), 1× antibiotics, 5% fetal calf serum (FCS, Hyclone, Logan, Utah), and 40 ng/ml of EGF and FGF (R&D, Minneapolis, Minn.). 20 ng of EGF and FGF were supplemented bidaily. When necessary, media was changed every fourth day. A total of 6 lines from 4 patients were gathered. Cells were frozen in aliquots of 1 million cells in DMEM/F-12 containing 10% FCS and 20% dimethyl sulfoxide (v/v, Sigma). Cells were passaged 1:2 when confluent. Cells were dissociated with 0.005% trypsin, counted (using trypan dye exclusion as viability criteria), and were replated onto uncoated 60 mm plastic dishes (Sigma). For growth monitoring experiments, 1 µg/ml aphidicolin or 20 µM EGCG (Sigma) were added to culture media 1 hour after plating. Irradiated cells were treated with a single 3 Gy dose of X-irradiation. Following period of application, cells were washed in 1×PBS and were resuspended in proliferative media or fixed. To assess viability of cells in various growth conditions, equal numbers of culture-matched cells were seeded into triplicate wells of various proliferative conditions, and counted 7, 14, and 21 days later. For growth factor analysis, EGF and/or FGF were removed for seven days, and surviving cells were returned to proliferative media. Significance ($p<0.05$) was calculated using a student's t-test.

In vitro images of cultured cells were captured using a Nikon Eclipse TS-100 bright field microscope and a Spot 3.1 digital camera (Diagnostic Instruments, Sterling Heights, Mich.).

Immunocytochemistry: Cells were plated on coverslips coated with poly-L-lysine or polyornithine and laminin and grown to confluency in proliferative media. Cells were fixed with 4% paraformaldehyde (15 min, 25° C., Sigma). After washing with PBS, cells were blocked 20 min (attached cells) or 2 hours (tissue sections) in PBS containing 10% FCS, 5% normal goat serum (Sigma), and 0.01% Triton X-100 (Sigma). Primary antibodies were applied for either 1 hour at 25° C. or overnight at 4° C. in PBS containing 10% FCS and 0.01% Triton X-100. Primary antibodies: βIII tubulin (mouse monoclonal, 1:300, Promega, Madison, Wis.), BrDU (mouse monoclonal, 1:50, BD Biosciences, San Jose, Calif.), CNPase (mouse monoclonal, 1:250, Chemicon, Temecula, Calif.), GFAP (rabbit polyclonal, 1:600, DAKO, Carpinteria, Calif.), glutamine synthetase (rabbit polyclonal, 1:100, Abeam, Cambridge, Mass.), GFP (rabbit polyclonal, 1:300, Chemicon), human nuclear antigen (mouse monoclonal, 1:300, Acris, Hiddenhausen, Germany), Ki-67 (mouse monoclonal, 1:300, BD Biosciences), map2a-c (chicken polyclonal, 1:30,000, gift from Dr. Gerry Shaw), nestin (mouse monoclonal, 1:50, Chemicon), neurofilament M (mouse monoclonal, 1:500, gift from Dr. Gerry Shaw), O4 (mouse monoclonal IgM, 1:150, Chemicon), S100-(rabbit polyclonal, 1:100, Swant, Bellinzona, Switzerland), telomerase (rabbit polyclonal, 1:200, Santa Cruz Biotechnology, Santa Cruz, Calif.). Secondary antibodies were applied for 1 hr at 25° C. in PBS containing 10% FCS and 0.01% Triton X-100. Secondary antibodies: Alexa-555 goat anti-chicken (1:300, Molecular Probes, Carlsbad, Calif.), Cy3 goat anti-mouse IgG (1:300, Jackson Labs, West Grove, Pa.), Cy3 goat anti-mouse IgM (1:600, Jackson Labs), Oregon Green goat anti-rabbit (1:600, Molecular Probes). For BrDU imaging, cells were incubated in SSC-formamide (1:1, 37° C., 2 hr), washed 3×10 min in SSC, incubation in 2N HCl (37° C., 30 min), and washed with 0.1 M borate buffer (25° C., 10 min). Tissue sections were pretreated with 1% $H_2O_2$ in 70% methanol (15 min, 25° C.) and visualized using an ABC Elite detection kit (Vector Labs, Burlingame, Calif.). SA-βGal expression was assessed 7 days after addition of growth arrestors as described (Dimri et al., (1995) *Proc Nat'l Acad Sci USA* 92:9363-9367. Briefly, cells were fixed in PBS containing 2% formaldehyde and 0.2% glutaraldehyde (25° C., 15 min). Following wash in PBS, cells were incubated (37° C., 12 hr) with fresh SA-βGal solution: 1 mg/ml 5-bromo-4-chloro-3-indolyl β-D-Galactosidase (X-Gal, Sigma), 20 µg/ml dimethylforamide (Sigma), and (in mM) 150 NaCl, 40 citric acid/sodium phosphate (pH 6.0), 5 potassium ferrocyanide, 2 $MgCl_2$ (Sigma). Nuclei were stained by application of either DAPI (1 µg/ml, 25° C., 10 min, Sigma) or propidium iodide (50 µg/ml, 25° C., 10 min, Sigma) prior to mounting. Fluorescence microscopy was performed on a Leica DMLB upright microscope (Bannockburn, Ill.) and images were captured with a Spot RT color CCD camera (Diagnostic Instruments). Confocal microscopy was performed on an Olympus IX-70 microscope (Melville, N.Y.) using Confocal 1024 ES software (Bio-Rad, Hercules, Calif.). All valued were expressed mean±S.E.M.

Electrophysiology: Cell culture media was removed and cells were perfused with continuously oxygenated (95% $O_2$ and 5% $CO_2$) artificial cerebrospinal fluid containing (in mM): 125 NaCl, 26 $NaHCO_3$, 20 glucose, 3 KCl, 2 $CaCl_2$, 1.25 $NaH_2PO_4$, and 1 $MgCl_2$ (Sigma). Cells were visualized using Axioskop-FS DIC microscope (Zeiss, Thornwood, N.Y.). Patch electrodes were pulled from borosilicate capillary glass using a Flaming-Brown P-87 microelectrode puller (Sutter Instruments, Novato, Calif.) and had a resistance of 4-6 M when filled with internal solution comprising of (in mM): 130 K-gluconate, 10 HEPES, 0.2 EGTA, 2 ATP and 0.3 GTP (pH 7.2, osmolarity 290). Whole-cell recordings were performed with an Axopatch-1D (Molecular Devices, Sunnyvale, Calif.) at room temperature and data was acquired and assembled using Clampex 8.2 software (Molecular Devices). Series resistances were 10-20 MΩ and recordings were discarded if a change of series resistances was >10%. Cells were held at −65 mV. Na and K currents were elicited by applying voltage steps to cells (−80 to +60 mV, increment: 15 mV, duration: 300 ms). The values of capacitance and input resistance were obtained by applying 10 mV voltage pulse to cells. All valued were expressed mean±S.E.M.

Western Blot Analysis: Cells were lysed in a modified RIPA buffer containing (in mM): 150 NaCl, 50 EDTA (pH 7.5), 50 sodium β-glycerophosphate, 50 NaF, 5 sodium pyrophosphate, 2 EDTA, 2 EGTA, 1 DTT, 1 phenylmethylsulfonyl fluoride, 1 sodium orthovanadate with 1% Triton X-100, 10 µg/ml leupeptin, and 10 µg/ml aprotinin (Sigma). Equal amounts of lysates were resolved on a 12% SDS-polyacrylamide gel and transferred to a nitrocellulose membrane. The membrane was blocked in TBST [20 mM Tris-HCl (pH 7.5), 500 mM sodium chloride, and 0.05% Tween-20] containing 5% nonfat dry milk for 2 hours and then incubated with primary antibodies in TBST containing 1% BSA at room temperature for 2 hours. Primary antibodies: TERT (1:200, rabbit anti-human, Santa Cruz), p53 (mouse anti-human, 1:500, Santa Cruz), p21 (rabbit anti-human, 1:200, Santa Cruz), p16 (rabbit anti-human, 1:200, Santa Cruz), cyclin A (rabbit anti-human, 1:200, Santa Cruz), cyclin D1 (mouse anti-human, 1:2000, Santa Cruz), cyclin E (rabbit anti-human, 1:200, Santa Cruz).

Horseradish peroxidase-labeled secondary antibodies were applied in TBST containing 5% nonfat dry milk for 2 hours. Secondary antibodies: donkey anti-rabbit (1:10,000, Amersham, Piscataway, N.J.), donkey anti-mouse (1:5000, Amersham). Protein was visualized by using an enhanced chemiluminescence (ECL) detection system (Amersham).

Karyotyping: All cytogenetic analysis was done by the University of Florida core facility for cytogenetics. Briefly, confluent cell layers were incubated with 300 µL Karyomax (Gibco), dissociated with 0.05% trypsin and resuspended in 75 mM KCl for 6 minutes. Cells were collected and resuspended in 3:1 (vol/vol) ethanol:acetic acid. Cells were visualized on a coverslip using light microscopy. Seven metaphasic cells were observed and described.

Transplantation: Cultured astrocytes (30 PDs) were trypsinized and resuspended in PBS. $1 \times 10^5$ cells were injected into the right lateral ventricle of anesthetized postnatal day 3 C57/B6 mice (n=6). Animals were sacrificed and perfused with 4% paraformaldehyde 7 days later. Brains were placed in 30% sucrose solution overnight, and were sectioned into 25 sagittal and coronal sections on a freezing microtome. Brain sections were stored at −20° C. in cryoprotectant solution until analyzed. Immunosuppressed animals (n=3) were injected with 10 mg/kg cyclosporin A (Sigma) immediately prior to transplantation and bidaily thereafter.

Transfection: Cultured astrocytes (30 PDs) were plated on polyornithine-laminin coverslips at a density of 500 cells/cm$^2$ in defined proliferative media. Two hours after plating, cells were transfected with Pax6-IRES-eGFP plasmid (Haubst et al., (2004) *Development* 131:6131-6140) using a standard protocol for Superfect transfection reagent (Qiagen, Valencia, Calif.) with 1 µg DNA or Effectene transfection reagent (Qiagen) containing 4 µg DNA. Transfectants were removed 8 hours later and were replaced with defined proliferative media. Cells were evaluated for endogenous eGFP expression or were probed with eGFP antibody 24, 36, or 72 hours later. Lentiviral vectors containing the human eGFP gene were generated as described previously (Iwakuma et al., (1999) *Virology* 261:120-132), and were transfected at 5, 10, and 20 moi. Cells were evaluated 7 days following transfection.

Neurosphere Formation and Dedifferentiation: Passage 1 cultured astrocytes were placed in neurosphere conditions as described (Kukekov et al., (1999) *Exp Neurol* 156:333-344). Briefly, cells were seeded at a density of 5×10$^4$ cells/ml in proliferative media containing 1% methylcellulose in anti-adhesive conditions. EGF and FGF were supplemented bidaily, and neurosphere formation was visually tracked using light microscopy at 7, 14, and 21 days. Matched cultures of clonal seedings were prepared every fifth passage. To dedifferentiation of adherent cells serum, EGF and FGF were removed from the culture media and a subset supplemented with 0.5 mM IBMX, 0.5 mM 1-dibutyryl cAMP, and 25 ng/ml NGF (Ronnett et al., (1990) *Science* 248:603-605). Matched withdrawal cells were cocultured with 10 mM BrDU for 2 days following factor addition. Cells were immunocytochemically evaluated 2, 3, 5 and 7 days later, and were electrophysiologically evaluated 7 days following dedifferentiation.

Results: Isolation and Expansion of Primary Cells: To isolate regionally specific tissues for long-term culture, anterolateral temporal lobe neocortex was removed from patients undergoing resection associated with medically intractable epilepsy. Tissue was microdissected into regions containing hippocampus, subventricular zone or temporal cortex gray matter. All procedures were performed with informed consent and were performed in accordance with human tissue handling and use guidelines. Tissues were triturated to single cells and maintained as a monolayer on uncoated plastic dishes throughout culture in defined proliferative media, modified from a standard protocol for the culture of neural stem cells (Svendsen et al., (1998) *J Neurosci Methods* 85:141-152). Growth media contained Dulbecco's Modified Eagle Medium with nutrient mix F-12 (DMEM/F-12) containing N2 supplements, fetal bovine serum, antibiotics, bovine pituitary extract, epidermal growth factor (EGF) and basic fibroblast growth factor (FGF).

To identify cultured cell types, primary cells were examined for expression of phenotypic markers. Following dissociation, immunocytochemistry on primary cells 3 days in vitro (DIV) revealed a heterogeneous population containing predominantly astrocytic (GFAP+) cells, but included neuronal (NeuN+, PSA-NCAM+) and oligodendrocyte (CN-Pase+, O4+) phenotypes. Following their explantation into culture, only astrotypic cells appear to re-enter the cell cycle as shown by their uptake of thymidine analog 5-bromodeoxyuridine (BrDU) and were expandable as a purified population with specific mitogens. Presumptive neurons and oligodendrocytes were not appreciated in culture after 14 DIV. Microglia (CD11$^+$) were present initially and did not significantly decline upon continued culture. Selecting for and proliferating unattached cells 12 hrs after initial plating decreased microglial presence in culture to nearly undetectable levels. Cells cultured past 14 DIV displayed morphological and antigenic properties of purified type I protoplasmic astrocytes, exhibiting widespread expression of GFAP (93.1+/−3.2), S100β (89.8+/−4.1), and glutamine synthetase (90.4+/−4.4) (% positive+/−S.E.M.) (FIG. 3A). Nestin (92.2+/−3.9) was also frequently expressed, suggesting cells revert to an immature state (FIG. 3A). Astrocytes containing a stellate or reactive morphology were rarely detected in culture. To further describe these cells as astrocytes, we performed passive membrane recordings for high passage cultured cells (n=4). Recorded cells exhibited ubiquitous gliotypic membrane potentials, with an R$_{mp}$ of −28.3+/−4.2 mV, C$_m$ of 277.2+/−189.7 pF, R$_m$ of 214.5+/−156.1 MΩ, and R$_a$ of 14.9+/−3.1 MΩ. Recorded cells did not fire action potentials, and displayed prominent Na$^+$ channel activity and minimal K$^+$ channel activity (FIG. 3B). FACs analysis revealed one major population, with minimal side scatter.

To determine the proliferative limits for purified glial cells in these conditions, cells were grown in vitro and their expansion quantified via cell counting. To ensure a purified astroglial population for measurement of proliferation, neural cell dissociates were grown continuously for 30 days prior to quantification of growth (≈10 PDs) to remove non-astroglial cells. Following this initial culture period, 10$^6$ cells from hippocampus and temporal cortex were plated in defined proliferative media and supplemented with EGF and FGF bidaily. Upon reaching confluency, cultured cells were passaged 1:2 and total cell number counted. Both temporal cortex and hippocampal astrocytes exhibited logarithmic growth expansion in defined growth medium for over 300 DIV (>60 PDs) (FIG. 3C), equivalent to one cell giving rise to >10$^{18}$ cells. Astrocytes derived from both regions maintain similar morphologies and size throughout culture (FIG. 3D) and maintain a constant, contact-inhibited growth rate for both hippocampal- and temporal cortex-derived cells (0.34+/−0.04 and 0.35+/−0.04 cell divisions/day respectively) (FIG. 3E).

Astrocyte-like cells have been implicated as "immortal" neural stem-like cells (NSCs) maintained throughout life in the hippocampus and subventricular zone (Laywell et al., (2000) *Proc Natl Acad Sci USA* 97:13883-13888; Seri et al., (2001) *Proc Natl Acad Sci USA* 98:113-118; Sanai et al., (2004) *Nature* 427:740-744). In rodents and humans, these cells have been described as existing throughout life (Tropepe et al., (1997) *J Neurosci* 17:7850-7859; Sanai et al., 2004) and cells cultured from these regions may represent a system-specific stem cell population which can be expanded beyond the limits ascribed to somatic cells. To detect potential NSCs, temporal cortex and hippocampal astrocytes were assayed for neurosphere formation as described (Kukekov et al., (1999) *Exp Neurol* 156:333-344) every fifth passage. HES astroglia failed to generate neurospheres at clonal seeding densities at any point, suggesting they were not NSCs. However, clonal cells remained viable for up to 14 days, as evidenced by their continued growth following substrate reattachment. Attempts to induce differentiation in adherent cells as previously described for attached human neurospheres (Ostenfeld and Svendsen, (2004) *Cells* 22:798-811) and adherent neural stem cells (Scheffler et al., (2005) *Proc Natl Acad Sci USA* 102:9353-9358) were unsuccessful in producing multiple differentiated cell types.

HES Astroglia Maintain Growth Sensitivity and Avoid Immortalization: Purified expanding cell populations may undergo growth-specific genetic modification(s) resulting in circumvention of cell cycle regulatory mechanisms and manifesting in an immortalized phenotype, allowing for extensive clonal expansion similar to that observed. Immortalized cells frequently contain accumulated neoplastic mutations in genes linked to cell cycle control, apoptosis, and survival, and may be characterized by a lack of response to physiological or chemical arrestors of the cell cycle. Furthermore, transformed cells often exhibit irregular or hyperplasic growth rates, and can be tumorigenic when transplanted. To determine whether such immortalizing mutations were present in HES astroglial cells, the molecular and cytogenetic profiles of expanded astrocytes, were examined.

Figure 4:
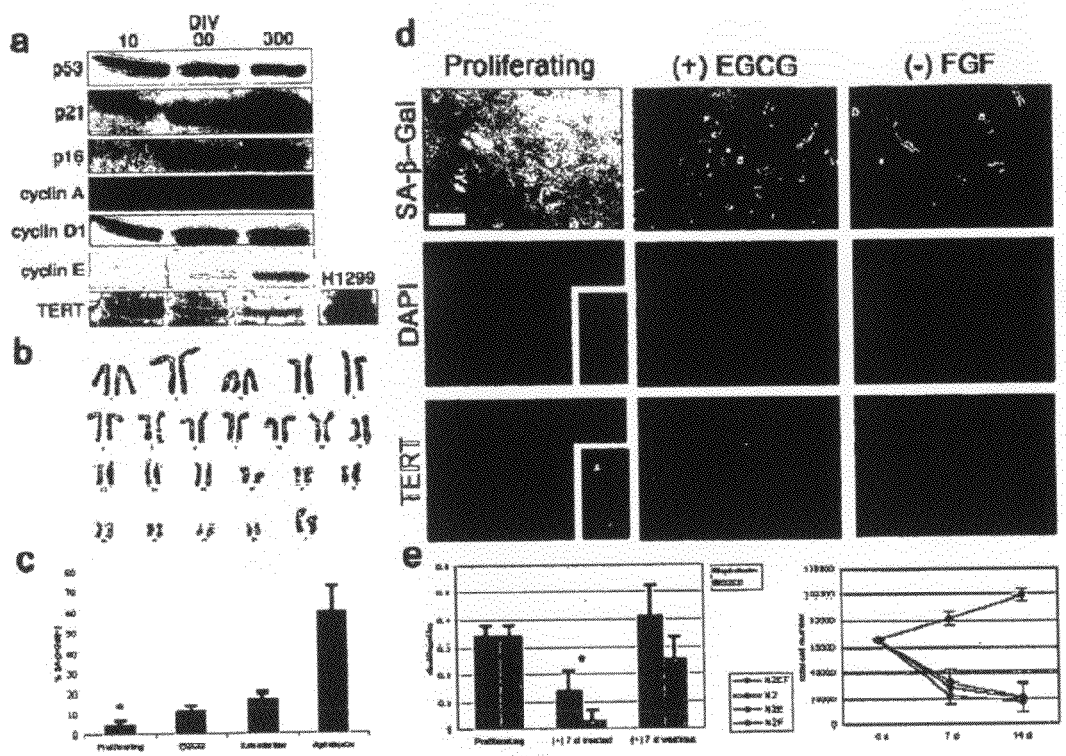
FIGS. 4A-4E show HES astroglia avoid immortalizing mutations, and exhibit condition- and telomerase-dependent growth.

Immortalization of human cells is frequently marked by the aberrant expression of key regulatory proteins. To determine the activation status of cell cycle proteins in expanding cells, protein expression levels for major cell cycle regulatory proteins were measured throughout the culture period (FIG. 4A). Cultured astrocytes longitudinally express major cell cycle checkpoints, including p53, a key initiator of cellular senescence. Expanding cultures express p16, the deletion of which is reported to be essential for immortalization in both epithelial cells (Kiyono et al., (1998) *Nature* 396:84-88) and astrocytes (Evans et al., (2003) *Cancer Res* 63:4854-4861) in humans (FIG. 4A). Though p53 remains constant throughout culture, other cdk inhibitory proteins (i.e., p21) and cyclins (i.e., cyclin E) increased throughout the culture period. This observation agrees with noted increases in both promitotic and inhibitory proteins during the extended culture of glia in rodents (Mathon et al., (2001) *Science* 291:872-875); Tang et al., (2001) *Science* 291:868-871). Interestingly, robust TERT expression was appreciated in cultured cells initially. TERT is expressed at progressively lower levels during expansion in defined proliferative conditions. None of the populations examined (n=6 from 4 individuals) was capable of indefinite growth (>70 measured PDs). Karyotypic analysis of metaphasic high passage cells (n=7) revealed no gross cytogenetic abnormalities in high passage cells (FIG. 4B).

To determine whether HES astroglia remain sensitive to chemical and physiological regulators of the cell cycle, high passage cells were treated with the DNA synthesis inhibitor aphidicolin or X-irradiation and were assessed for senescence associated O-galactosidase (SA-β-gal), a marker for senescent cells (Dimri et al., 1995) (FIGS. 4C, 4D), 7 days later. Treated cells expressed significantly higher levels of SA-β-gal than age-matched controls, suggesting cell cycle checkpoint mechanisms remain sensitive throughout culture period.

Telomerase, the holoenzyme responsible for telomeric extension, is longitudinally expressed during the observed period of growth. This is unique, as telomerase is rarely reported in adult neural tissue, and its expression and loss may be related to the continuing expandability of cells in culture. To investigate the relationship between telomerase expression and continued growth in culture, the telomerase inhibitor epigallocatechin-3-gallate (Naasani et al., (1998) *Biochem Biophys Res Commun* 249:391-396) (EGCG) was added to highly expanded cells, and telomerase expression and growth rate were measured 7 days later (FIGS. 4C-4E). Despite significant reduction in the rate of cellular proliferation, TERT expression remained ubiquitous in expanding HES astroglia (FIG. 4E). To examine the potential relationship between growth conditions, telomerase expression, and expandability in HES astroglia EGF, FGF, and serum were selectively removed from culture medium of highly expanded cells. Removal of any growth factor resulted in the loss of telomerase expression within 7 days accompanied by a failure to continue to proliferate (FIG. 4D, 4E). Interestingly, HES astroglia treated with EGCG or aphidicolin returned to normal growth rates within 7 days following replating in proliferative media, while cells deprived of growth factor failed to regain previous proliferative levels and subsequently became unviable (FIG. 4E).

Less than 4% of HES astroglia exhibited SA-gal in defined proliferative conditions, suggesting cells continue to be mitotically active and are expandable for over 60 PDs (FIG. 4C): Multinucleated and/or giant cells, characteristic of senescent cells, were rarely observed at any point throughout culture period.

Figure 5:
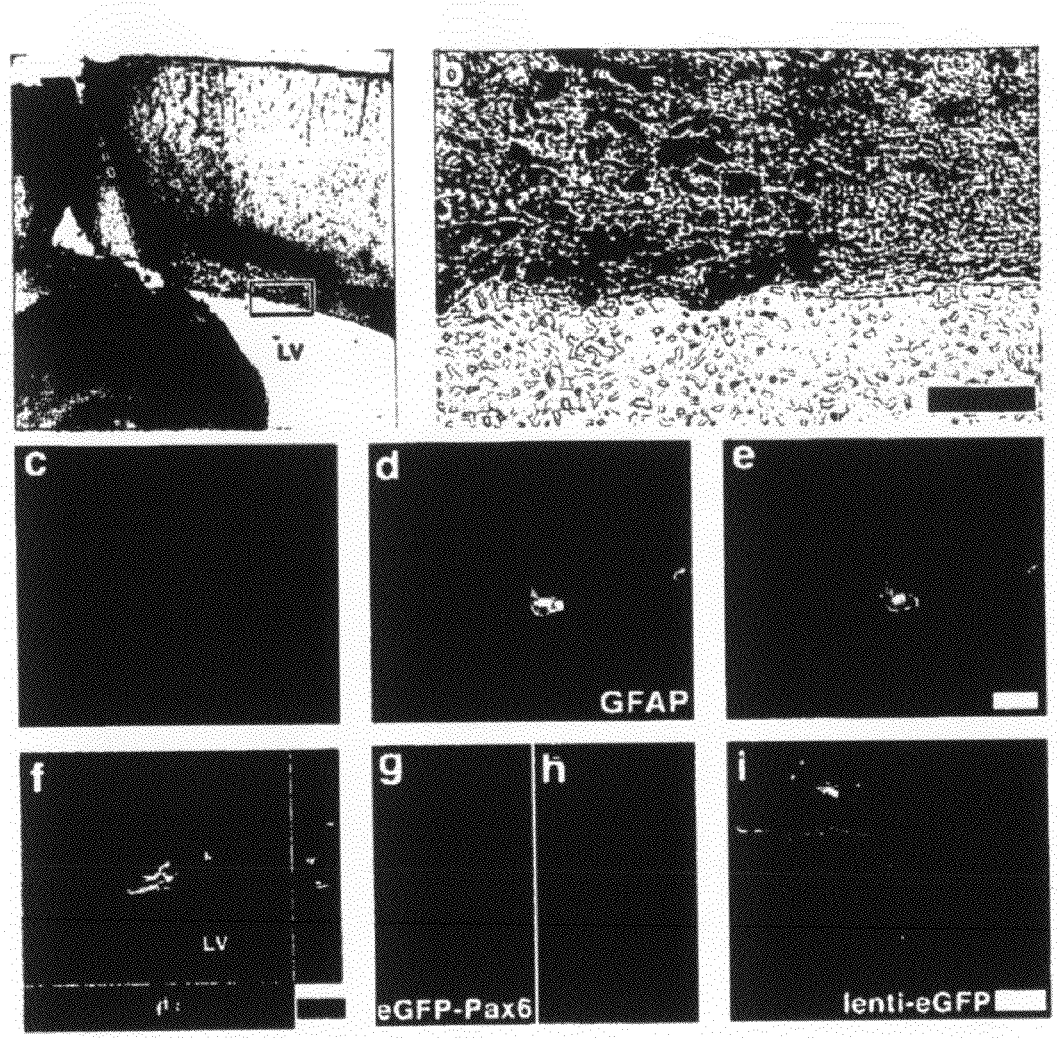
FIGS. 5A-5I are images showing that HES astroglia maintain viability upon transplantation.

Expanded Astrocytes Function as a Transplantable, Modifiable Cell Source: To assess the ability of HES astroglia to survive, integrate, and re-assume an astroglial phenotype in vivo, $10^5$ astrocytes (50 PDs) were suspended and injected into the right lateral ventricle of early postnatal C57/B6 mice. Cells were assessed for integration and immunophenotype 7 days later using human nuclear antigen (HNA) to identify engrafted cells. Moderate reactive gliosis was appreciated in nonimmunosupressed animals, with many surviving cells detected in the choroid plexus. Immunosupression of animals with cyclosporin A increased integration frequency and engrafted cell distribution substantially, and largely eliminated reactive gliosis. Engrafted cells were primarily detected in the injected ventricle, with increasing frequency adjacent to the injection site (FIG. 5A, 5B). HNA cells were also detected adjacent to the third ventricle and cerebellar aqueduct and (rarely) in the hippocampus. Integrated cells were immunohistochemically identified, and were frequently found to coexpress GFAP (FIGS. 5A-5F). Engrafted cells did not coexpress neuronal markers, and rarely expressed nestin, suggesting they mature and become largely postmitotic upon integration.

Ex vivo genetic modification of transplantable cells with various gene products is a frequently envisioned strategy in drug delivery and neuroprotective paradigms (Kordower, 2003; Tai YT, (2004) *Curr Opin Pharmacol* 4:98-104). To examine the amenability of these cells to genetic modification, HES astroglia were transfected with a plasmid containing a 2 kb gene encoding the neural patterning gene Pax6 and enhanced green fluorescent protein (eGFP) using both activated dendrimer transfection and non-liposomal lipid transformation techniques. Stably transfected cells were detected at low frequency 3 days following transfection (FIG. 5G, 5H). HES astroglia were also genetically modifiable using a lentiviral vector expressing human eGFP (FIG. 5I).

Figure 6:
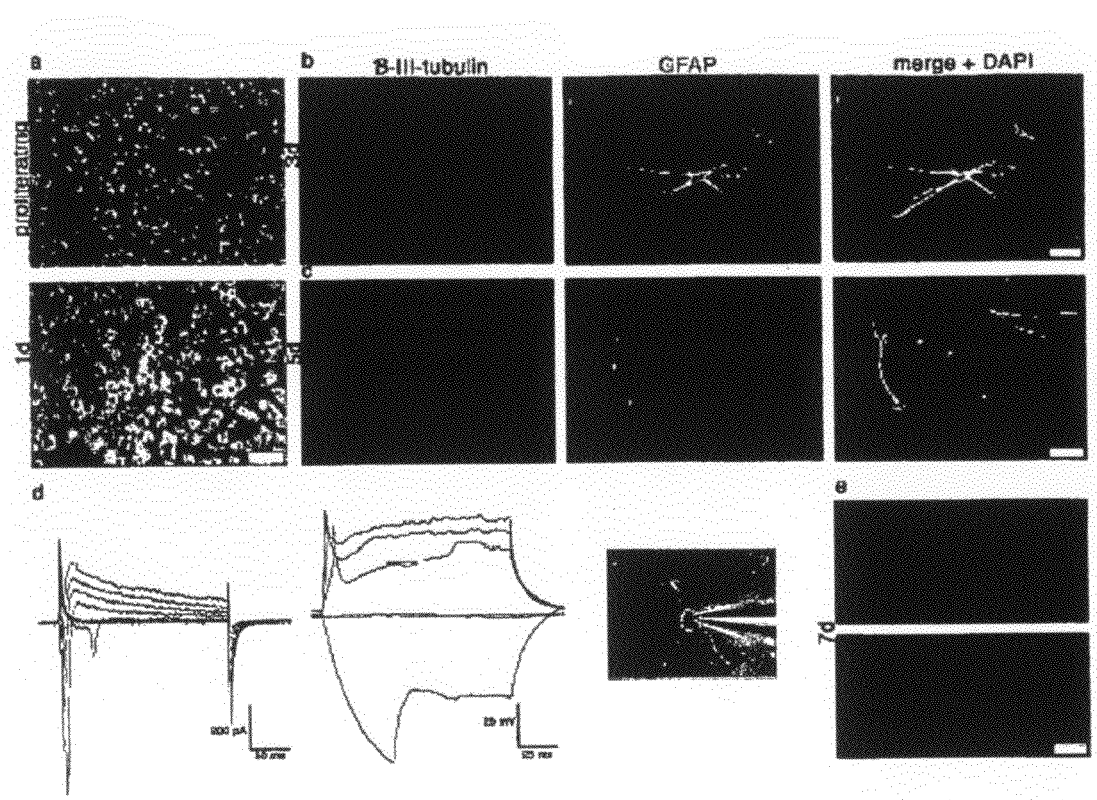
FIGS. 6A-6E show dedifferentiation of HES astroglia into neuronal cell types.

To test the potential for alteration of phenotype in HES astroglia, expanded cells (>20 PDs) were subjected to multiple combinations of culture supplements, including FGF8, retinoic acid, dibutyl cAMP, nerve growth factor (NGF), and 1-isobutyl-3-methylxanthine (IBMX). Application of dibutyl cAMP, NGF, and IBMX, combined with the removal of growth factors, was found to induce a rapid phenotypic alteration in proliferating cells (FIG. 6A) that yielded morphologically and electrophysiologically characteristic immature neurons within 7 days. When examined 3 days following this induction of phenotypic alteration, a subset of cells displayed a hybridized somato-dendritic morphology intermediate to astrocyte and neuron, and displayed both neuronal and astrocytic markers (FIG. 6B). These intermediate cells progressively mature to form neuronal cells expressing a conserved morphology and characteristic immunophenotypic markers (FIG. 6C, 6E). Few cells in either an intermediate or neuronal form expressed BrDU or Ki-67, suggesting they were alterations of cultured cells. Cells at this developmental stage (n=4) display electrophysiological characteristic reminiscent of immature neuronal characteristics: $R_{mp}$ of −33+/−20.8 mV, $C_m$ of 32.6+/−1.3 pF, $R_m$ of 1.3+/−0.3 GΩ, and $R_a$ of 16.7+/−5.5 MΩ, with prominent $Na^+$ and $K^+$ channels when (FIG. 6D). Immature neurons were capable of firing evoked action potentials (FIG. 6D). Oligodendrocytes were not detected following addition of culture supplements.

Discussion: We have demonstrated a method for isolating purified populations of protoplasmic astrocytes from primary neural tissue and have described culture conditions necessary for their extensive expansion. HES astroglia maintain a stable doubling rate throughout culture, and do not exhibit characteristics of transformed cells, including loss of key cell cycle checkpoint proteins, loss of sensitivity to arrestors of the cell cycle, and cell contact inhibition of growth. These results suggest it is possible to significantly expand a purified population of committed astroglial cells for potential biomedical application without senescence or cellular transformation.

Similar to all embryonic- germ- and certain adult stem-cells, telomerase is ubiquitously expressed in cultured cells, initially at high levels and at subsequently lower levels. Unlike immortalized cells, telomerase expression is not coupled to a loss of key regulatory proteins required for immortalization (Kiyono et al., (1998) *Nature* 396:84-88); Evans et al., (2003) *Cancer Res* 63:4854-4861). Thus, the observed growth phenotype is a hybrid one, allowing expansion past proliferative limits while avoiding immortalizing mutations.

Cultured cells appear to be almost exclusively type I protoplasmic astrocytes. Comparison of cells derived from the hippocampus and temporal cortex revealed no differences in growth rates, cellular composition, or significant physiological factors. This is interesting, as the hippocampus is believed to contain astrocyte-like NSCs that have self-renewal and multipotentiality in vitro and in vivo (Eriksson et al., (1998) *Nat Med* 4:1313-1317). Utilizing a paradigm adapted from the generation of neuronal cell types from cortical neuronal cell lines (Ronnett et al., (1990) *Science* 248:603-605), it was possible to generate immature neurons in a similar manner. New neurons do not appear to be generated in culture, as is the case in studies to date for conventional postnatal neurogenesis (Laywell et al., 2000; Seri et al., 2001; Sanai et al., 2004; Scheffler et al., 2005), as they lack ubiquitous BrDU incorporation and cell cycle marker expression characteristic of dividing cells. Transforming cells appear to possess an "asteron" hybrid phenotype, similar to cultured rodent neural cells (Okano-Uchida et al., (2004) *Proc Natl Acad Sci USA* 101:1211-1216). Whereas the previous studies report a neuron-to-glia transdifferentiation, the transition reported here represents a glia-to-neuron commitment, suggesting the isolation of conditions for the alteration of phenotype for somatic neural cells may be possible. The results suggest that these cells are not NSCs, but have the potential to generate neuronal phenotypes.

HES astroglia remain sensitive to exogenous cell cycle inhibitors (aphidicolin, EGCG), but continue to express telomerase and return to previous levels of proliferation upon removal of exogenous growth inhibitors. However, upon mitogenic withdrawal, telomerase expression is promptly lost and continued proliferation ceases, neither of which is restored upon reversion to defined proliferative media. This anecdotal coupling of TERT expression to cellular proliferation provides for several interesting possibilities. First, these results suggest a system whereby environmental mitogens (provided inconstant supply) provide a condition-specific synergistic growth effect, allowing for both TERT expression and continued expansion. A loss of environmental support factors may trigger a demonstrably irreversible loss of TERT expression, which may effectively mortalize cells or possibly, in the case of HES astroglia, trigger their immediate and irreversible entry into a state of replicative senescence. The appreciation of rapid senescence with the loss of TERT expression in aged cells suggests that both telomere length and telomerase expression may be critical to the maintenance of continued cell division in highly expanded populations. This agrees with a number of reported examples of poor correlation between telomere length and replicative senescence, including one example in which cells rescued from replicative senescence by viral transfection of telomerase maintained shorter telomere length than replication incompetent counterparts (Yang et al., (1999) *J Biol Chem* 274: 26141-26148; Zhu et al., (1999) *Proc Natl Acad Sci USA* 96:3723-3728).

The ability to massively expand glial cell populations possesses implications for diagnostic neurobiology as well as for therapeutic approaches involving tissue replacement. By extensively expanding primary cells from various brain regions, it is possible to create a substrate for neural cell bioassays (i.e., primary drug testing) without relying on clonally derived cell lines that contain potentially masking genotoxic mutations or inaccurately reflect the homeostenosis of target cells. Recent efforts for cell replacement therapies in the brain have prompted a focus on transplantation biology, including the use of glia genetically modified to express neurotrophins (Kordower, 2003; Tai Y T, 2004, supra). Employing a logarithmic ex vivo expansion of endogenous cells allows heretofore unprecedented applications in neurotransplantation and neural cell bioassays. This fact, combined with the demonstrated amenability to alteration of gene expression and fate choice in these cells provides an exciting substrate for further investigations addressing disease and injury.

Example 4

Transplantation of Human Neuronal Phenotypes $1 \times 10^5$ human neural progenitors were transplanted 1 mm right of the midline at a depth of 1 mm into the right cortex of adult NOD-SOD immunodeficient mice. Cells were suspended in phosphate buffered saline in a total fluid volume of 2 μl. Transplanted animals were allowed to survive a total of 30 days, and were then sacrificed and evaluated for engraftment of human cells. Integrating human cells were identified by both morphology (specifically increased size relative to host cells) and immunoreactivity for human nuclear antigen. Cells detected were primarily localized around the injection site, with the majority of cells remained in the cortex within 250 μm of the injection site (FIG. 7, left column). A small subset of cells were detected lateral to the site of cortical injection, suggesting human cells have a limited ability to undergo a tangential migration. Occasionally, cells were detected in other structures, including the hippocampus (FIG. 7, left column). Cells were immunophenotyped using antibody labeling. The majority of cells (>90%) appear to adopt neuronal morphologies and express the neuronal marker beta-III-tubulin. Occasional astrocytic phenotypes are detected, as are cells that do not express a mature phenotype.

The integration of these cells is interesting for several reasons: first, neuronal cell types are generally rare in transplants of adult progenitor populations. Second, the migration of these cells of distances up to 2 mm is an exceptional finding, suggesting that these cells may be useful for a number of transplant applications requiring long distance neuronal projections (i.e., Parkinson's disease). Third, as these progenitors are isolatable from multiple brain regions, it is likely that these cells could be gathered and expanded for this use using a minimally invasive technique, an advancement over current surgical interventions such as deep brain stimulation. Fourth, the ability of these cells to integrate over a period of 30 days is highly relevant, suggesting these cells may function as a transplant source that can stably integrate over a long period of time. Fifth, the generation of a preponderance of neuronal fates suggests that these cells may be useful as precursors for generating neuronal morphologies, a particularly difficult aspect of differentiating neural progenitors. Such populations may compete with the additional existing applications, including the use of more ethically and legally controversial embryonic and fetal tissue.

In the generation of neuronal cell types in vivo, there were no exogenous chemical agents given (compared to the addition of multiple in vitro differentiation agents, including cyclic AMP analogs, IBMX, and nerve growth factor). This suggests an endogenous generation of a preponderance of neuronal cell types from the source of transplantable progenitors. Additionally, the highly expandable nature of these tissues makes for a concurrent generation of large numbers of neuronal phenotypes, which may be able to provide a therapeutic recourse in chronic degenerative disorders, such as Alzheimer's disease or Parkinson's, which may require constant cellular infusions to replace dying cells.

Observation of these cells after one month post-transplantation showed no cells expressing characteristics of hyperplasic transformation, including the formation of tumors or unusual metastasis. Transplanted cells possess elaborate morphologies which are unlikely to undergo further expansion and are thus at minimal risk for formation of malignancies.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing a population of neuronal cells of a neural tissue of a subject, comprising the steps of:
    (a) obtaining a population of isolated somatic astroglial progenitor cells expressing GFAP and capable of being maintained for at least 300 days in culture and at least 60 cell divisions, wherein the step (a) of obtaining the population of isolated somatic astroglial progenitor cells comprises the steps of:
        (i) obtaining a neural tissue from an adult subject;
        (ii) triturating the neural tissue, or a sample thereof, to produce a suspension comprising neural cells of the neural tissue;
        (iii) introducing said suspension of neural cells to a tissue culturing system having an uncoated substrate surface;
        (iv) culturing the cells under conditions suitable for the proliferation of said neural cells;
        (v) removing unattached neural cells from the tissue culturing system, delivering said unattached neural cells to an uncoated substrate of a tissue culturing system, and culturing said cells under conditions suitable for the proliferation of said cells as an adherent layer on the uncoated substrate of the tissue culturing system, and not as neurospheres, wherein said conditions comprise a proliferative medium comprising N2 supplements, bovine pituitary extract, fetal calf serum, EGF and FGF; and
        (vi) isolating said adherent layer of cultured cells from the tissue culturing system, thereby obtaining a population of isolated somatic astroglial progenitor cells; and
    (b) delivering the population of isolated somatic astroglial progenitor cells into a recipient subject, whereupon at least a fraction of the population of said delivered isolated somatic astroglial progenitor cells differentiates into neuronal cells but not into oligodendrocytes, thereby increasing a population of neuronal cells in the recipient subject, or differentiating at least a fraction of the population of isolated somatic astroglial progenitor cells into neuronal cells but not into oligodendrocytes and delivering said neuronal cells into a recipient subject, thereby increasing a population of neuronal cells of the recipient subject.

2. The method of claim 1, wherein the step of differentiating the population of isolated somatic astroglial progenitor cells before delivery to a recipient subject comprises culturing said progenitor cells in a medium comprising at least one of the group consisting of: retinoid compound, brain-derived neurotrophic factor (BDNF), platelet-derived growth factor (PDGF), nerve growth factor (NGF), sonic hedgehog, sonic hedgehog amino terminal peptide, neurotrophin (NT)-3, neurotrophin (NT)-4, and wherein the isolated somatic astroglial progenitor cells differentiate into cells having the characteristics of neuronal cells but not of oligodendrocytes.

3. The method of claim 1, wherein the differentiated cells are characterized by a at least one neuronal cell marker selected from the group consisting of neurofilament M, neural-specific β-tubulin, neural-specific enolase, and microtubule associated protein 2, and further comprises a morphological criterion of at least one neurite-like process at least 50 micrometers in length, and wherein the differentiated cells are not oligodendrocytes.

* * * * *